US011154368B2

(12) United States Patent
Yeung et al.

(10) Patent No.: US 11,154,368 B2
(45) Date of Patent: Oct. 26, 2021

(54) PORT ASSEMBLY FOR USE WITH ROBOTIC DEVICES AND SYSTEMS TO PERFORM SINGLE INCISION PROCEDURES AND NATURAL ORIFICE TRANSLUMENAL ENDOSCOPIC SURGICAL PROCEDURES

(71) Applicant: Bio-Medical Engineering (HK) Limited, Hong Kong (CN)

(72) Inventors: Chung-Kwong Yeung, Hong Kong (CN); Chuk Shing Jones Law, Hong Kong (CN); Wai Lik Alik Chan, Hong Kong (CN)

(73) Assignee: Bio-Medical Engineering (HK) Limited, Hong Kong (CN)

( * ) Notice: Subject to any disclaimer, the term of this patent is extended or adjusted under 35 U.S.C. 154(b) by 0 days.

(21) Appl. No.: 16/057,381

(22) Filed: Aug. 7, 2018

(65) Prior Publication Data

US 2018/0344415 A1    Dec. 6, 2018

Related U.S. Application Data

(60) Continuation-in-part of application No. 15/662,921, filed on Jul. 28, 2017, now Pat. No. 10,039,608, (Continued)

(51) Int. Cl.
*A61B 34/30*    (2016.01)
*A61B 34/37*    (2016.01)
(Continued)

(52) U.S. Cl.
CPC .......... *A61B 34/30* (2016.02); *A61B 17/3421* (2013.01); *A61B 17/3462* (2013.01); (Continued)

(58) Field of Classification Search
CPC ......... A61B 34/30; A61B 34/37; A61B 34/76; A61B 90/361; A61B 90/50;
(Continued)

(56) References Cited

U.S. PATENT DOCUMENTS 7,090,637 B2    8/2006  Danitz et al.
7,410,483 B2    8/2008  Danitz et al.
(Continued)

FOREIGN PATENT DOCUMENTS

AU    2013245548 A1    11/2013
CA       2720572 A1     6/2011
(Continued)

OTHER PUBLICATIONS

Office Action issued in connection with Chinese Patent Application No. 201610257789.8 dated Nov. 1, 2017, 11 pages.
(Continued)

*Primary Examiner* — Lynsey C Eiseman
*Assistant Examiner* — Jessandra F Hough
(74) *Attorney, Agent, or Firm* — Baker & McKenzie LLP

(57) ABSTRACT

Example embodiments relate to surgical devices, systems, and methods. The system may include a port assembly. The port assembly may be for use with a surgical arm assembly having a surgical arm and elongated anchor section. The port assembly may include a first main body having an elongated body and a main channel. The main channel may be formed by a portion of an interior surface of the elongated body. The main channel may extend between the proximal and distal ends of the elongated body. The first main body may include an instrument gate secured at a proximal end of the main channel. The instrument gate may include an expandable opening configured to be in a persistently closed position. The expandable opening may be configurable to adaptively
(Continued)

expand to a shape of a cross-section of a surgical arm when the surgical arm is inserted through the expandable opening.

19 Claims, 37 Drawing Sheets

Related U.S. Application Data which is a division of application No. 15/044,889, filed on Feb. 16, 2016, now Pat. No. 9,737,372, which is a continuation of application No. 14/693,207, filed on Apr. 22, 2015, application No. 16/057,381, which is a continuation of application No. 15/044,895, filed on Feb. 16, 2016, now abandoned, which is a continuation-in-part of application No. 14/693,207, filed on Apr. 22, 2015, application No. 16/057,381, which is a continuation-in-part of application No. 16/028,982, filed on Jul. 6, 2018, which is a continuation-in-part of application No. 15/044,895, filed on Feb. 16, 2016, now abandoned, which is a continuation-in-part of application No. 14/693,207, filed on Apr. 22, 2015.

(60) Provisional application No. 61/982,717, filed on Apr. 22, 2014.

(51) Int. Cl.
  *A61B 90/00* (2016.01)
  *A61B 17/34* (2006.01)
  *A61B 1/00* (2006.01)
  *A61B 90/50* (2016.01)
  *A61B 34/00* (2016.01)
  *A61B 90/30* (2016.01)
  *A61B 17/00* (2006.01)
  *A61B 1/313* (2006.01)
  *A61B 17/29* (2006.01)

(52) U.S. Cl.
  CPC ............ *A61B 34/37* (2016.02); *A61B 90/361* (2016.02); *A61B 1/00087* (2013.01); *A61B 1/3132* (2013.01); *A61B 17/29* (2013.01); *A61B 34/76* (2016.02); *A61B 90/50* (2016.02); *A61B 2017/00278* (2013.01); *A61B 2017/00283* (2013.01); *A61B 2017/00876* (2013.01); *A61B 2017/2906* (2013.01); *A61B 2017/345* (2013.01); *A61B 2017/3445* (2013.01); *A61B 2034/301* (2016.02); *A61B 2034/302* (2016.02); *A61B 2034/305* (2016.02); *A61B 2090/309* (2016.02); *A61B 2090/3612* (2016.02); *Y10S 901/02* (2013.01); *Y10S 901/27* (2013.01)

(58) Field of Classification Search
  CPC .......... A61B 17/3421; A61B 2034/305; A61B 2090/309; A61B 2090/3612; A61B 1/00087; A61B 1/3132; A61B 2017/00283; A61B 2017/3445; A61B 2017/345; Y10S 901/02; Y10S 901/27
  See application file for complete search history.

(56) References Cited

U.S. PATENT DOCUMENTS

| | | | |
|---|---|---|---|
| 8,083,667 | B2 | 12/2011 | Cooper et al. |
| 8,891,924 | B2 | 11/2014 | Yeung et al. |
| 9,060,798 | B2 | 6/2015 | Harper et al. |
| 9,737,372 | B2 | 8/2017 | Yeung et al. |
| 10,105,128 | B2 | 10/2018 | Cooper et al. |
| 2005/0096502 | A1 | 5/2005 | Khalili |
| 2007/0123855 | A1 | 5/2007 | Morley et al. |
| 2007/0175961 | A1 | 8/2007 | Shelton, IV et al. |
| 2008/0255519 | A1* | 10/2008 | Piskun ............... A61B 1/32 604/174 |
| 2008/0287963 | A1* | 11/2008 | Rogers ............... A61B 34/30 606/130 |
| 2009/0326318 | A1 | 12/2009 | Tognaccini et al. |
| 2010/0036198 | A1 | 2/2010 | Tacchino et al. |
| 2010/0137681 | A1 | 6/2010 | Ewers et al. |
| 2010/0331857 | A1 | 12/2010 | Doyle et al. |
| 2011/0118736 | A1 | 5/2011 | Harper et al. |
| 2011/0201883 | A1* | 8/2011 | Cooper ............. A61B 17/3421 600/109 |
| 2012/0022553 | A1 | 1/2012 | Cooper et al. |
| 2012/0279343 | A1 | 11/2012 | Ihrke et al. |
| 2013/0131695 | A1* | 5/2013 | Scarfogliero ........ A61B 34/30 606/130 |
| 2013/0144395 | A1 | 6/2013 | Stefanchik et al. |
| 2013/0289579 | A1 | 10/2013 | Yeung et al. |
| 2013/0317521 | A1 | 11/2013 | Choi et al. |
| 2014/0128882 | A1 | 5/2014 | Kwak et al. |
| 2015/0150634 | A1 | 6/2015 | Isoda |
| 2015/0282828 | A1* | 10/2015 | Kishi ................ A61B 1/00006 600/106 |
| 2015/0282875 | A1 | 10/2015 | Harper et al. |
| 2015/0297299 | A1 | 10/2015 | Yeung et al. |
| 2015/0327750 | A1 | 11/2015 | Ogawa |
| 2016/0157948 | A1 | 6/2016 | Yeung |

FOREIGN PATENT DOCUMENTS

| | | |
|---|---|---|
| CN | 101106951 A | 1/2008 |
| CN | 101500470 A | 8/2009 |
| CN | 101999938 A | 4/2011 |
| CN | 102100573 A | 6/2011 |
| CN | 101400293 B | 7/2011 |
| CN | 201968771 U | 9/2011 |
| CN | 102614006 A | 8/2012 |
| CN | 202505440 U | 10/2012 |
| CN | 202637006 U | 1/2013 |
| CN | 203290975 U | 11/2013 |
| CN | 103431913 A | 12/2013 |
| CN | 103533898 A | 1/2014 |
| CN | 103582462 A | 2/2014 |
| CN | 1004224324 A | 12/2014 |
| CN | 104883991 A | 9/2015 |
| CN | 105358072 A | 2/2016 |
| CN | 105816242 A | 8/2016 |
| CN | 105832418 A | 8/2016 |
| CN | 107440799 A | 12/2017 |
| CN | 107485415 A | 12/2017 |
| CN | 107616840 A | 1/2018 |
| CN | 107661144 A | 2/2018 |
| CN | 107961078 A | 4/2018 |
| CN | 108697474 A | 10/2018 |
| CN | 109567943 A | 4/2019 |
| CN | 109715081 A | 5/2019 |
| CN | 109890580 A | 6/2019 |
| EP | 3501413 A1 | 6/2019 |
| WO | 9510241 | 4/1995 |
| WO | 2007146987 A3 | 12/2007 |
| WO | 2011135503 A1 | 11/2011 |
| WO | 2015161677 A1 | 10/2015 |
| WO | 2016059369 A1 | 4/2016 |

OTHER PUBLICATIONS

International Search Report and Written Opinion, PCT/CN2016/076385, dated May 27, 2016, 16 pages.
International Search Report and Written Opnion, PCT/CN2017/086204, dated Aug. 25, 2017.
International Search Report and Written Opinion, PCT/CN2016/076376, dated May 25, 2016, 10 pages.
Chinese Office Action dated Jul. 8, 2019 in connection with Chinese Application No. 201710714234.6, 13 pages.

(56) References Cited

OTHER PUBLICATIONS

Chinese Office Action dated Jul. 4, 2019 in connection with Chinese Application No. 201710713625.6, 10 pages.
Chinese Office Action dated Jul. 8, 2019 in connection with Chinese Application No. 201710713638.8, 13 pages.
International Search Report dated Mar. 28, 2019 in connection with International Application No. PCT/CN2018/099830, 7 pages.
Written Opinion of the International Searching Authority dated Mar. 28, 2019 in connection with International Application No. PCT/CN2018/099830, 4 pages.
Examination Report dated Jan. 28, 2020 in connection with Indian Application No. 201617017442, 7 pages.
Examination Report dated Dec. 10, 2019 in connection with Indian Application No. 201717002757, 5 pages.
Examination Report dated Feb. 6, 2020 in connection with Indian Application No. 201817034862, 6 pages.
First Office Action dated Mar. 19, 2020 in connection with Chinese Application No. 201910749590.0, 7 pages.
First Office Action dated Aug. 5, 2020 in connection with Chinese Application No. 201810337515.9, 11 pages.
First Examination Report dated Jun. 23, 2020 in connection with Indian Application No. 201817037446, 6 pages.
Third Office Action dated Jun. 22, 2020 in connection with Chinese Application No. 201710714234.6, 8 pages.
First Examination Report dated Apr. 27, 2020 in connection with Indian Application No. 201817037452, 7 pages.

* cited by examiner

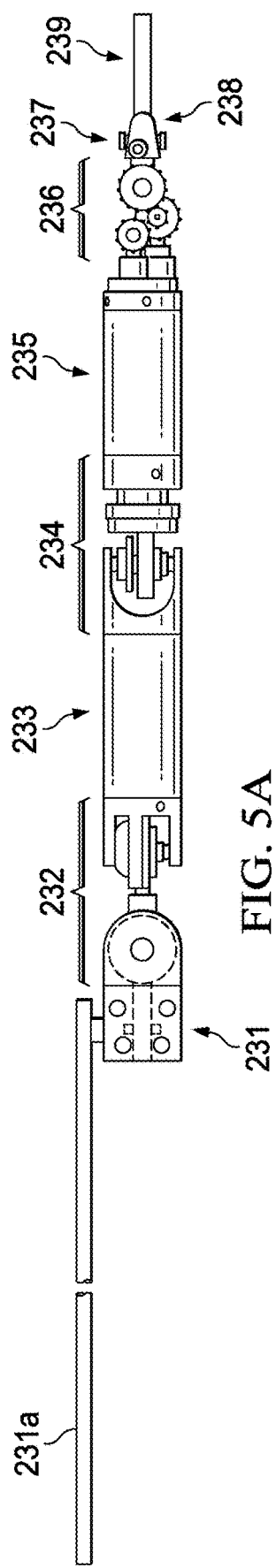
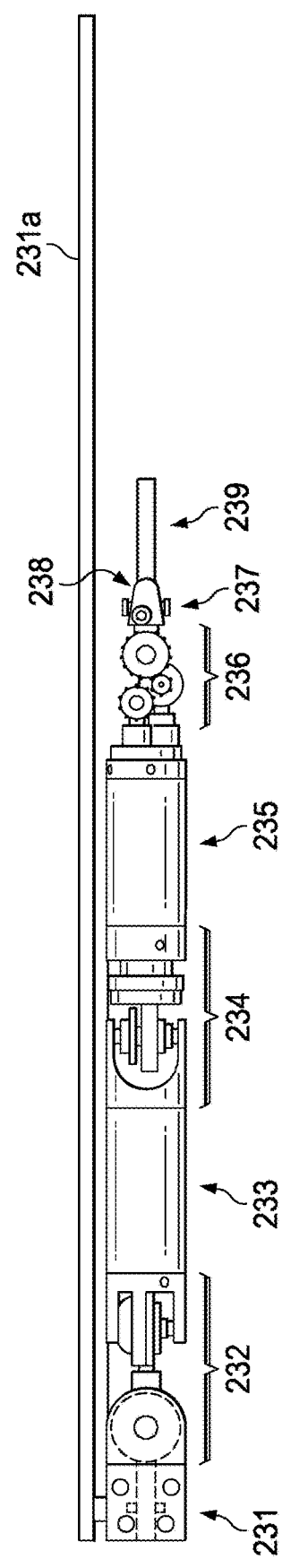
FIG. 5A
FIG. 5B

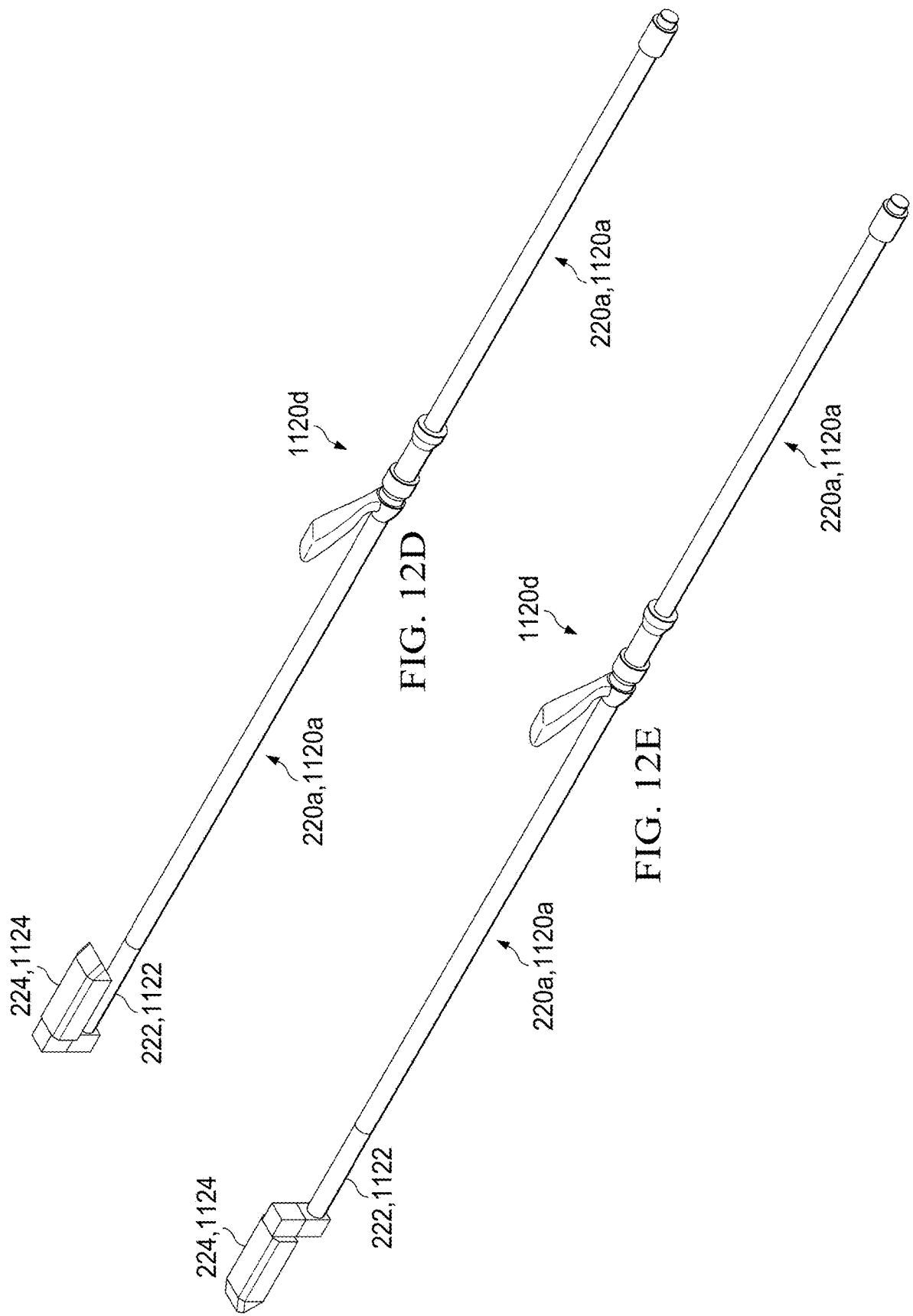

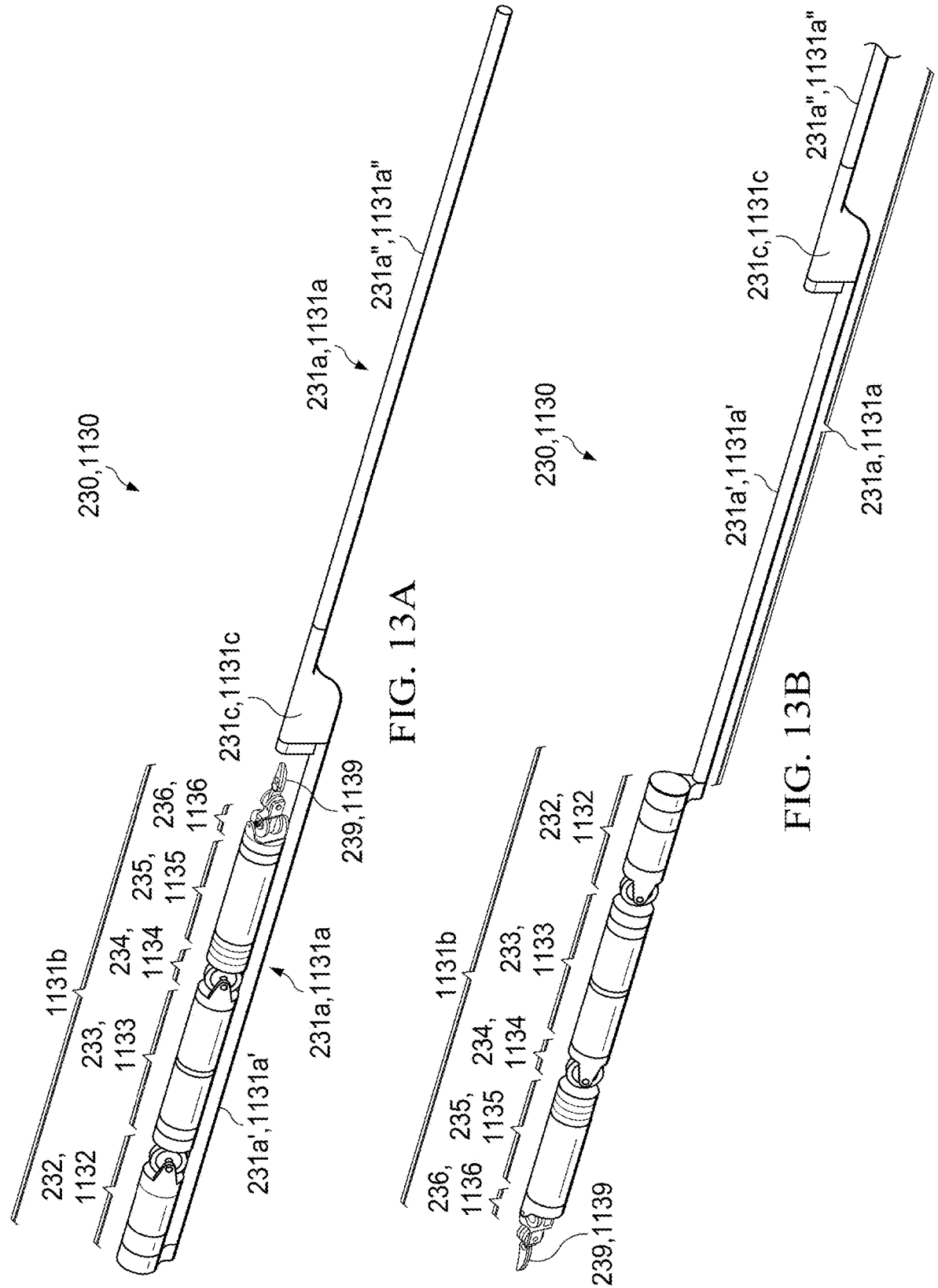

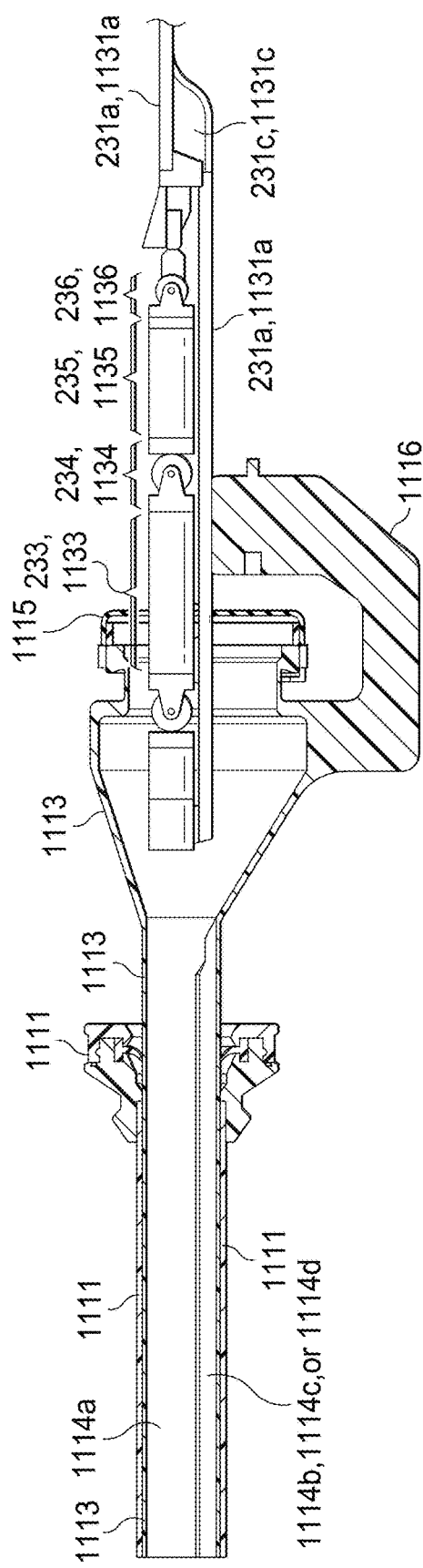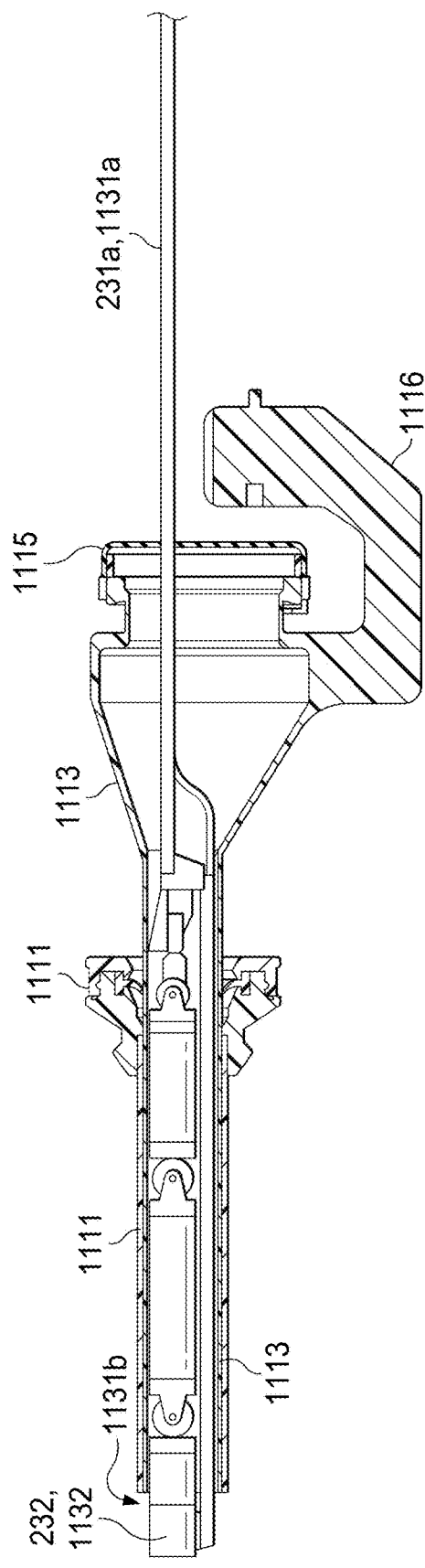
FIG. 15A
FIG. 15B

PORT ASSEMBLY FOR USE WITH ROBOTIC DEVICES AND SYSTEMS TO PERFORM SINGLE INCISION PROCEDURES AND NATURAL ORIFICE TRANSLUMENAL ENDOSCOPIC SURGICAL PROCEDURES

CROSS-REFERENCE TO RELATED APPLICATIONS

This application is a continuation-in-part application of U.S. application Ser. No. 15/662,921, filed on Jul. 28, 2017, which is a divisional application of U.S. application Ser. No. 15/044,889, filed on Feb. 16, 2016, which is a continuation-in-part of U.S. application Ser. No. 14/693,207, filed on Apr. 22, 2015, which claims priority to U.S. Application No. 61/982,717, filed Apr. 22, 2014; a continuation-in part application of U.S. application Ser. No. 15/044,895, filed on Feb. 16, 2016, which is a continuation-in-part of U.S. application Ser. No. 14/693,207, filed on Apr. 22, 2015, which claims priority to U.S. Provisional Application No. 61/982,717, filed on Apr. 22, 2014; and a continuation-in-part application of U.S. application Ser. No. 16/028,982, filed on Jul. 6, 2018, which is a continuation application of U.S. application Ser. No. 15/044,895, filed on Feb. 16, 2016, which is a continuation-in-part of U.S. application Ser. No. 14/693,207, filed on Apr. 22, 2015, which claims priority to U.S. Application No. 61/982,717, filed Apr. 22, 2014; the contents of all of which are hereby expressly incorporated by reference in their entirety, including the contents and teachings of any references contained therein.

BACKGROUND

The present disclosure relates generally to systems, devices, and methods, and more specifically, relates to systems, devices, and methods for use in performing procedures via a single incision or a natural orifice.

Conventional surgical procedures will generally require one or more large incisions to a patient in order for the surgical team to perform a surgical action. With the advancement of medical science and technology, most conventional open surgical procedures have been largely replaced with minimally invasive surgery (MIS) procedures. Recent developments in respect to computer-assisted and/or robotic surgical technology have contributed to advancements in MIS, including the ability to translate a surgeon's desired actions into movements of robotic instruments inside the body cavity of a patient.

BRIEF SUMMARY

Despite recent developments in modern medical science and technology, it is recognized in the present disclosure that one or more problems are encountered in modern surgical technology and methodology. For example, a typical MIS procedure requires multiple incisions to a patient in order to allow access via the incisions for the insertion of a camera and various other laparoscopic instruments into the body cavity of the patient.

As another example, surgical robotic devices oftentimes encounter difficulties during surgical procedures due to insufficient anchoring and/or reactive forces to stabilize against forces that are desired and/or necessary to be applied during surgical actions.

It is also recognized in the present disclosure that surgical robotic systems face difficulties in providing an instrument, such as a cutting or gripping instrument attached to the end of a surgical robotic arm, with access to all or even most parts, areas, and/or quadrants of abdominal cavity of a patient. That is, after the surgical robotic arm is inserted in the abdominal cavity of the patient and ready to perform a surgical action, the instrument attached to the end of the surgical robotic arm is typically limited to access only certain parts, areas, and quadrants of the abdominal cavity of the patient.

In yet another example, known surgical robotic systems typically provide only between one to two surgical robotic arms per access or opening (such as an incision or a natural orifice) of the patient. In this regard, one or more additional incisions will be required for the insertion of a camera and various laparoscopic instruments into the abdominal cavity of the patient.

As another example, while known surgical robotic systems have been designed for use in an abdominal cavity of a patient to perform forward-directed surgical procedures, such systems have not been designed for and may encounter problems when applied in situations requiring reverse-directed surgical procedures. For example, such known surgical robotic systems have not been designed for deployment through a natural orifice, such as a rectum or vagina, for performing natural orifice transluminal endoscopic surgery (or NOTES), such as pelvic gynecological and/or urological procedures. Such systems may encounter one or more problems, such as the inability to access certain organs, tissues, or other surgical sites upon insertion into the natural orifice.

Present example embodiments relate generally to systems, devices, and methods for addressing one or more problems in surgical robotic systems, devices, and methods, including those described above and herein.

In an exemplary embodiment, a surgical system is described. The surgical system may include a first surgical arm assembly, second surgical arm assembly, and a port assembly. The first surgical arm assembly may include a first surgical arm and a first elongated anchor section securable to a first end of the first surgical arm. The first surgical arm may include a serial arrangement of elements or parts, including a first instrument at a second end of the first surgical arm, a first wrist joint, a first distal arm segment, a first elbow joint, a first proximal arm segment, and a first shoulder joint at the first end of the first surgical arm. The second surgical arm assembly may be a separate from the first surgical arm assembly. The second surgical arm assembly may include a second surgical arm and a second elongated anchor section securable to a first end of the second surgical arm. The second surgical arm may include a serial arrangement of elements or parts, including a second instrument at a second end of the second surgical arm, a second wrist joint, a second distal arm segment, a second elbow joint, a second proximal arm segment, and a second shoulder joint at the first end of the second surgical arm. The port assembly may include a first main body and a second main body. The first main body may be an elongated body. The first main body may include proximal and distal ends. The first main body may include a first main channel formed by at least a portion of an interior surface of the elongated body of the first main body. The first main channel may extend between the proximal and distal ends of the first main body. The first main channel may be formed in such a way as to allow both the first and second surgical arms to simultaneously pass through the first main channel. The first main body may include a first anchor channel and second anchor channel. The first and second anchor channels may be formed adjacently to the first main channel. The first main channel and the first and second anchor channels may be collectively formed in such a way as to allow both the first and second elongated anchor sections of the first and second surgical arm assemblies, respectively, to simultaneously pass through the first and second anchor channels, respectively, when the first and second surgical arms are simultaneously provided through the first main channel. The second main body may be an elongated body. The second main body may include proximal and distal ends. The second main body may include a second main channel formed between the proximal and distal ends of the second main body. The second main channel may be formed in such a way as to house at least a portion of the first main body in a hermetically sealable manner.

In another exemplary embodiment, a surgical system is described. The surgical system may include a first surgical arm assembly, a second surgical arm assembly, and a port assembly. The first surgical arm assembly may include a first surgical arm and a first elongated anchor section securable to a first end of the first surgical arm. The first surgical arm may include a serial arrangement of elements or parts, including a first instrument at a second end of the first surgical arm, a first wrist joint, a first distal arm segment, a first elbow joint, a first proximal arm segment, and a first shoulder joint at the first end of the first surgical arm. The second surgical arm assembly may be separate from the first surgical arm assembly. The second surgical arm assembly may include a second surgical arm and a second elongated anchor section securable to a first end of the second surgical arm. The second surgical arm may include a serial arrangement of a second instrument at a second end of the second surgical arm, a second wrist joint, a second distal arm segment, a second elbow joint, a second proximal arm segment, and a second shoulder joint at the first end of the second surgical arm. The port assembly may include an elongated body having proximal and distal ends. The port assembly may also include a main channel formed by at least a portion of an interior surface of the elongated body of the port assembly. The main channel may extend between the proximal and distal ends of the elongated body of the port assembly. The main channel may be formed in such a way as to allow both the first and second surgical arms to simultaneously pass through the main channel. The port assembly may include a first anchor channel and second anchor channel. The first and second anchor channels may be formed adjacently to the main channel. The main channel and the first and second anchor channels may be collectively formed in such a way as to allow both the first and second elongated anchor sections of the first and second surgical arm assemblies, respectively, to simultaneously pass through the first and second anchor channels, respectively, when the first and second surgical arms are simultaneously provided through the main channel.

In another exemplary embodiment, a port assembly is described. The port assembly may be for use with a surgical arm assembly having a surgical arm and an elongated anchor section secured to the surgical arm. The port assembly may include a first main body. The first main body may include an elongated body with proximal and distal ends. The first main body may also include a main channel. The main channel may be formed by at least a portion of an interior surface of the elongated body. The main channel may extend between the proximal and distal ends of the elongated body of the first main body. The first main body may also include an instrument gate. The instrument gate may be secured at a proximal end of the main channel. The instrument gate may include a first expandable opening. The first expandable opening of the instrument gate may be configured to be in a persistently closed position. The first expandable opening may be configurable to adaptively expand to a shape of a cross-section of an instrument, element, or surgical arm assembly (or part thereof). For example, the first expandable opening may be configurable to adaptively expand to a shape of a cross-section of a surgical arm when the surgical arm is inserted through the first expandable opening.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 5A is an illustration of a side view of an example embodiment of an instrument arm assembly;

FIG. 5B is another illustration of a side view of an example embodiment of an instrument arm assembly;

FIG. 12D is an illustration of a perspective view of another example embodiment of the image capturing retractor;

FIG. 12E is an illustration of a perspective view of another example embodiment of the image capturing retractor;

FIG. 13A is an illustration of a perspective view of an example embodiment of the surgical arm assembly in the reverse configuration;

FIG. 13B is an illustration of a perspective view of an example embodiment of the surgical arm assembly in the forward configuration;

FIG. 15A is an illustration of a cross-sectional view of an example embodiment of the port assembly with a surgical arm assembly being inserted into the proximal end of the first main body of the port assembly; and FIG. 15B is an illustration of a cross-sectional view of an example embodiment of the port assembly with a surgical arm assembly being inserted through the port assembly.

Although similar reference numbers may be used to refer to similar elements in the figures for convenience, it can be appreciated that each of the various example embodiments may be considered to be distinct variations.

DETAILED DESCRIPTION

Figure 1A:
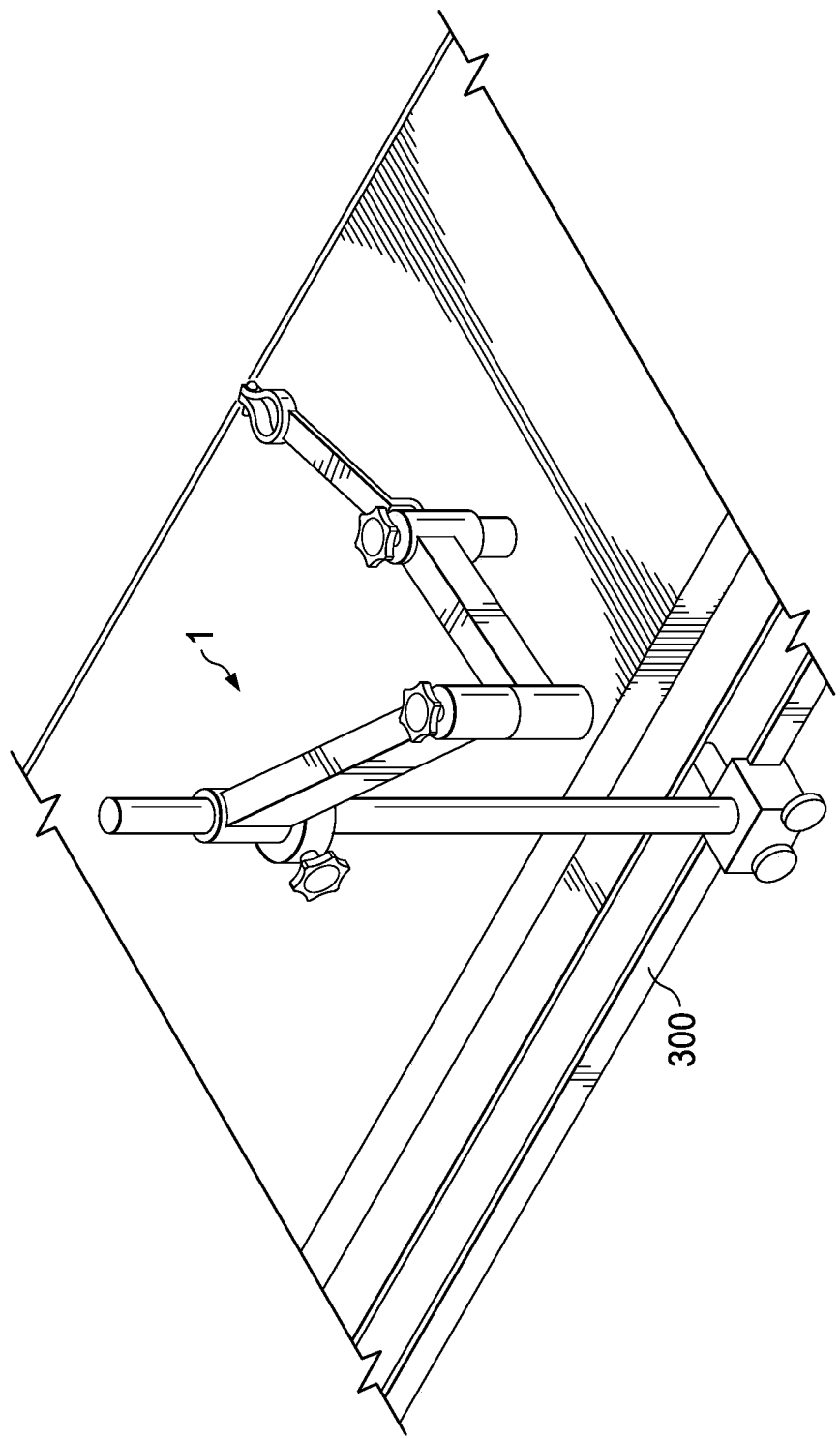
FIG. 1A is illustration of a perspective view of an example embodiment of an external anchor.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

It is recognized in the present disclosure that, despite recent developments in medical science and technology, one or more problems are encountered in modern surgical technology and methodology, including MIS. For example, a typical MIS procedure requires multiple incisions to a patient in order to allow access via the incisions for the insertion of a camera and various other laparoscopic instruments into the body cavity of the patient.

In addition to the aforementioned disadvantages pertaining to the multiple and rather large incisions, it is recognized in the present disclosure that surgical robotic systems, including surgical robotic arms (and those instruments attached to them), developed for performing robotic-assisted MIS surgical procedures also suffer from one or more problems. For example, it is recognized herein that a major technical challenge for a surgical robotic system is the difficulty in providing sufficient anchoring and/or reactive forces to stabilize against forces that are desired and/or necessary to be applied to the patient by the surgical robotic system during a surgical action. In this regard, certain surgical actions for known surgical robotic systems may require tremendous effort and time, and may not be performed properly or at all as a result of the problem of insufficient anchoring and/or reactive forces.

Another example of a problem recognized in the present disclosure as being encountered by surgical robotic systems is the difficulty in providing an instrument, such as a cutting and/or gripping instrument attached to the end of a surgical robotic arm, with access to all or even most parts, areas, and quadrants of an abdominal cavity of a patient after the surgical robotic system has been set up (or installed) and is ready to perform a surgery. That is, after the surgical robotic arm of the system has been inserted, attached, and properly set up in the abdominal cavity of the patient and is ready to perform a surgical action, the instrument attached to the end of the surgical robotic arm is typically limited to access only certain parts, areas, and quadrants of the abdominal cavity of the patient. It is recognized in the present disclosure that such problems result in large from the limited number of possible degrees of freedom that can be provided by known surgical robotic systems and arms, and more specifically, the limited number of in vivo degrees of freedom (i.e. the degrees of freedom provided within an abdominal cavity of a patient) of known surgical robotic systems and arms. In this regard, surgical robotic systems typically provide only between 2 to 4 in vivo degrees of freedom for each surgical robotic arm.

As another example, while known surgical robotic systems have been designed for use in an abdominal cavity of a patient to perform forward-directed surgical procedures, such systems have not been designed for and may encounter problems when applied in situations requiring reverse-directed surgical procedures. For example, such known surgical robotic systems have not been designed for deployment through a natural orifice, such as a rectum or vagina, for performing natural orifice transluminal endoscopic surgery (or NOTES), such as trans-vaginal gynecological procedures in women and trans-rectal urological procedures in men. Such systems may encounter one or more problems, such as the inability to access certain organs, tissues, or other surgical sites upon insertion into the natural orifice.

Surgical systems, devices, and methods, including those for use in MIS and natural orifice transluminal endoscopic surgery (or NOTES), are described in the present disclosure for addressing one or more problems of known surgical systems, devices, and methods, including those described above and in the present disclosure. It is to be understood that the principles described in the present disclosure can be applied outside of the context of MIS and/or NOTES, such as performing scientific experiments and/or procedures in environments that are not readily accessible by humans, including in a vacuum, in outer space, and/or under toxic and/or dangerous conditions, without departing from the teachings of the present disclosure.

The Surgical System (e.g., Surgical Device 200)

Figure 2A:
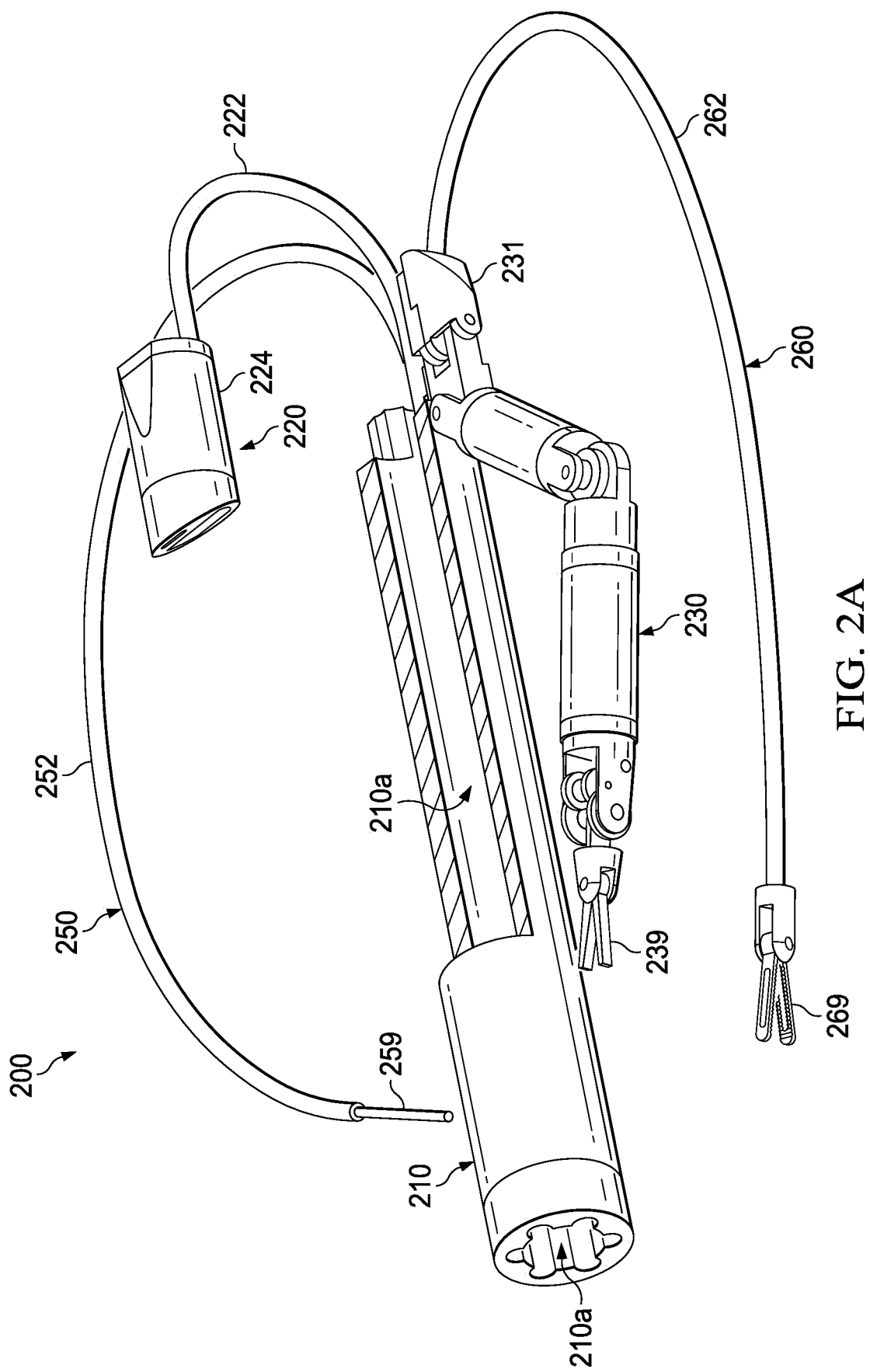
FIG. 2A is an illustration of a perspective view of an example embodiment of a surgical device configured in a reverse-directed position with one port assembly, one instrument arm assembly, and one image capturing assembly.
Figure 2B:
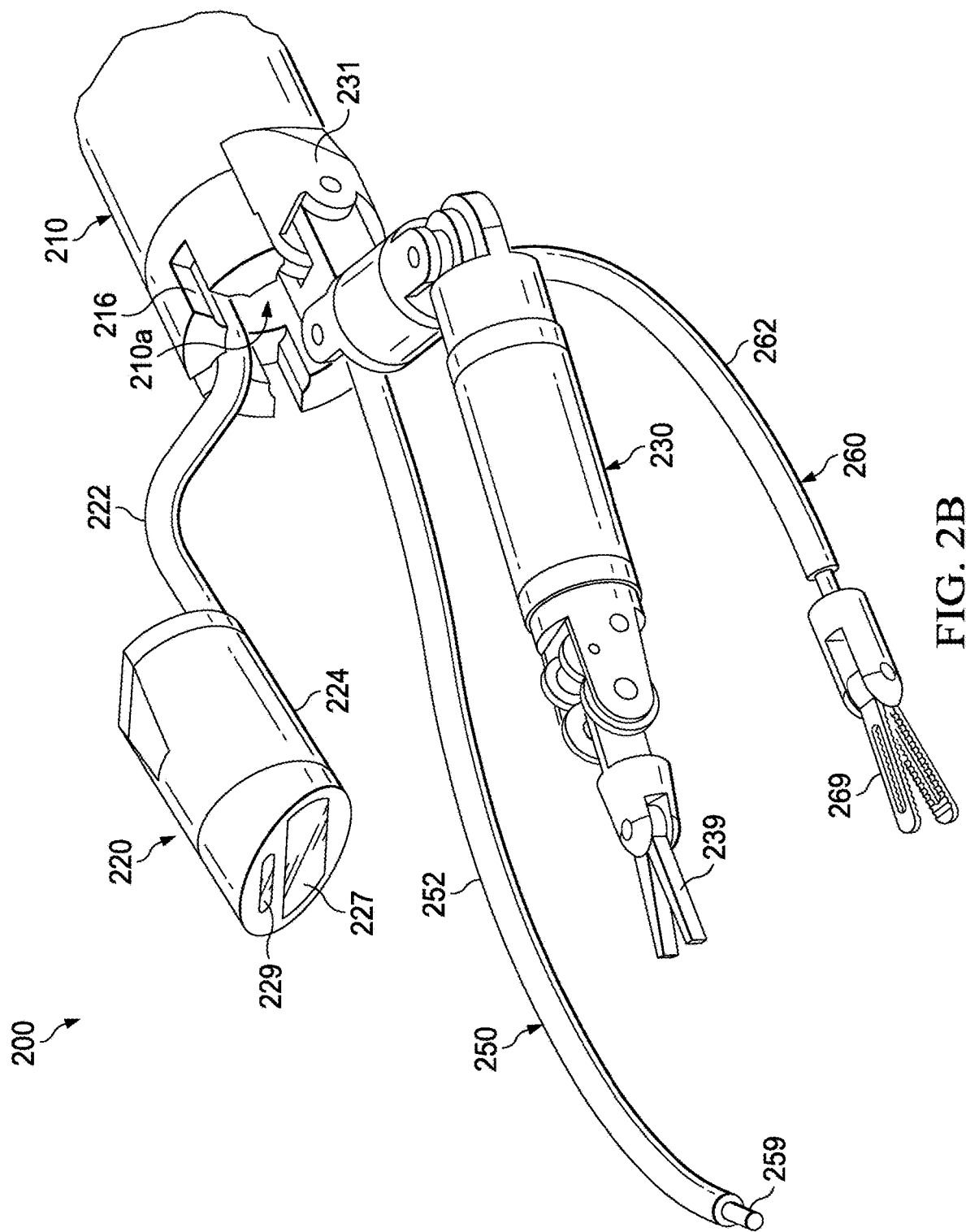
FIG. 2B is an illustration of a perspective view of an example embodiment of a surgical device configured in a forward-directed position with one port assembly, one instrument arm assembly, and one image capturing assembly.

An illustration of an example embodiment of a surgical device or system (e.g., surgical device or system 200) operable to be inserted into an abdominal cavity of a patient through a single access or opening (e.g., a single incision (such as an incision in or around the umbilical area) or through a natural orifice (such as a rectum or vagina, for performing natural orifice transluminal endoscopic surgery (or NOTES), hereinafter referred to as an "opening") of the patient is depicted in FIG. 2A and FIG. 2B. The surgical device may then be anchored so as to position the surgical device 200 in the opening. The surgical device 200 may comprise a port assembly 210 and an instrument arm assembly 230. The surgical device 200 may also comprise other elements, such as one or more other instrument arm assemblies, one or more image capturing assemblies, one or more assistant arm assemblies, etc.

Figure 1B:
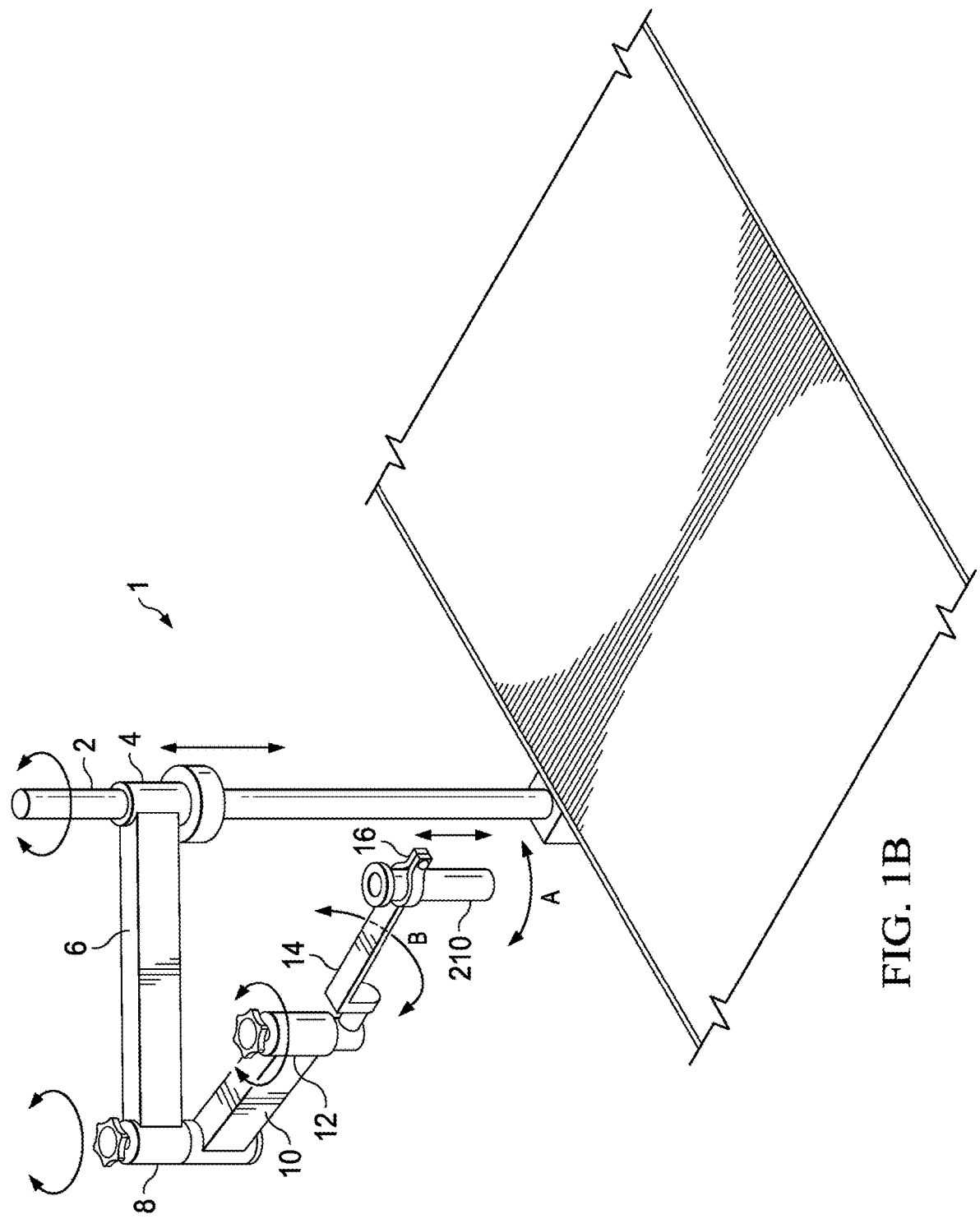
FIG. 1B is another illustration of a perspective view of an example embodiment of an external anchor attached to an example embodiment of a port assembly.
Figure 10A:
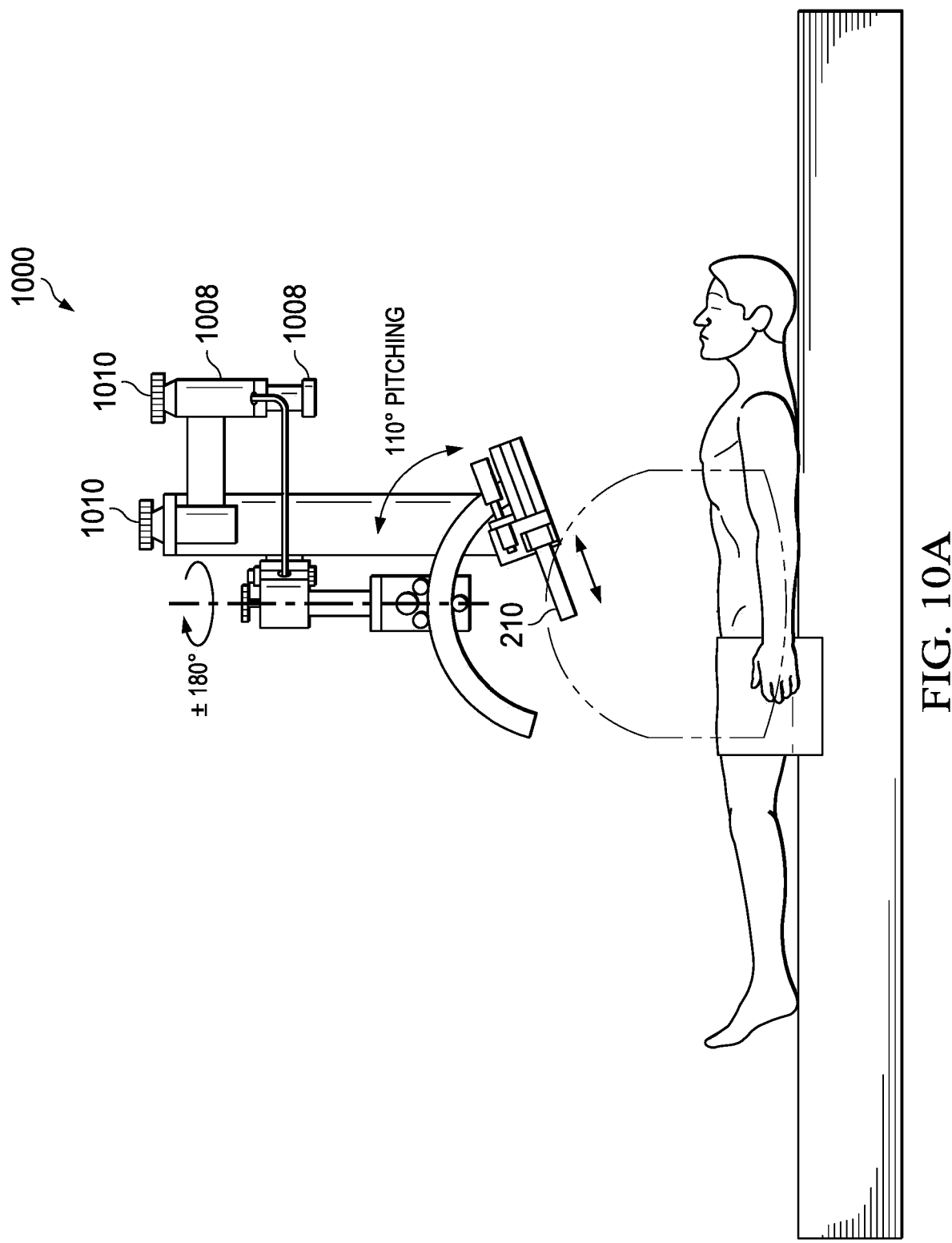
FIG. 10A is an illustration of a perspective view of an example embodiment of an external anchor.
Figure 10B:
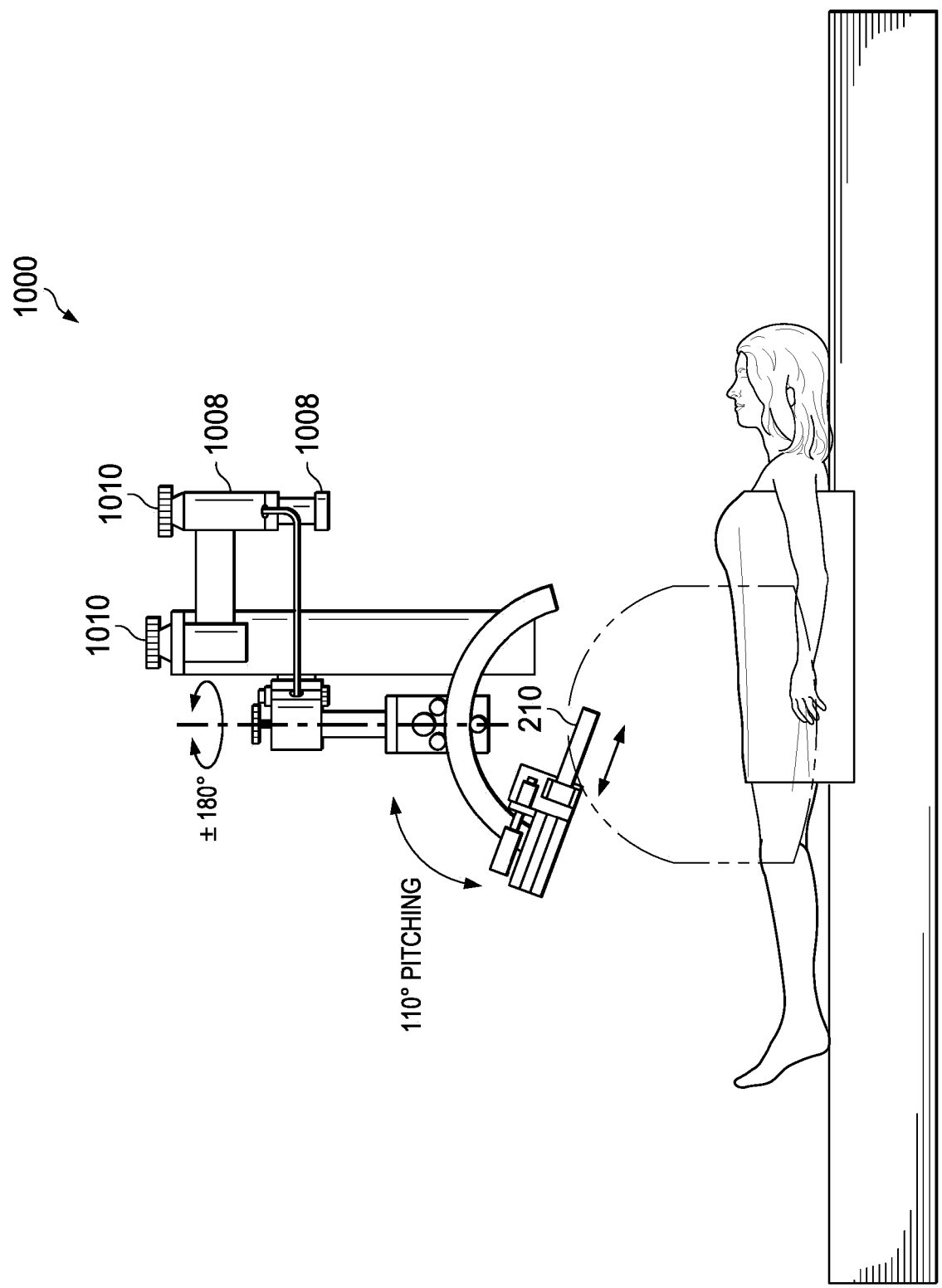
FIG. 10B is an illustration of a perspective view of another example embodiment of an external anchor.

As illustrated in FIG. 1A and FIG. 1B, the surgical device 200 may be provided with an external anchor 1 attachable to the port assembly 210. The external anchor 1 may comprise a configurable assembly of segments 2, 6, 10, and 14 in communication with one another via joints or connecting portions 4, 8, and 12, and external anchor connector 16. The external anchor 1 may be operable to securely fix the position and/or orientation (hereinafter "position") of the port assembly 210 in or about the single opening of the patient, and may also be operable to provide sufficient anchoring and/or reactive forces to stabilize against forces desired and/or necessary to be applied by at least one or more elements of the surgical device 200, including the instrument arm assembly 230, during a surgical action or procedure. The external anchor 1, which may also be in the form of the controllable swivel assembly 1000 illustrated in FIG. 10A and FIG. 10B, may be operable to cooperate with the port assembly 210 to provide one or more in vitro degrees of freedom. For example, the external anchor 1 may be configurable to provide 3 in vitro degrees of freedom. In example embodiments, the one or more in vitro degrees of freedom may include a torsional movement, pivotal movement, telescopic movement, and/or other movements of the port assembly 210 relative to the external anchor 1. For example, a torsional movement of the port assembly 210, as illustrated by arrow A in FIG. 1B, may allow one or more attached instruments, including an instrument arm assembly 230, to re-position during a surgical procedure (i.e. after set up or installation) so as to access other parts, areas, and/or all quadrants of the abdominal cavity of the patient. As another example, a pivotal movement of the port assembly 210, as illustrated by arrow B in FIG. 1B, may allow the port assembly 210 to be positioned in one of a plurality of angles with respect to opening of the patient, and may also allow attached instruments, including the instrument arm assembly 230, to re-position during a surgical procedure (i.e. after set up or installation) so as to access distal areas of the abdominal cavity of the patient. The other joint portions of the external anchor 1 may also be operable to cooperate and/or assist in desired movements of the port assembly 210. The external anchor 1 may be anchored to one or more stationary or fixedly positioned objects, such as a side rail 300 of a surgical table/bed illustrated in FIG. 1A. FIGS. 10A and 10B illustrate other example movements that provide for additional in vitro degrees of freedom via an example embodiment of the external anchor (controllable swivel assembly) 1000. The controllable swivel assembly 1000 will be further described below in at least the section "(1) Providing the external anchor and installing the port assembly."

Figure 3A:
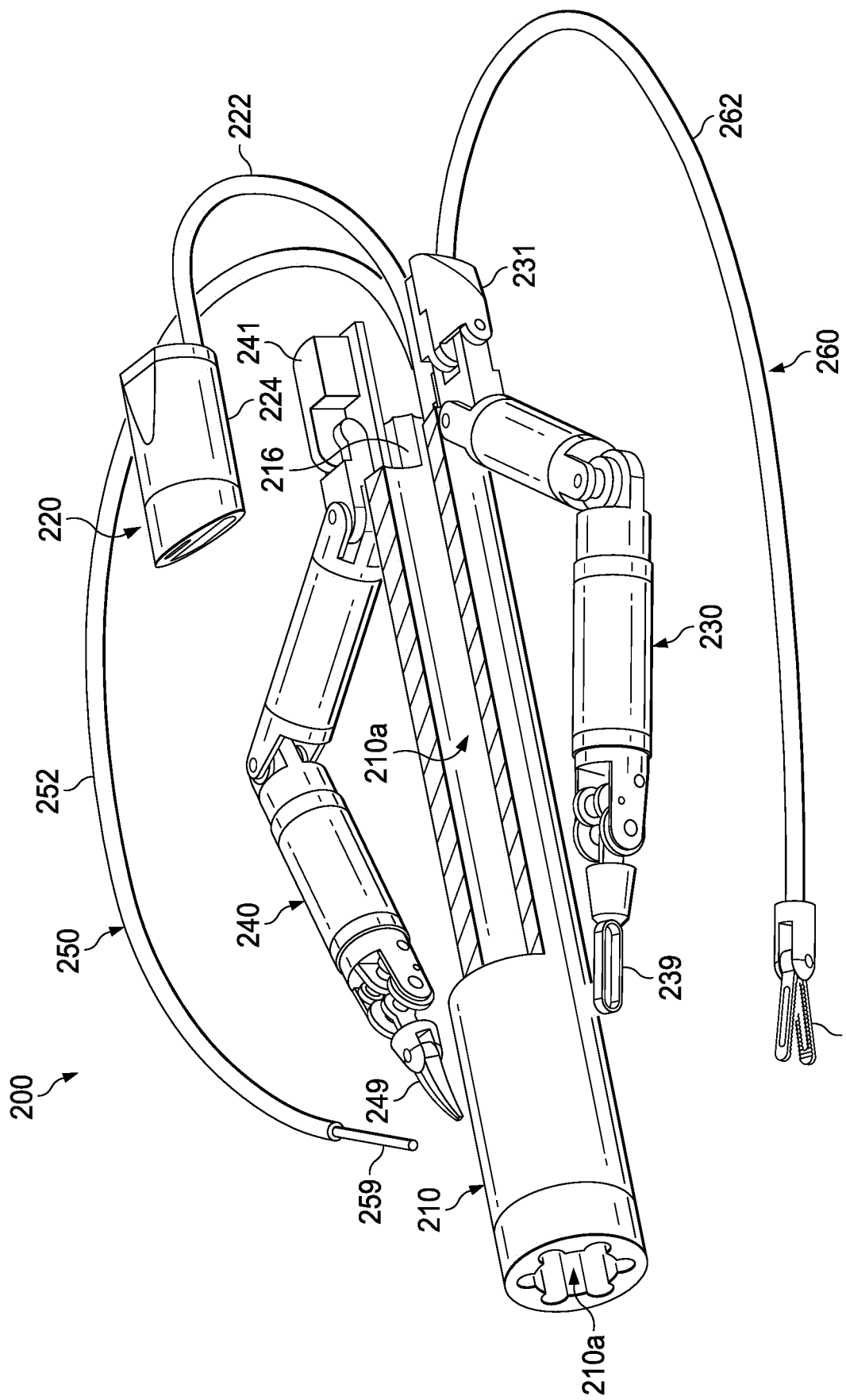
FIG. 3A is another illustration of a perspective view of another example embodiment of a surgical device configured in a reverse-directed position with one port assembly, one instrument arm assembly, and one image capturing assembly.
Figure 3B:
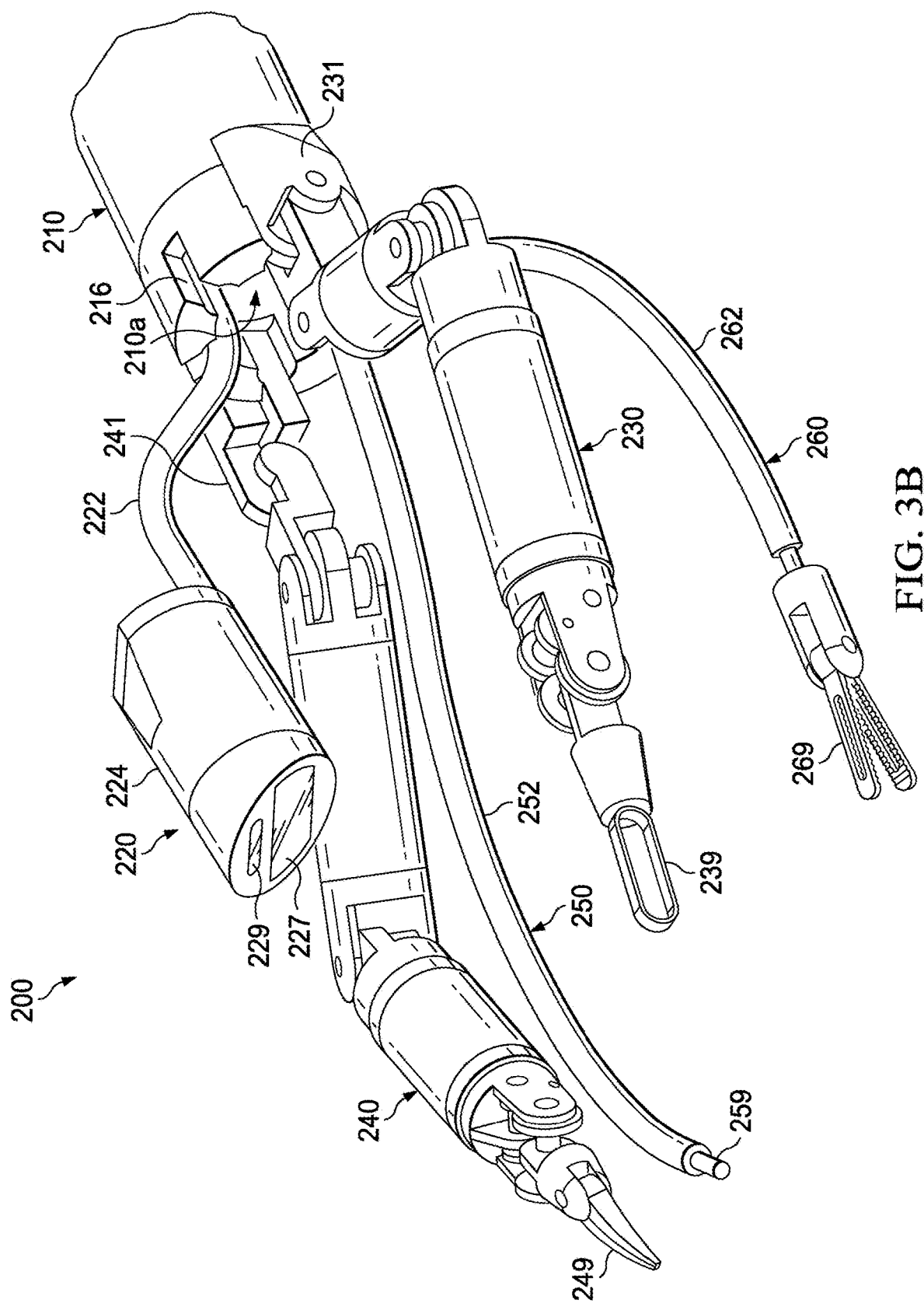
FIG. 3B is another illustration of a perspective view of another example embodiment of a surgical device configured in a forward-directed position with one port assembly, one instrument arm assembly, and one image capturing assembly.

The surgical device 200 may further comprise one or more additional instrument arm assemblies, such as a second instrument arm assembly 240 illustrated in FIGS. 3A and 3B, attachable to the port assembly 210. One or more of the instrument arm assemblies, including the first instrument arm assembly 230, the second instrument arm assembly 240, a third instrument arm assembly (not shown), a fourth instrument arm assembly (not shown), etc., may be attachable or securable to the port assembly 210. Such instrument arm assemblies may be operable to access and perform one or more surgical actions in/on any and all parts, areas, and/or quadrants within a cavity of the patient. For example, surgical device 200 may be configurable to perform surgical actions in a forward direction (or "forward-directed position" or "forward position") (e.g., as illustrated in FIGS. 2B and 3B). As another example, surgical device 200 may be configurable to perform surgical actions in a reverse direction (or "reverse-directed position" or "reverse position") (e.g., as illustrated in FIGS. 2A and 3A).

The surgical device 200 may also comprise one or more image capturing assemblies, such as image capturing assembly 220. The surgical device 200 may further comprise one or more assistant arm assemblies, such as a retractor arm assembly 250, as illustrated in FIGS. 2A, 2B, 3A, and 3B. Furthermore, the surgical device 200 may comprise one or more other instrument arm assemblies, such as suction/irrigation assembly 260, illustrated in FIGS. 2A, 2B, 3A, and 3B, that can be inserted into the opening of the patient via the port assembly 210 before, during, and/or after performing a surgical action or procedure. It is to be understood in the present disclosure that the surgical device 200 may be configurable in a plurality of configurations and arrangements, including having more or less than two instrument arm assemblies (such as third, fourth, fifth, etc. instrument arm assemblies), more than one image capturing assembly (such as second, third, etc. image capturing assemblies), more or less than one assistant arm assembly (such as second, third, etc. assistant arm assemblies), and/or more or less than one other laparoscopic tool in example embodiments without departing from the teachings of the present disclosure.

The Port Assembly (e.g., Port Assembly 210)

An example embodiment of the port assembly (e.g., port assembly 210) is illustrated in FIGS. 2A, 2B, 3A, 3B, FIG. 4A, FIG. 4B, FIG. 4C, and FIG. 4D. The port assembly 210 may be configurable to be inserted in or about a single opening of the patient (such as a single incision or a natural orifice) and fixed in position by at least the external anchor (such as the external anchor 1 illustrated in FIGS. 1A and 1B and the controllable swivel assembly 1000 illustrated in FIGS. 10A and 10B).

Figure 4A:
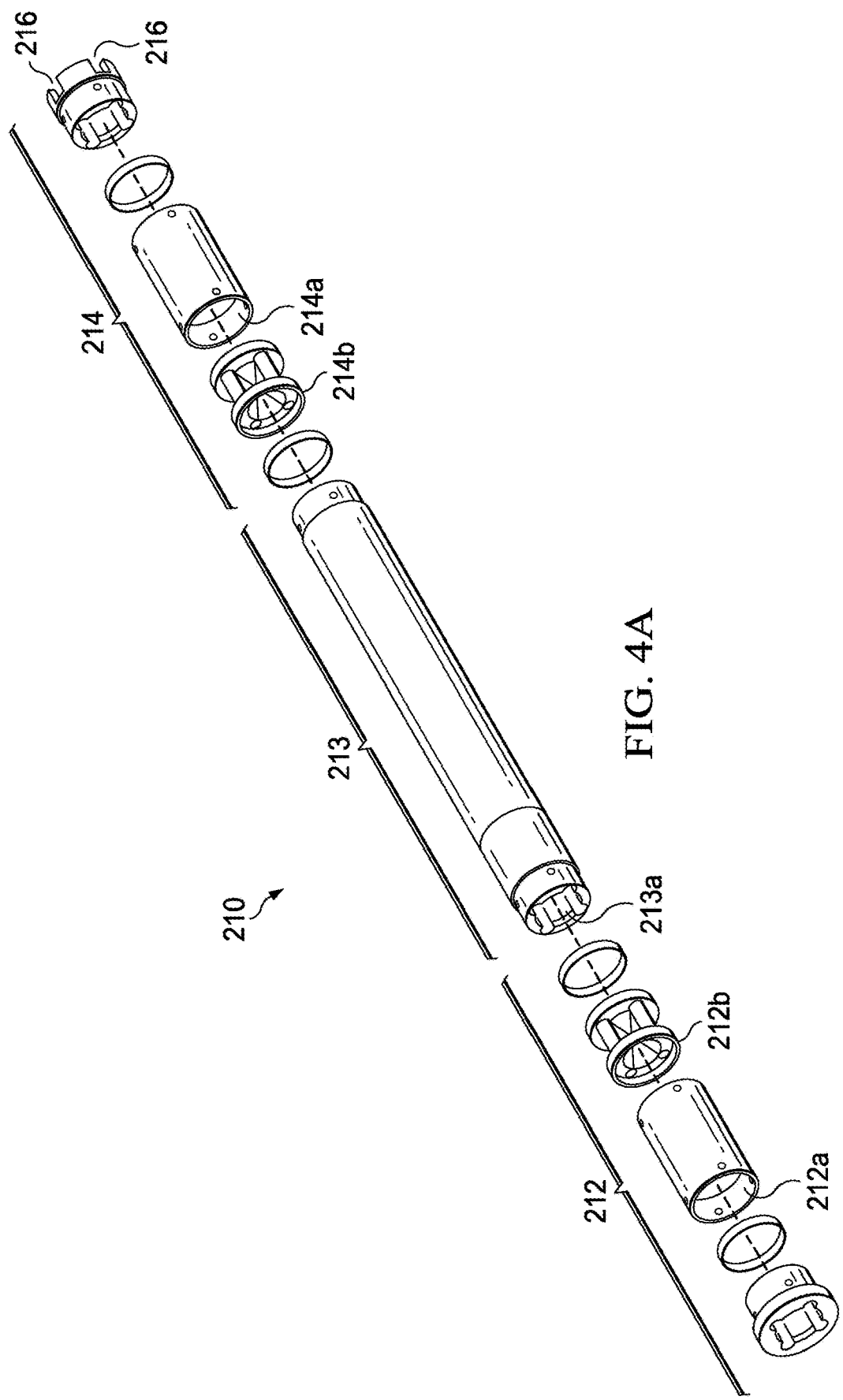
FIG. 4A is an illustration of a perspective exploded view of an example embodiment of a port assembly.
Figures 4B, 4C, 4D:
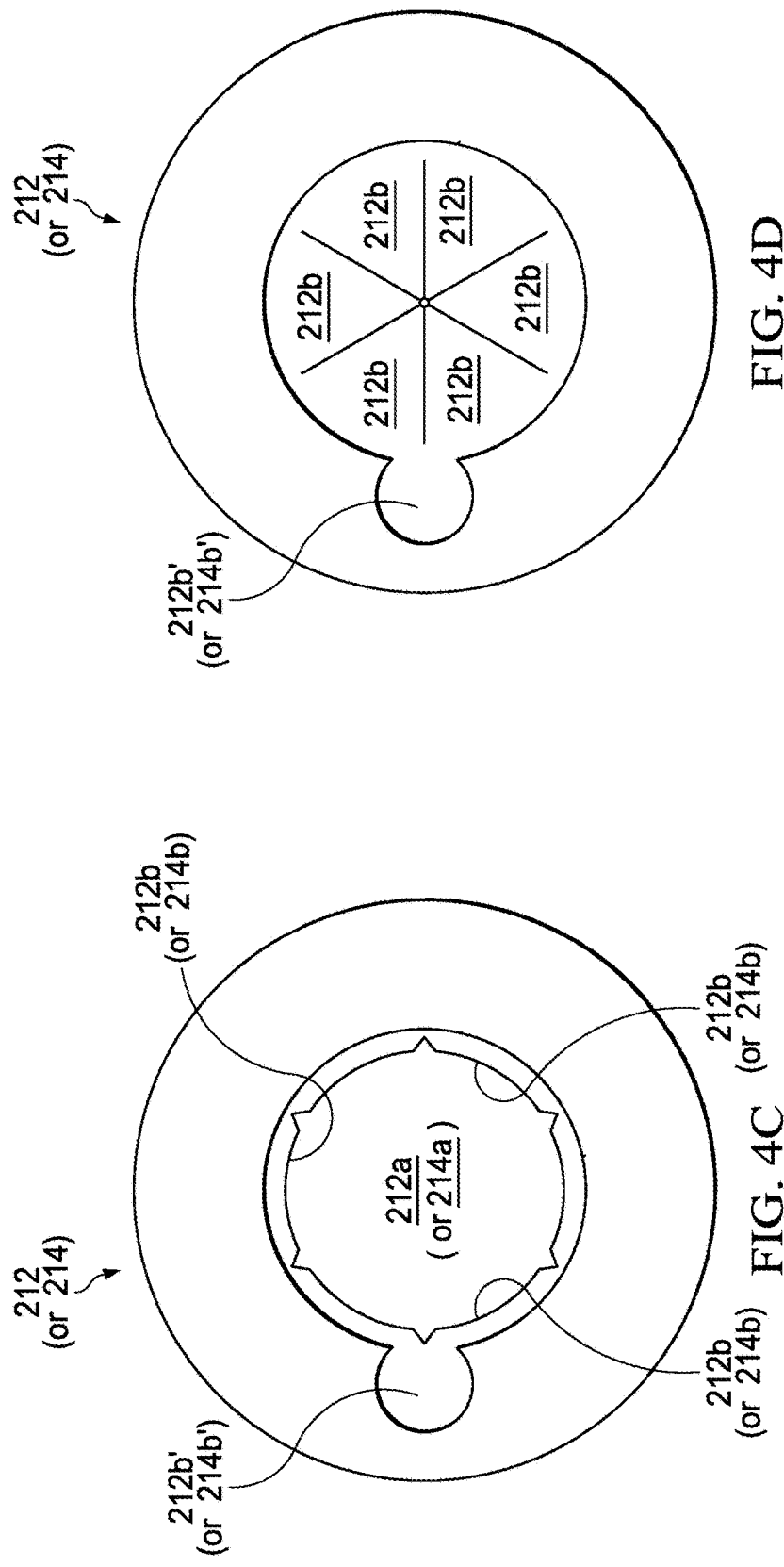
FIG. 4B is an illustration of a side view of an example embodiment of a port assembly.
FIG. 4C is an illustration of a cross-sectional view of an example embodiment of a port assembly with a first or second gate assembly in the open position.
FIG. 4D is an illustration of a cross-sectional view of an example embodiment of a port assembly with a first or second gate assembly in the closed position.

The port assembly 210 may be an elongated structure having a central access channel 210a formed through the port assembly 210. The central access channel 210a may be for use in inserting and removing instruments, such as one or more instrument arm assemblies 230, 240, one or more image capturing assemblies 220, one or more assistant arm assemblies 250, 260, etc. In an example embodiment, the port assembly 210 may include a first end section 212 and a second end section 214. The first end section 212 and second end section 214 may be fixably attachable to one another or formed as a unitary article. The port assembly 210 may also include a mid section 213 between the first end section 212 and the second end section 214. The first end section 212, second end section 214, and mid section 213 may be fixably attachable to one another, as illustrated in FIGS. 4A and 4B, or two or more of these sections may be formed as a unitary article. In an example embodiment, the first end section 212 may be the portion of the port assembly 210 that is secured to the external anchor 1, and the port assembly 210 may be fixed in position at an angle θ relative to the singe opening of the patient of between about 0 to +/−90 degrees. These and other elements of the port assembly 210 will now be described below and with reference to FIGS. 2A, 2B, 3A, 3B, and 4A-D.

As illustrated in at least FIGS. 4A and 4B, the port assembly 210 may comprise a first end section 212. The first end section 212 may have a first end channel 212a formed through the first end section 212. The first end channel 212a may be considered as a part of the central access channel 210a. The first end section 212 may also include a portion operable to be secured to the external anchor 1, such as a portion on an exterior portion of the first end section 212.

The first end section 212 may also include a first gate assembly 212b, as illustrated in FIGS. 4A, 4C, and 4D. The first gate assembly 212 may be configurable to control access through the first end channel 212a. For example, the first gate assembly 212b may be configurable to be in an open position, as illustrated in FIG. 4C, so as to allow access through the first end channel 212a. The first gate assembly 212b may also be configurable to be in a closed position, as illustrated in FIG. 4D, so as to prevent or restrict access through the first end channel 212a. The first gate assembly 212b may also be configurable to be in a partially closed (or partially opened) position (not shown). The first gate assembly 212b may also be configurable to transition between the closed position and the open position.

In an example embodiment, the first gate assembly 212b may be provided within the first end section 212 in such a way that, when the first gate assembly 212b is configured to be in the open position, as illustrated in FIG. 4C, the first end channel 212a is substantially or completely unobstructed by the first gate assembly 212b. The first gate assembly 212b may be configured to be in the open position when a surgeon desires to insert (or remove) an instrument into (or out of) the cavity of the patient via the first end channel 212a (and the rest of the central access channel 210a).

Similarly, the first gate assembly 212b may be provided within the first end section 212 in such a way that, when the first gate assembly 212b is configured to be in the closed position, as illustrated in FIG. 4D, the first end channel 212a is substantially or completely obstructed by the first gate assembly 212b. The first gate assembly 212b may be configured to be in the closed position when a surgeon desires to maintain an insufflation of the cavity of the patient and/or when the surgeon does not need to insert (or remove) an instrument into (or out of) the cavity of the patient via the first end channel 212a.

The first gate assembly 212b may include a first expandable portion 212b configurable to expand when the first gate assembly 212b is configured to the closed position, as illustrated in FIG. 4D. When the first gate assembly 212b is configured to the closed position, the first expandable portion 212b may be operable to substantially or completely block, among other things, a gas medium (and/or other medium) from passing through the first end channel 212a. For example, if the cavity of the patient is being insufflated using a gas, such as carbon dioxide ($CO_2$), the first gate assembly 212b (i.e., the first expandable portion 212b) may be configurable to substantially prevent the carbon dioxide gas from leaving the cavity of the patient through the first end channel 212a.

The first expandable portion 212b may include one or more first expandable members. For example, the first expandable portion 212b may include six expandable members, as illustrated in FIGS. 4C and 4D. It is to be understood that the first expandable portion 212b may include more or less than six expandable members without departing from the teachings of the present disclosure. Some or all of the first expandable members may be integrated together and/or in communication with one another, such as in a manner where some or all of the first expandable members are operable to receive pressure (i.e., gas medium) from a common or same first source 212b'. For example, when the first gate assembly 212b is configured to the closed position, the first source 212b' may be configurable to provide a positive pressure (i.e., a supply of gas) so as to cause some or all of the first expandable members to expand and block the first end channel 212a (e.g., hermetically block the first end channel 212a). Similarly, when the first gate assembly 212b is configured to the open position, the first source 212b' may be configurable to provide a negative pressure (i.e., remove gas) so as to cause one or more (or all) of the first expandable members to not expand (and/or contract) and unblock the first end channel 212a. It is to be understood that more than one first sources 212b' may provide the positive pressure and negative pressure to the one or more expandable members without departing from the teachings of the present disclosure.

It is recognized in the present disclosure that the first gate assembly 212b may also include a valve (not shown), or the like, in addition to or in replacement of the first expandable portion 212b. The valve may be configurable to perform substantially the same actions of blocking the first end channel 212a when the first gate assembly 212b is configured to the closed position and unblocking the first end channel 212a when the first gate assembly 212b is configured to the open position. The valve may be any type of valve configurable to perform the actions described above and in the present disclosure. The valve may include, but is not limited to including, a ball valve, gate valve, etc., so long as the valve is configurable to substantially block/unblock the first end channel 212a and prevent a gas medium from passing through the first end channel 212a.

The port assembly 210 may also include the second end section 214, as illustrated in at least FIGS. 4A and 4B. The second end section 214 may have a second end channel 214a formed through the second end section 214. The second end channel 214a may be substantially or completely aligned with the first end channel 212a. The second end channel 214a, as well as the first end channel 212a, may be considered as a part of the central access channel 210a in example embodiments. The second end section 214 may also include an insufflation port (not shown) for use in providing insufflation to the cavity of the patient.

The second end section 214 may also include a second gate assembly 214, as illustrated in FIGS. 4A, 4C, and 4D. The second gate assembly 214 may be configurable to control access through the second end channel 214a. For example, the second gate assembly 214b may be configurable to be in an open position, as illustrated in FIG. 4C, so as to allow access through the second end channel 214a. The second gate assembly 214b may also be configurable to be in a closed position, as illustrated in FIG. 4D, so as to prevent or restrict access through the second end channel 214a. The second gate assembly 214b may also be configurable to be in a partially closed (or partially opened) position (not shown). The second gate assembly 214b may also be configurable to transition between the closed position and the open position.

In an example embodiment, the second gate assembly 214b may be provided within the second end section 212 in such a way that, when the second gate assembly 214b is configured to be in the open position, as illustrated in FIG. 4C, the second end channel 214a is substantially or completely unobstructed by the second gate assembly 214b. The second gate assembly 214b may be configured to be in the open position when a surgeon desires to insert (or remove) an instrument into (or out of) the cavity of the patient via the second end channel 214a (and the rest of the central access channel 210a).

Similarly, the second gate assembly 214b may be provided within the second end section 214 in such a way that, when the second gate assembly 214b is configured to be in the closed position, as illustrated in FIG. 4D, the second end channel 214a is substantially or completely obstructed by the second gate assembly 214b. The second gate assembly 214b may be configured to be in the closed position when a surgeon desires to maintain an insufflation of the cavity of the patient and/or when the surgeon does not need to insert (or remove) an instrument into (or out of) the cavity of the patient via the second end channel 214a.

The second gate assembly 214b may include a second expandable portion 214b configurable to expand when the second gate assembly 214b is configured to the closed position, as illustrated in FIG. 4D. When the second gate assembly 214b is configured to the closed position, the second expandable portion 214b may be operable to substantially or completely block, among other things, a gas medium (and/or other medium) from passing through the second end channel 214a. For example, if the cavity of the patient is being insufflated using a gas, such as carbon dioxide ($CO_2$), the second gate assembly 214b (i.e., the second expandable portion 214b) may be configurable to substantially prevent the carbon dioxide gas from leaving the cavity of the patient through the second end channel 214a.

The second expandable portion 214b may include one or more second expandable members. For example, the second expandable portion may include six expandable members, as illustrated in FIGS. 4C and 4D. It is to be understood that the second expandable portion 214b may include more or less than six expandable members without departing from the teachings of the present disclosure. Some or all of the second expandable members may be integrated together and/or in communication with one another, such as in a manner where some or all of the second expandable members are operable to receive pressure (i.e., gas medium) from a common or same second source 214b'. For example, when the second gate assembly 214b is configured to the closed position, the second source 214b' may be configurable to provide a positive pressure (i.e., a supply of gas) so as to cause some or all of the second expandable members to expand and block the second end channel 214a (e.g., hermetically block the second end channel 214a). Similarly, when the second gate assembly 214b is configured to the open position, the second source 214b' may be configurable to provide a negative pressure (i.e., remove gas) so as to cause some or all of the second expandable members to not expand (and/or contract) and unblock the second end channel 214a. It is to be understood that more than one second sources 214b' may provide the positive pressure and negative pressure to the one or more expandable members without departing from the teachings of the present disclosure. It is also to be understood in the present disclosure that one or more of the first sources 212b' and one or more of the second sources 214b' may be the same or different sources.

It is recognized in the present disclosure that the second gate assembly 214b may also include a valve (not shown), or the like, in addition to or in replacement of the second expandable portion 214b. The valve may be configurable to perform substantially the same actions of blocking the second end channel 214a when the second gate assembly 214b is configured to the closed position and unblocking the second end channel 214a when the second gate assembly 214b is configured to the open position. The valve may be any type of valve configurable to perform the actions described above and in the present disclosure. The valve may include, but is not limited to including, a ball valve, gate valve, etc., so long as the valve is configurable to substantially block/unblock the second end channel 214a and prevent a gas medium from passing through the second end channel 214a.

The second end section 214 may also include one or more anchor ports 216, as illustrated in FIGS. 4A and 4B. Each of the anchor ports 216 may be operable to enable an instrument arm assembly 230 or 240, image capturing assembly 220, and/or assistant arm assemblies 250 or 260 to be secured to and unsecured from the port assembly 210. Each of the anchor ports 216 may be formed in any one or more of a plurality of shapes, holes, slots, indentations, protrusions, hooks, fasteners, magnets, buckles, or the like, including those described above and in the present disclosure. For example, as illustrated in FIGS. 4A and 4B, one or more of the anchor ports 216 may include one or more slots, or the like, operable to allow a shoulder section 231 of an instrument arm assembly 230 or 240 to be inserted into and attached.

In example embodiments, the port assembly 210 may also include the mid section 213, as illustrated in at least FIGS. 4A and 4B. The mid section 213 may have a mid section channel 213a formed through the mid section 213. The mid section channel 213a may be substantially or completely aligned with the first end channel 212a and/or the second end channel 214a. In this regard, the mid section channel 213a, as well as the first end channel 212a and/or the second end channel 214a, may be considered as a part of the central access channel 210a in example embodiments. The mid section 213 may also include an insufflation port (not shown) in addition to or in replacement of the insufflation port (not shown) of the second end section 214. In some example embodiments, the mid section 213 may also include a mid section gate assembly (not shown) similar to that of the first gate assembly 212 and second gate assembly 214 described above and in the present disclosure.

In example embodiments, the mid section channel 213a may be operable to cooperate with the first gate assembly 212b and the second gate assembly 214b to function as or like an isolation chamber for instruments, such as the instrument arm assembly 230 or 240, image capturing assembly 220, assistant arm assembly 250 or 260, etc. For example, when an instrument, such as the instrument arm assembly 230, needs to be inserted into the cavity of the patient via the port assembly 210 (or central access channel 210a) and an insufflation of the cavity of the patient needs to be maintained, the first gate assembly 212b may be configured to the open position to allow the instrument to be inserted into the mid section channel 213a. After the instrument (or most of it) passes through the first gate assembly 212b, the first gate assembly 212b may be configured to the closed position. The second gate assembly 214b may then be configured to the open position to allow the instrument to be further inserted through the port assembly 210. After the instrument (or most of it) passes through the second gate assembly 214b, the second gate assembly 214b may be configured to the closed position.

In respect to the central access channel 210a, the central access channel 210a may include or be formed by the first end channel 212a, the second end channel 214a, and/or the mid section channel 213a. The central access channel 210a may be operable to provide an access port (i.e. a passageway or channel) to allow an insertion (or removal) of one or more instruments, such as one or more instrument arm assemblies 230 or 240, one or more image capturing assemblies 220, one or more assistant arm assemblies 250 or 260, etc.

In an example embodiment, the first end section 212, the second end 214, and/or the mid section 213 may be substantially cylindrical in shape. The first end section 212, the second end section 214, and/or the mid section 213 may also be formed in any one of a plurality of other shapes, sizes, and/or dimensions without departing from the teachings of the present disclosure.

In example embodiments, an outer diameter of the first end section 212, the second end 214, and/or the mid section 213 may be between about 28 to 35 mm and an inner diameter (unblocked) of the first end section 212, the second end 214, and/or the mid section 213 may be between about 16 to 21 mm. In an example embodiment, the outer diameter of the first end section 212, the second end 214, and/or the mid section 213 may be about 33 mm and the inner diameter (unblocked) of the first end section 212, the second end 214, and/or the mid section 213 may be about 19 mm. The length of the first end section 212 may be between about 80 to 100 mm, the length of the second end section 214 may be between about 80 to 200 mm, and the length of the mid section 213 may be between about 60 to 80 mm. The overall length of the port assembly 210 may be between about 320 to 380 mm. It is to be understood in the present disclosure that the above dimensions are merely an illustration of example embodiments, and as such the dimensions may be smaller or larger than those recited above without departing from the teachings of the present disclosure.

The port assembly 210, including the first end section 212, the second end section 214, the mid section 213, and/or the anchor ports 216, may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. The first gate assembly 212b and the second gate assembly 214b may be formed using any one or more of a plurality of materials, such as bio-compatible materials (such as silicone rubber and polyurethane). It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Image Capturing Assembly (e.g., Image Capturing Assembly 220)

In an example embodiment, the surgical device 200 may comprise one or more image capturing assemblies (e.g., image capturing assembly 220) configurable to be inserted into and attach to the port assembly 210. One or more of the image capturing assemblies 220 may comprise at an image capturing body 224, a multi-curvable body 222, and an anchoring portion 220a.

Figure 6A:
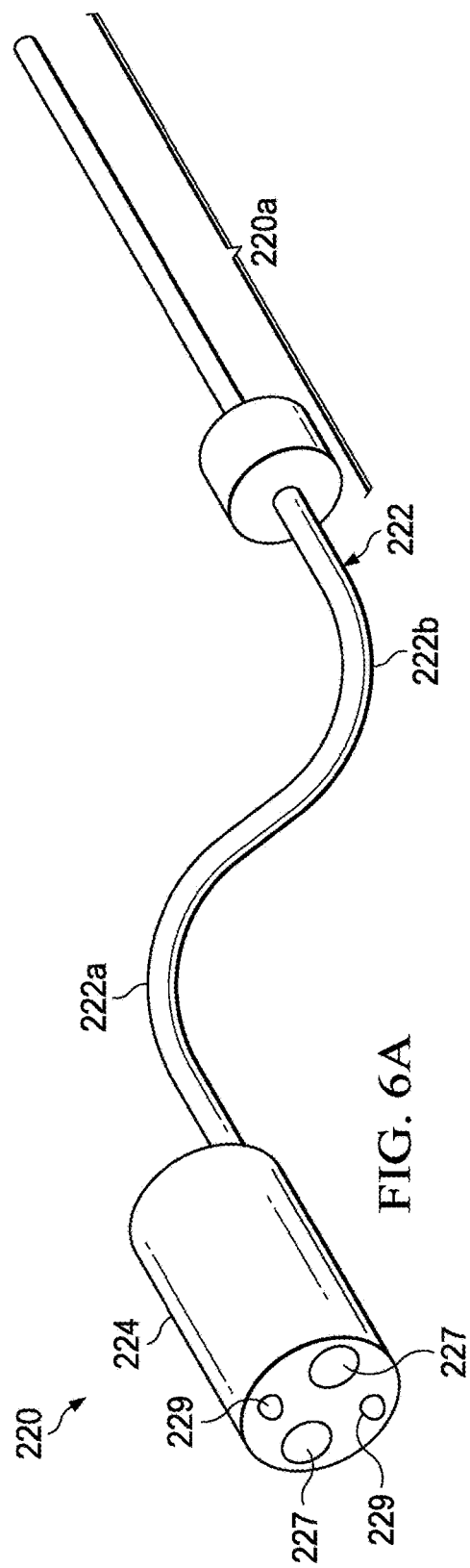
FIG. 6A is an illustration of a perspective view of an example embodiment of an image capturing assembly.
Figure 9A:
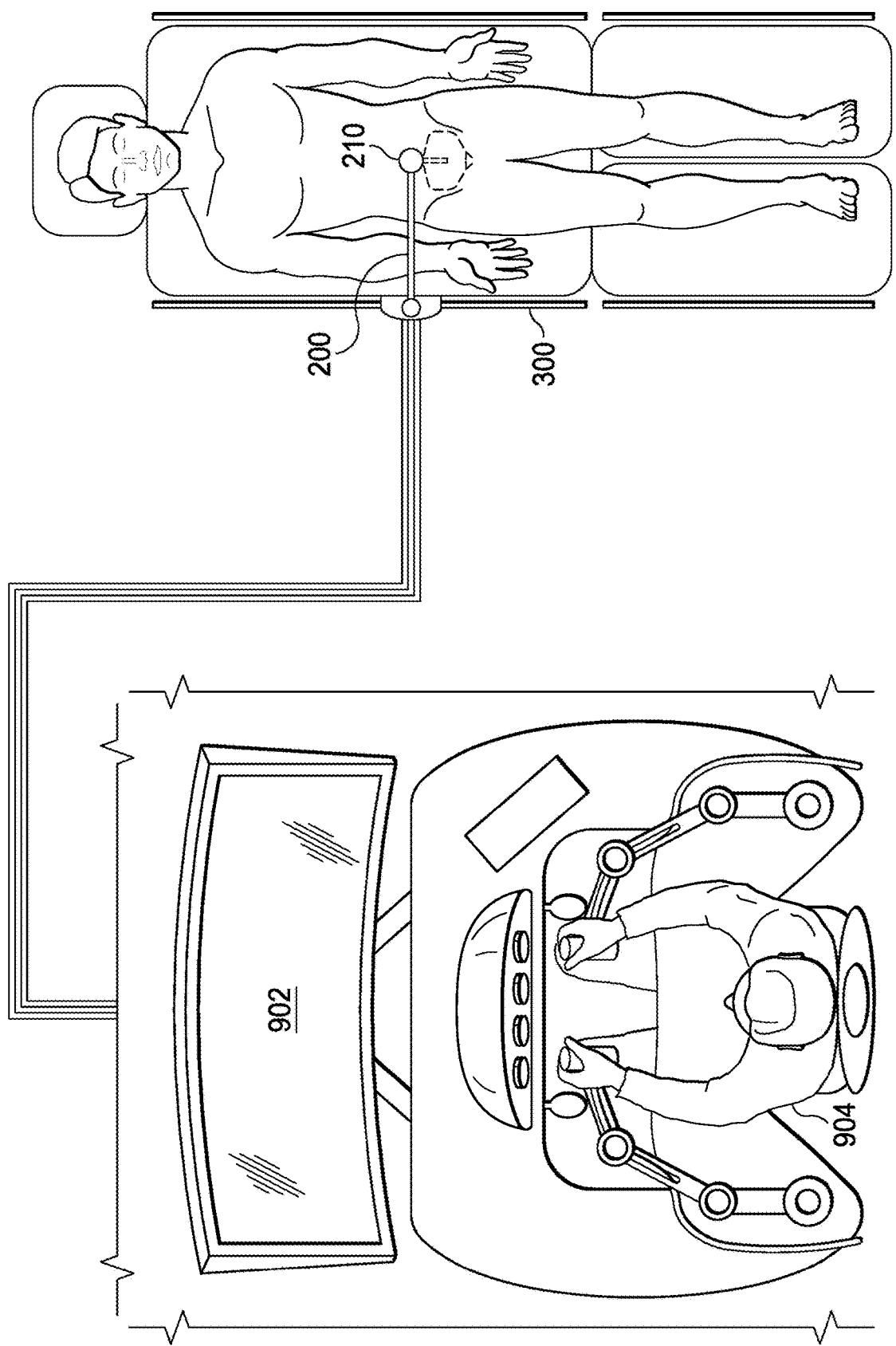
FIG. 9A is an illustration of a perspective view of an example embodiment of a surgical device system.
Figure 9B:
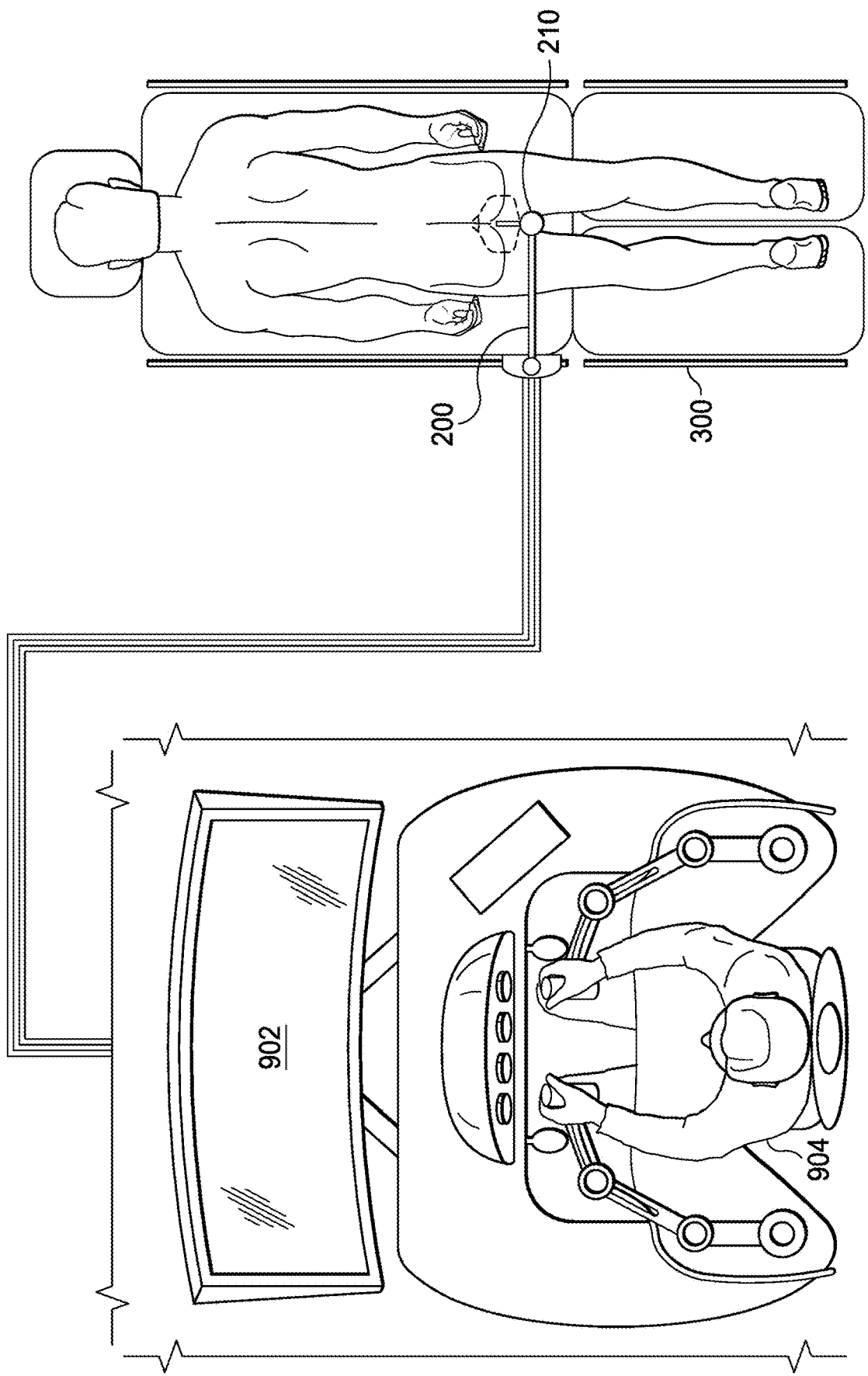
FIG. 9B is an illustration of a perspective view of another example embodiment of a surgical device system.

As illustrated in FIG. 6A, the image capturing body 224 may include one or more cameras 227. Each camera 227 may include a standard and/or high definition 2-dimensional (2D) and/or 3-dimensional (3D) camera operable to capture imaging, such as 2D and/or stereoscopic and/or autostereoscopic 3D imaging, including images, video, and/or audio, and provide in real-time via wired and/or wireless communication the captured imaging, including images, video, and/or audio, to the computing device (or controller or system) of one or more nearby and/or remotely located surgical teams 904, as described above and in the present disclosure. The computing device (or controller or system) may comprise one or more processors, one or more computer-human interfaces, one or more graphical displays (such as computer screens, television screens, portable devices, wearable devices such as glasses, etc.), and/or other devices and/or systems, an example of which is illustrated in FIGS. 9A and 9B. The one or more nearby and/or remotely located surgical teams 904 may be operable to view, hear, sense, analyze, and control (such as pan, zoom, process, adapt, mark, change resolution, etc.) the imaging displayed or represented on one or more standard and/or high definition 2D and/or 3D graphical displays 902, such as shown in the illustration of FIGS. 9A and 9B, and/or portable and/or wearable devices adapted to receive 2D and/or 3D imaging (not shown). The image capturing body 224 may also comprise one or more illumination sources 229, such as an LED, or the like, operable to illuminate or sense at least one or more parts, sections, and/or quadrants of the cavity of the patient, including instruments provided in the cavity of the patient. The image capturing body 224 may further comprise one or more internal temperature control assemblies operable to control (such as reduce) the temperature of one or more components of the image capturing body 224.

As illustrated in the example embodiment of FIG. 6A, one or more of the image capturing assemblies 220 may comprise a multi-curvable body 222 attached to the image capturing body 224. The multi-curvable body 222 may be any elongated multi-curvable, multi-bendable, multi-articulable, and/or snake-like (hereinafter "multi-curvable") body that can be controlled/configured by the surgical team (such as via the computing device/controller) to, among other things, straighten and/or curve (and hold such a straightness and/or curvature) at one or more of a plurality of locations along the multi-curvable body 222, curve (and hold such a curvature) in one or more of a plurality of curvatures, and/or straighten and/or curve (and hold such a straightness and/or curvature) in one or more of a plurality of directions. For example, as illustrated in FIG. 8H, the multi-curvable body 222 may be controllable/configurable by the surgical team (such as via the computing device/controller) to curve at two different locations 222a and 222b along the multi-curvable body 222, and each of the curves may include any curvature and in any direction. It is to be understood that the multi-curvable body 222 may be configurable to curve in more or less than two locations along the multi-curvable body 222 without departing from the teachings of the present disclosure. It is also to be understood that, when the multi-curvable body 222 is configured to curve at any location along the multi-curvable body 222, the curve may be held and/or released (or configured to uncurve, curve less, or straighten) by the surgical team (such as via the computing device/controller).

The multi-curvable body 222 may be formed in any one or more ways known in the art including. For example, the multi-curvable body 222 may include a plurality of segments, each segment linked to an adjacent segment in such a way that the segment may be controlled/configured to be pivotally positioned in a plurality of positions relative to the adjacent segment. As another example, the multi-curvable body 222 may include a plurality of wires, cables, or the like, distributed throughout the multi-curvable body 222 in such a way that a pulling/releasing, shortening/lengthening, tightening/loosening, etc. of one or a combination of cables enables the above-mentioned curving of one or more locations of the multi-curvable body 222 in one or more curvatures and in one or more directions. As another example, the multi-curvable body 222 may include a plurality of springs, gears, motors, etc. for achieving the above-mentioned curving. It is to be understood in the present disclosure that the multi-curvable body 222 may also include a combination of one or more of the above-mentioned approaches.

One or more internal temperature control assemblies (not shown) may be provided for each image capturing assembly 220. Each internal temperature control assembly may be operable to control (such as reduce) the temperature and/or heat emission of the aforementioned camera(s) 227, illumination source(s) 229, and/or multi-curvable body 222. In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well as any solids (if used), may be provided through an interior of the image capturing assembly 220 without increasing dimensions (such as diameter) of the image capturing assembly 220 and/or affecting the controllability/configurability of the multi-curvable body 222.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the cavity of the patient during a surgical procedure. When the internal temperature control assembly utilizes liquids, or the like, example embodiments may be operable to discharge or recycle such liquids outside of the body cavity. When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the image capturing assembly 220. In example embodiments, the internal temperature control assembly may utilize a combination of gases, liquids, solids, and/or the like without departing from the teachings of the present disclosure.

The image capturing assembly 220 may be secured to the port assembly 210 in one or more of a plurality of ways, including those described above and in the present disclosure for the instrument arm assemblies 230 or 240 and/or the assistant arm assemblies 250 or 260. For example, the image capturing assembly 220 may also comprise an anchoring portion 220a (e.g., similar to the securing portion 231a of the instrument arm assembly 220) operable to attach (or secure) the image capturing assembly 220 to one or more anchor ports 216 of the port assembly 210.

In an example embodiment, the image capturing body 224 and the multi-curvable body 222 may each be substantially cylindrical in shape. The image capturing body 224 and the multi-curvable body 222 may also be formed in any one of a plurality of other shapes, sizes, and/or dimensions without departing from the teachings of the present disclosure.

In an example embodiment, the length of the multi-curvable body 222 may be between about 50 to 150 mm. In example embodiments, a length of multi-curvable body 222 may also be adjustable by the surgical team 904 before, during, and/or after insertion of the camera arm assembly into the cavity of the patient. The outer diameter of the multi-curvable body 222 may be between about 5 to 7 mm. It is to be understood in the present disclosure that the above dimensions are merely an illustration of example embodiments, and as such the dimensions may be smaller or larger than those recited above without departing from the teachings of the present disclosure.

The multi-curvable body 222 may be formed using any one or more of a plurality of materials, such as stainless steel, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

Figure 6B:
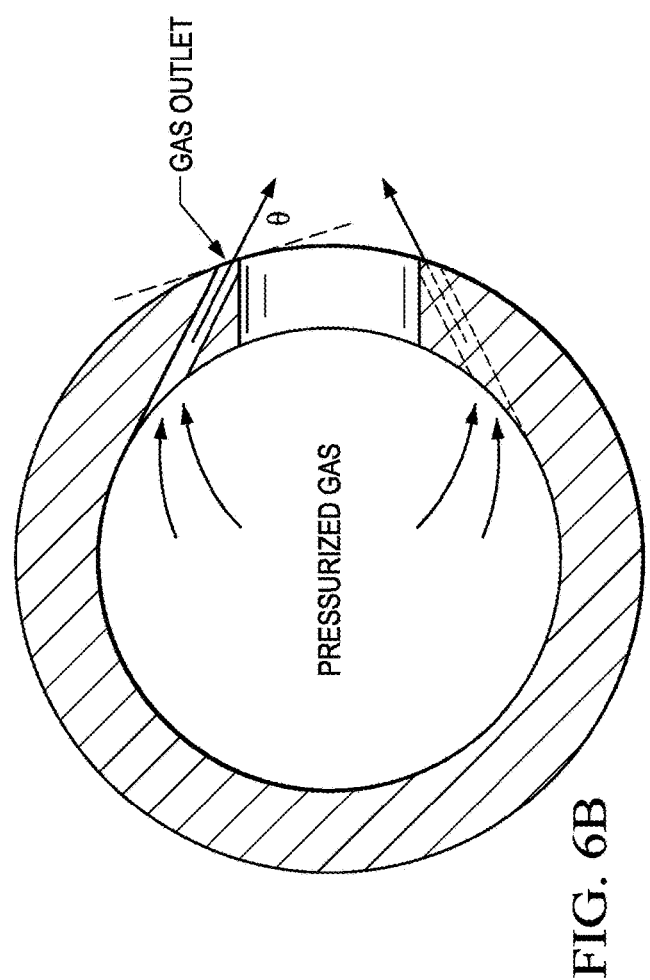
FIG. 6B is an illustration of a cross sectional view of another example embodiment of an image capturing assembly having an internal temperature control assembly.
Figure 6C:
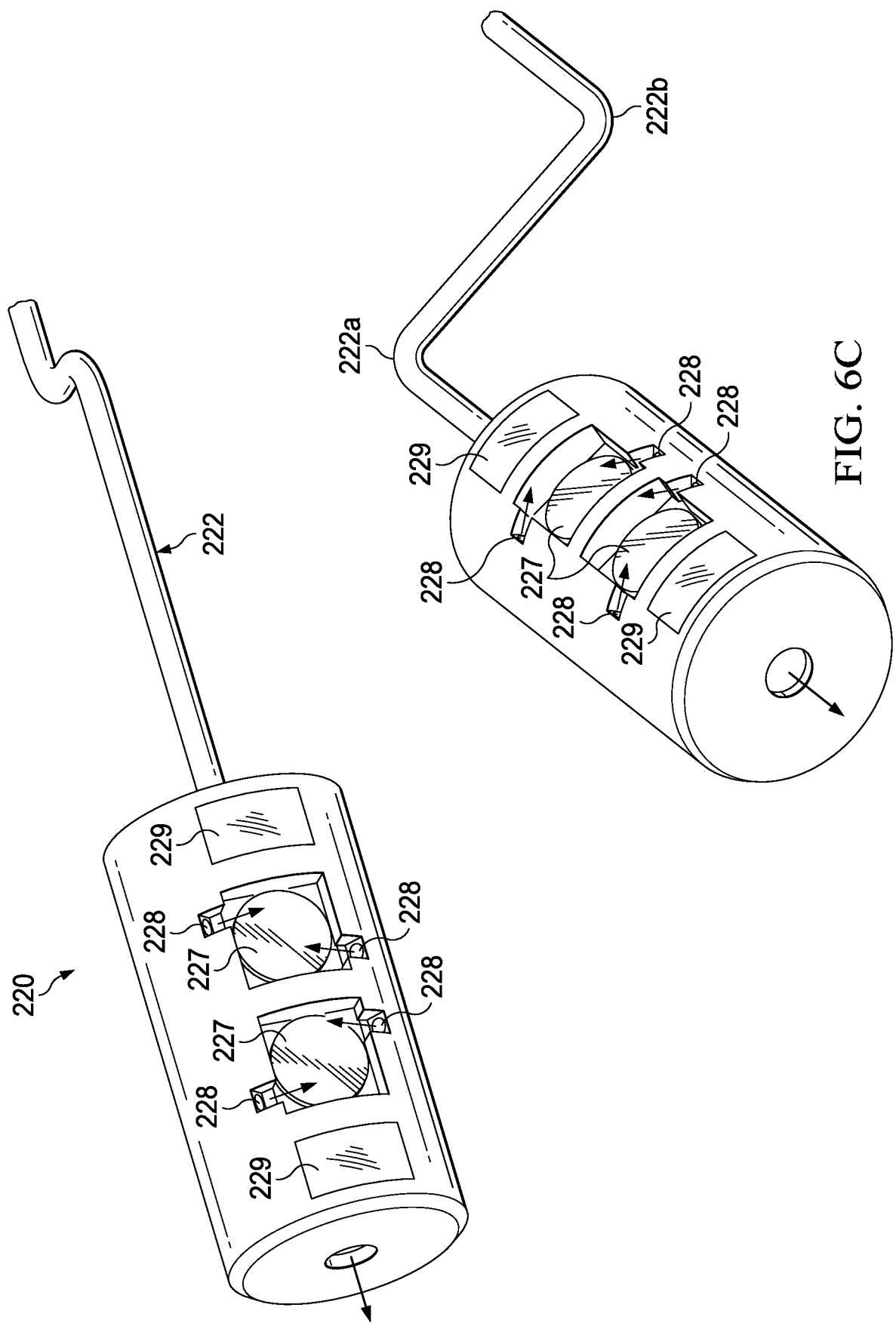
FIG. 6C is an illustration of perspective views of another example embodiment of an image capturing assembly having internal temperature control assemblies.

As illustrated in FIG. 6B and FIG. 6C, the image capturing assembly 220 may further comprise a gas shield 228 located nearby one or more lenses of the camera 227. The image capturing assembly 220 may further comprise a gas shield 228 located nearby one or more of the illumination sources 229 and/or any other sensors (such as temperature sensors, pressure sensors, humidity sensors, etc.) provided by the image capturing assembly 220. The gas shield 228 may comprise one or more openings or the like, one or more external gas sources 228, and one or more tubes, channels, or the like, between the one or more external gas sources and the one or more openings of the gas shield 228. In operation, the gas shield 228 may be operable to provide pressurized gases (and/or liquids), such as carbon dioxide, oxygen, other gases or liquids, or combinations thereof, via the one or more openings of the gas shield 228 to an area in front of the camera 227 (as well as in front of the illumination sources 229 and/or other sensors).

Figure 6D:
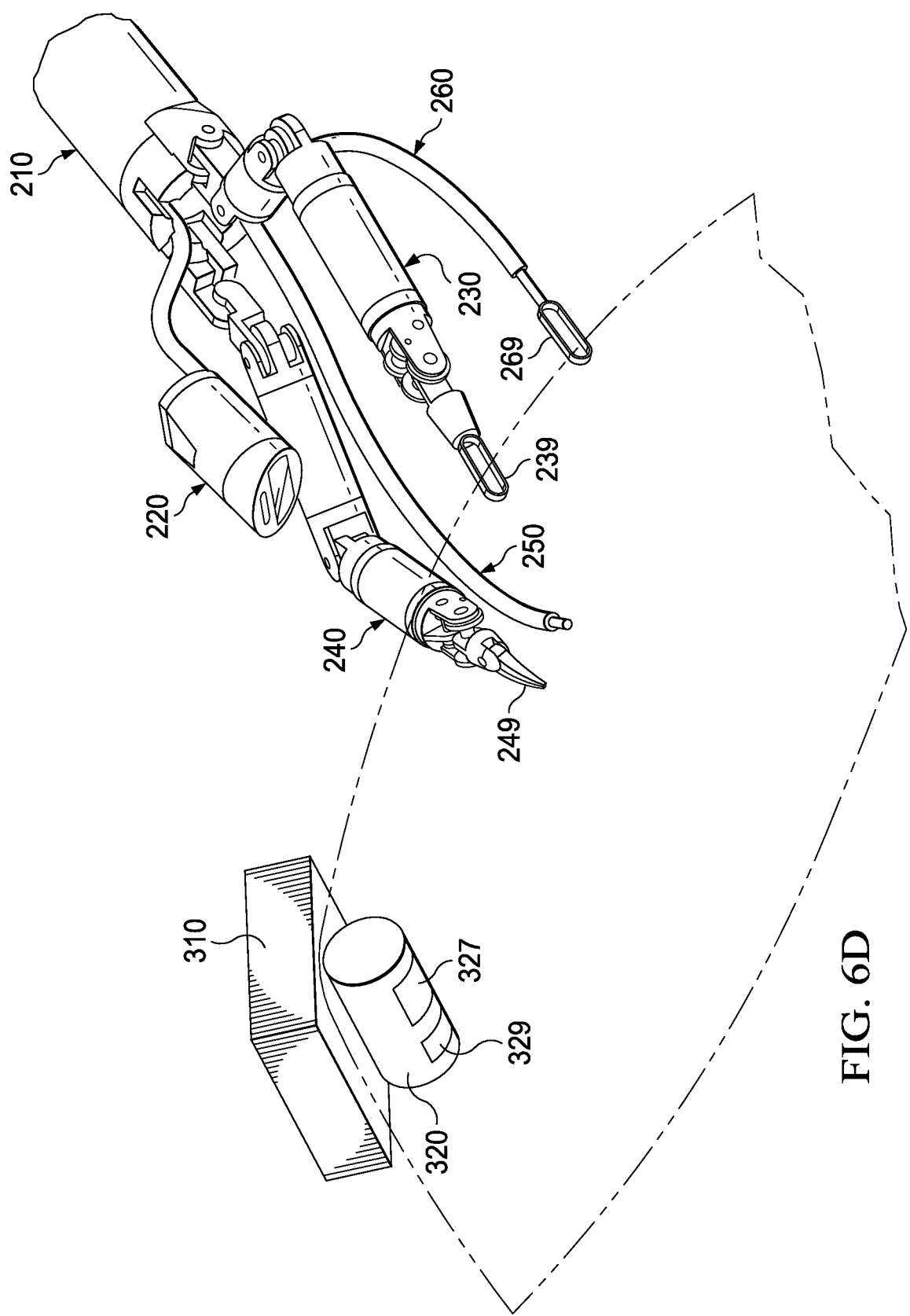
FIG. 6D is an illustration of a perspective view of the system in operation in a cavity of a patient, including a second image capturing assembly.
Figure 7:
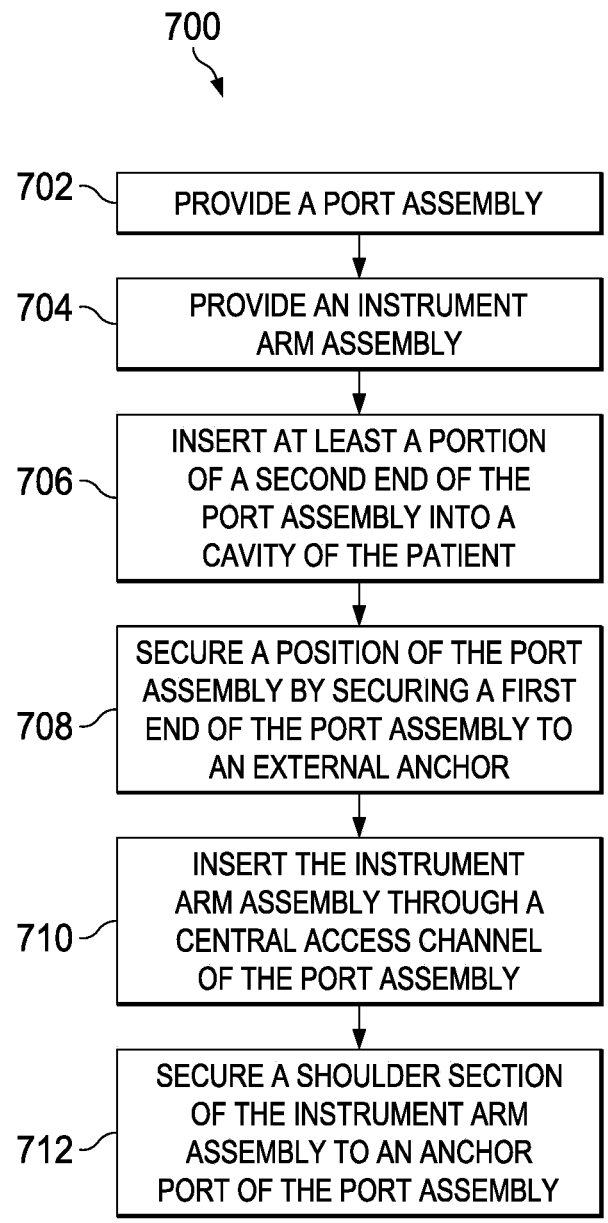
FIG. 7 is a flow diagram of an exemplary method for configuring a surgical device.

The overall system may also include one or more separate image capturing assemblies, such as the separate image capturing assembly 320 illustrated in FIG. 6D. The separate image capturing assembly 320 may be magnetically anchored by a magnetic anchor 310 to an internal wall of the cavity of the patient, such as via a permanent magnet, electromagnet, or the like. In some example embodiments, the magnetic anchor 310 may also be secured/held in position via an external anchor (not shown). The separate image capturing assembly 320 may include one or more cameras 327, and may also include one or more illumination sources 329.

The separate image capturing assembly 320 may be operable to provide one or more of a variety of views, including, but not limited to, a normal view, zoomed view, wide-angled view, and/or panoramic view of the cavity of the patient. The separate image capturing assembly 320 may be positioned in such a way as to provide the surgical team 904 with an unobstructed view of areas of interest within the cavity of the patient. In respect to positioning and securing the separate image capturing assembly 320 in place, as illustrated in FIG. 6D, the separate image capturing assembly 320 may be inserted through the central access channel 210a of the port assembly 210 and to the desired location of the interior wall of the cavity of the patient in one or more of a plurality of ways, including using a surgical tool (not shown), attaching the separate image capturing assembly 320 to a multi-curvable body (not shown) similar to that of the image capturing assembly 220 (as illustrated in FIGS. 2A, 2B, 3A, 3B, and 6D), etc.

The Instrument Arm Assembly (e.g., Instrument Arm Assembly 230, 240)

In an example embodiment, the surgical device 200 may comprise one or more instrument arm assemblies (e.g., first instrument arm assembly 230, second instrument arm assembly 240, third instrument arm assembly (not shown), fourth instrument arm assembly (not shown), etc.), each configurable to attach to the port assembly 210.

One or more of the instrument arm assemblies (such as 230, 240) may comprise a configurable serial (or linear) arrangement of a plurality of instrument arm segments and joint portions, and at least one end instrument (or end effector) 239 integrated into and/or connected to one or more of the instrument arm segments and/or joint portions. The end effector 239 may be any instrument suitable for use in surgical procedures, such as a cutting and/or gripping instrument. One or more of the instrument arm assemblies (such as 230, 240) may also comprise one or more illumination sources (not shown), such as an LED, or the like, operable to illuminate one or more parts of the end effector 239, instrument arm assemblies, and/or parts, sections, and/or quadrants of the abdominal cavity of the patient.

One or more of the instrument arm assemblies (such as 230, 240) may also comprise one or more integrated motors operable to provide at least one degree of freedom for the instrument arm assembly. One or more of the instrument arm assemblies may also include an integrated haptic and/or force feedback subsystem (not shown) in communication with one or more of the integrated motors and/or other sensors and/or instruments operable to provide to the surgical team (such as via computing device/controller) with one or more of a plurality of feedback responses and/or measurements, including those pertaining to position (including orientation), applied force, proximity, temperature, pressure, humidity, etc., of, by, and/or nearby to the instrument arm assembly. For example, the surgical team 904 may be provided with a master input device having manipulators, or the like, having haptic and/or force feedback and designed to map and sense the surgical team's 904 delicate finger-twisting, wrist-bending, and/or other arm/shoulder movements into movements of the instrument arm (such as 230, 240) with high precision, high dexterity, and minimum burden, while also providing feedback of contact resistance (such as tissue resistance).

When an instrument arm assembly (such as 230, 240) comprises one or more illumination sources, cameras, haptic and/or force feedback instruments, and/or other sensors and/or instruments, as described above and in the present disclosure, the instrument arm assembly may also comprise a gas shield, such as the gas shield described above for the image capturing assembly 220. One or more of the instrument arm assemblies (such as 230, 240) may further comprise one or more internal temperature control assemblies operable to control (such as reduce or increase) the temperature of one or more components of the instrument arm assembly.

As illustrated in the example embodiment of FIGS. 2A, 2B, 3A, 3B, FIG. 5A, and FIG. 5B, each of the instrument arm assemblies, including the first instrument arm assembly 230, may comprise a first instrument arm segment (or shoulder section) 231, a second instrument arm segment (or first arm section) 233, a third instrument arm segment (or second arm section) 235, and a fourth instrument arm segment (or hand section) 237. The instrument arm assembly 230 may also comprise a first joint portion (or shoulder joint section) 232, a second joint portion (or elbow section) 234, a third joint portion (or wrist section) 236, and an end effector joint portion 238. Each of the aforementioned joint portions may be configurable, either manually and/or via the computing device (or system), to provide an attached instrument arm segment (and the end effector 239) with one or more in vivo degrees of freedom when the instrument arm assembly is provided in the abdominal cavity of the patient.

For example, the first joint portion (or shoulder joint section) 232 may be operable to provide the second instrument arm segment (or first arm section) 233 with one or two degrees of freedom resembling the one or two degrees of freedom of the human shoulder. As another example, the second joint portion (or elbow section) 234 may be operable to provide the third instrument arm segment (or second arm section) 235 with one or two degrees of freedom resembling the one or two degrees of freedom of the human elbow. As another example, the third joint portion (or wrist section) 236 may be operable to provide the fourth instrument arm segment (or hand section) 237 with one or two degrees of freedom resembling the one or two degrees of freedom of the human wrist. As another example, the end effector joint portion 238 may be operable to provide the end effector 239 with one or more degrees of freedom. Accordingly, one or more of the instrument arm assemblies may be configurable, either manually and/or via the computing device/controller, to provide seven or more in vivo degrees of freedom and, together with the at least one to three or more in vitro degree of freedom provided by the port assembly 210 and the controllable swivel assembly 1000 (see FIGS. 10A and 10B), the one or more of the instrument arm assemblies may be configurable, either manually and/or via the computing device/controller, to provide a total of eight to ten or more degrees of freedom. It is recognized herein that the aforementioned at least seven in vivo degrees of freedom for the instrument arm assembly enables at least the full range of natural movements by a surgeon's arm (via a controller/computer-human interface/manipulator/master input device, such as the example illustrated in FIGS. 9A and 9B) to be substantially directly mapped and/or translated to the instrument arm assembly.

Each joint portion, including joint portions 232, 234, and 236 and instrument joint portion 238 may comprise any one or more configurations of gears and/or gear assemblies, including straight gear configurations, planetary gear configurations, beveled gear configurations, spiral beveled gear configurations, hypoid gear configurations, helical gear configurations, worm gear configurations, and/or any other gear configuration without departing from the teachings of the present disclosure. In example embodiments, each instrument arm assembly may also comprise one or more internal integrated motors, or the like, operable to actuate the gears of each joint portion, including joint portions 232, 234, and 236 and/or the instrument arm segments 231, 233, 235, and 237. In this regard, each of the abovementioned integrated motors, joint portions, and/or instrument arm segments may be operable to communicate, such as receive control commands and/or transmit information, from and/or to the computing device/controller of one or more nearby and/or remotely located surgical teams 904 via wired and/or wireless communication in example embodiments. Furthermore, each of the abovementioned integrated motors, joint portions, and/or instrument arm segments may be operable to receive power from an external power source and/or the computing device/controller via wired and/or wireless transmissions in example embodiments.

Each of the instrument arm assemblies may be securable to (and unsecured from) the anchor ports 216 of the port assembly 210 via a securing portion 231a of the shoulder section 231. It is recognized in the present disclosure that the instrument arm assembly 230, 240 may be secured to the anchor port 216 of the port assembly 210 in the forward-directed position (e.g., as illustrated in FIGS. 2B and 3B) and/or the reverse-directed position (e.g., as illustrated in FIGS. 2A and 3A). Furthermore, in example embodiments, the instrument arm assembly 230, 240 may or may not be transitioned between the forward-directed position and the reverse-directed position. In example embodiments where the instrument arm assembly 230, 240 is transitionable between the forward-directed position and the reverse-directed position, such transition may be performable before, during, and/or after the securing of the shoulder section 231 to the anchor port 216 of the port assembly 210. For example, in such embodiments, the securing portion 231a may be adjustably changed in position relative to the shoulder section 231, such as from the forward-directed position illustrated in FIG. 5A to the reverse-directed position illustrated in FIG. 5B, and vice versa.

One or more internal temperature control assemblies (not shown) may be provided for each of the one or more instrument arm assemblies 230, 240. Each internal temperature control assembly may be operable to control (such as reduce) the temperature and/or heat emission of the aforementioned gears and/or gear assemblies, motors, instrument joint portions (such as 232, 234, and 236), and/or instrument arm segments (such as 231, 233, 235, and 237). The one or more internal temperature control assemblies may also be operable to control (such as increase or decrease) the temperature of the end effector 239 (which may be desirable when the end effector 239 is a cutting tool, or the like). In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well any solids (if used), may be provided through an interior of the instrument arm assembly without increasing dimensions (such as diameter) of the instrument arm assembly.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the body cavity, such as via an opening (not shown). When the internal temperature control assembly utilizes liquids, or the like, example embodiments may be operable to discharge or recycle such liquids outside of the body cavity. When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the instrument arm assembly 230, 240.

In example embodiments, the internal temperature control assembly may utilize a combination of gases, liquids, solids, and/or the like without departing from the teachings of the present disclosure.

After the instrument arm assembly 230, 240 has been inserted and attached (or secured) to the port assembly 210, the end effector 239 may be configurable, either manually and/or via the computing device (or system), to apply between about 0 to 20 N of force when performing surgical actions and procedures, such as clipping and/or grasping actions. Furthermore, the end effector 239 may be configurable, either manually and/or via the computing device/controller, to apply between about 0 to 10 N of force when performing other surgical actions and procedures, such as translational, twisting, pulling, and/or pushing actions. It is to be understood in the present disclosure that the above range of applicable force are merely an illustration of example embodiments, and as such the range of applicable force may be smaller or larger than those recited above without departing from the teachings of the present disclosure.

In an example embodiment, the instrument arm segments, including the first instrument arm segment 231, the second instrument arm segment 233, the third instrument arm segment 235, and/or the fourth instrument arm segment 237, may be substantially cylindrical in shape. The instrument arm segments, including the first instrument arm segment 231, the second instrument arm segment 233, the third instrument arm segment 235, and/or the fourth instrument arm segment 237, may also be formed in any one of a plurality of other shapes, sizes, and/or dimensions without departing from the teachings of the present disclosure.

As described above, the instrument arm assembly 230, 240 may also include one or more securing portions 231*a*. The securing portion 231*a* may be attachable or attached to the first instrument arm segment 231, a part of the first instrument arm segment 231, and/or formed as a unitary article with the first instrument arm segment 231. Such securing portions 231*a* may be for use in securing the instrument arm assembly 230, 240 to the anchor ports 216. Such securing portions 231*a* may also be for use in performing or assisting in performing the process of inserting the instrument arm assembly 230, 240 into and securing onto the port assembly 210 in example embodiments.

After the instrument arm assembly 230 is inserted through the port assembly 210 and into the cavity of a patient (such as a vagina or rectum), the securing portion 231*a* of the first instrument arm segment (or shoulder section) 231 may be securely received by the anchor port 216 of the port assembly 210.

In an example embodiment, the length of the securing portion 231*a* may be between about 350 to 450 mm, the length of the first instrument arm segment 231 may be between about 15 to 40 mm, the length of the second instrument arm segment 233 may be between about 80 to 105 mm, the length of the third instrument arm segment 235 may be between about 65 to 90 mm, the length of the fourth instrument arm segment 237 may be between about 5 to 30 mm, and the overall length of the collective instrument arm may be between about 165 to 265 mm. In example embodiments, the length of the securing portion 231*a* may be between about 340 to 400 mm, the length of the first instrument arm segment 231 may be between about 15 to 25 mm, the length of the second instrument arm segment 233 may be between about 90 to 100 mm, the length of the third instrument arm segment 235 may be between about 75 to 85 mm, the length of the fourth instrument arm segment 237 may be between about 15 to 25 mm, and the overall length of the collective instrument arm may be between about 195 to 235 mm. In example embodiments, a length of one or more of the instrument arm segments, the securing portion 231*a*, and/or the end effector 239 may also be adjustable by the computing device (or system) of one or more nearby and/or remotely located surgical teams 904 before, during, and/or after insertion of the instrument arm assembly into the cavity of the patient. The outer diameter of one or more of the instrument arm segments may be about 10 to 16 mm. In an example embodiment, the outer diameter of one or more of the instrument arm segments may be about 16 mm.

Each of the instrument arm assemblies, including the securing portion 231*a*, the first instrument arm segment 231, the second instrument arm segment 233, the third instrument arm segment 235, the fourth instrument arm segment 237, the end effector 239, the first joint portion 232, the second joint portion 234, the third joint portion 236, and/or the instrument joint 238, may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. It is to be understood in the present disclosure that other materials may also be used without departing from the teachings of the present disclosure.

The Assistant Arm Assemblies (e.g., Assistant Arm Assembly 250, 260)

In an example embodiment, the surgical device 200 may comprise one or more assistant arm assemblies (e.g., assistant arm assembly 250 or 260) configurable to be inserted into and attach to the port assembly 210. As illustrated in FIGS. 2A, 2B, 3A, and 3B, one or more of the assistant arm assemblies may be a suction/irrigation assembly 250 or an assistant instrument arm assembly such as a retractor arm assembly 260, and each of them may include a multi-curvable body 252 or 262, respectively, and an anchoring portion, respectively (e.g., similar to the multi-curvable body 222 and anchoring portion 220*a* of the image capturing assembly 220).

As illustrated in FIGS. 2A, 2B, 3A, and 3B, the suction/irrigation assembly 250 may include an end having a suction port 259 for applying a suction or negative pressure, which may be for use in removing liquids (e.g., blood, etc.) from the cavity of the patient. In respect to the assistant instrument arm assembly 260, the assistant instrument arm assembly 260 may include an end having an instrument 269, such as a gripper, retractor, cutter, needle, or the like, which may be for use in assisting the one or more instrument arm assemblies 230 and/or 240 in performing the surgical action.

As illustrated in the example embodiment of FIGS. 2A, 2B, 3A, and 3B, the assistant arm assemblies 250 and/or 260 may comprise a multi-curvable body 252 and/or 262, respectively, attached to their ends (suction port or instrument, respectively). The multi-curvable body 252 or 262 may be any elongated multi-curvable body similar to that of the image capturing assembly 220 described above and in the present disclosure that can be controlled/configured by the surgical team 904 (such as via the computing device/controller/manipulator/master input device) to, among other things, straighten and/or curve (and hold such a straightness and/or curvature) at one or more of a plurality of locations along the multi-curvable body 252 or 262, curve (and hold such a curvature) in one or more of a plurality of curvatures, and/or straighten and/or curve (and hold such a straightness and/or curvature) in one or more of a plurality of directions. It is to be understood that, when the multi-curvable body 252 or 262 is configured to curve at any location along the multi-curvable body 252 or 262, the curve may be held and/or released (or configured to uncurve, curve less, or straighten) by the surgical team 904 (such as via the computing device/controller/manipulator/master input device).

The multi-curvable body 252 or 262 may be formed in any one or more ways known in the art. For example, the multi-curvable body 252 or 262 may be a unitary or substantially unitary elongated body having a plurality of wires, cables, or the like, distributed/run throughout the multi-curvable body 252 or 262 in such a way that a manipulating, such as a pulling/releasing, shortening/lengthening, tightening/loosening, etc., of one or a combination of such wires, cables, or the like enables the above-mentioned curving of one or more locations of the multi-curvable body 252 or 262 in one or more curvatures and in one or more directions. As another example, the multi-curvable body 252 or 262 may include a plurality of segments, each segment linked to an adjacent segment in such a way that the segment may be controlled/configured to be pivotally positioned in a plurality of positions relative to the adjacent segment. As another example, the multi-curvable body 252 or 262 may include a plurality of springs, gears, motors, etc. for achieving the above-mentioned curving of one or more locations of the multi-curvable body 252 or 262 in one or more curvatures and in one or more directions. It is to be understood in the present disclosure that the multi-curvable body 252 or 262 may also include a combination of one or more of the above-mentioned approaches.

The assistant arm assembly 250 or 260 may be secured to the port assembly 210 in one or more of a plurality of ways, including those described above and in the present disclosure for the instrument arm assemblies 230, 240 and/or the image capturing assembly 220. For example, the assistant arm assembly 250 or 260 may also comprise an anchoring portion (e g, similar to the anchoring portion 220a of the image capturing assembly 220 and/or the securing portion 231a of the instrument arm assembly 220), respectively, operable to attach (or secure) the assistant arm assembly 250 or 260 to one or more anchor ports 216 of the port assembly 210.

In an example embodiment, the multi-curvable body 252 or 262 may each be substantially cylindrical in shape. The multi-curvable body 252 or 262 may also be formed in any one of a plurality of other shapes, sizes, and/or dimensions without departing from the teachings of the present disclosure.

In an example embodiment, the length of the multi-curvable body 252 or 262 may be between about 170 to 270 mm. In example embodiments, a length of multi-curvable body 252 or 262 may also be adjustable by the surgical team 904 before, during, and/or after insertion of the camera arm assembly into the cavity of the patient. The outer diameter of the multi-curvable body 252 or 262 may be between about 5 to 7 mm. It is to be understood in the present disclosure that the above dimensions are merely an illustration of example embodiments, and as such the dimensions may be smaller or larger than those recited above without departing from the teachings of the present disclosure.

Controller

In example embodiments, the surgical system may include a controller (or computing device, manipulator, and/or master input device). The controller may be configurable to perform one or more of a plurality of operations in and on the surgical system 200. For example, the controller may be configurable to communicate with and/or control one or more elements of the surgical system 200, such as the external anchor 1 or 1000, the port assembly 210, the instrument arm assemblies 230 or 240, the image capturing assembly 220, and/or the assistant arm assemblies 250 or 260. The controller may be accessible and/or controllable by the surgical team 904, and the surgical team may be able to communicate with and/or control the configuring and/or operation of the one or more elements of the surgical system 200. For example, the controller may be configurable to control a movement and action of some or all parts of the instrument arm assemblies 230 or 240, the first gate assembly 212b, the second gate assembly 214b, the movement and action of some or all parts of the image capturing assembly 220 (including the image capturing, temperature control, etc.), the movement and action of some or all parts of the multi-curvable body 222 of the image capturing assembly 220, the movement and action of some or all parts of the multi-curvable body 252 or 262 of the assistant arm assemblies, the movement and action of some or all parts of the assistant arm assemblies 250 or 260, and the like.

Method of Setting Up the Surgical Device 200 in a Forward-Directed Position (e.g., Method 700)

As illustrated in FIG. 7 and FIGS. 8A-E, example embodiments of the surgical device 200 may be configurable to perform a forward-directed surgical action or procedure in one of a plurality of ways. In an example embodiment, the external anchor 1 may be provided and installed/anchored to the stationary object. The port assembly 210 may be provided (e.g., action 702), and the instrument arm assembly may be provided (e.g., action 704). A second instrument arm assembly may be provided, as well as the image capturing assembly 220 and/or 320 and any of the assistant arm assemblies 250 and/or 260 required. The port assembly 210 may be inserted (e.g., action 706) into the opening (and cavity) of the patient and anchored in position using the external anchor 1 (e.g., action 708), and a workable volume/space in the cavity may be formed, such as via insufflation using $CO_2$ and/or other gases, vacuum suction tools, and/or retractable hook tools. The controllable swivel assembly 1000 may also be used in example embodiments. For example, a workable abdominal cavity of about 10-12 cm in height may be provided for the patient. Thereafter, one or more image capturing assemblies 220, one or more assistant arm assemblies (e.g., action 710), and one or more assistant arm assemblies 250 or 260 (if needed) may be inserted into the port assembly 210 via the central access channel 210a, secured to the anchor ports 216, and configured in the cavity of the patient. A surgical action or procedure may then be performed in any part, area, and/or quadrant of the cavity of the patient using the surgical device 200. These processes will now be described below with references to at least FIGS. 7, 8A-E, 9B, and 10B.

(1) Providing the External Anchor and Installing the Port Assembly.

In an example embodiment, the external anchor 1 may be provided and installed/anchored to one or more stationary objects, such as a side rail 300 of a surgical table/bed, as illustrated in FIGS. 1A and 1B. One or more segments 2, 6, 10, and 14 of the external anchor 1 may cooperate using one or more joints 4, 8, 12, and 16 of the external anchor 1 to fix the position (including orientation) of the port assembly 210 in or about the opening of the patient.

In an example embodiment, as illustrated in FIGS. 10A and 10B, the external anchor 1 may comprise a controllable swivel assembly 1000 operable to provide one or more additional in vitro degrees of freedom, such as via a first swivel portion 1002, second swivel portion 1004, and/or third swivel portion 1006. The controllable swivel assembly 1000 may further comprise a motor 1002a for the first swivel portion 1002, a motor 1004a for the second swivel portion 1004, a motor 1006a for the third swivel portion 1006, one or more supporting arms 1008, and one or more locks 1010.

The first swivel portion 1002 may be operable to provide, as one of the in vitro degrees of freedom, a translational movement of the port assembly 210 along an axis defined by the elongated length of the port assembly 210, as illustrated by the arrow A. In example embodiments, the translational movement, as illustrated by arrow A, provided by the first swivel portion 1002 may be between about 0 to 50 mm.

The controllable swivel assembly 1000 may further comprise a second swivel portion 1004 operable to provide, as another one of the in vitro degrees of freedom, a torsional or rotational movement of the port assembly 210 about an axis depicted by axis Y. In example embodiments, the torsional or rotational movement, as illustrated by the arrow B, provided by the second swivel portion 1004 may be between about +/−180 degrees.

The controllable swivel assembly 1000 may further comprise a third swivel portion 1006 operable to provide, as another one of the in vitro degrees of freedom, a pivotal or rotational movement of the port assembly 210 about an axis perpendicular to the Y-axis, such as the axis depicted by axis Z (which comes out of the page). In example embodiments, the Z-axis or the center of rotation may be located at about opening of the patient, such as at the mid-point of the abdominal wall. In example embodiments, the pivotal or rotational movement, as illustrated by the arrow C, provided by the third swivel portion 1006 may be between about +/−80 degrees.

It is recognized in the present disclosure that the controllable swivel assembly 1000 may comprise the first swivel portion 1002, second swivel portion 1004, and/or third swivel portion 1006 in example embodiments. The controllable swivel assembly 1000 may further comprise other swivel portions (not shown) when more than three in vitro degrees of freedom and/or movements/rotations other than those providable by the first swivel portion 1002, second swivel portion 1004, and third swivel portion 1006 are desired and/or required.

The controllable swivel assembly 1000, including the first swivel portion 1002, the second swivel portion 1004, and/or the third swivel portion 1006, may be controllable either locally or remotely by the surgical team.

In an example embodiment, the port assembly 210 may be installed and secured to the external anchor 1 or 1000. As illustrated in FIGS. 8A-E, the second end 214 of the port assembly 210 may be inserted into the opening of the patient and into the cavity of the patient and the first end 212 of the port assembly 210 may be secured to the external anchor 1 or 1000. Thereafter, a workable volume/space in the cavity may be formed in the cavity of the patient, such as via insufflation using $CO_2$ and/or other gases, vacuum suction tools, and/or retractable hook tools. Before doing so, the first gate assembly 212b and the second gate assembly 214b may be expanded to the closed position. Insufflation of the cavity may be achieved in one or more of a plurality of ways. For example, the insufflation port of the port assembly 210 may be used to provide the required insufflation.

(2) Inserting and Attaching the Image Capturing Assembly.

Figure 8A:
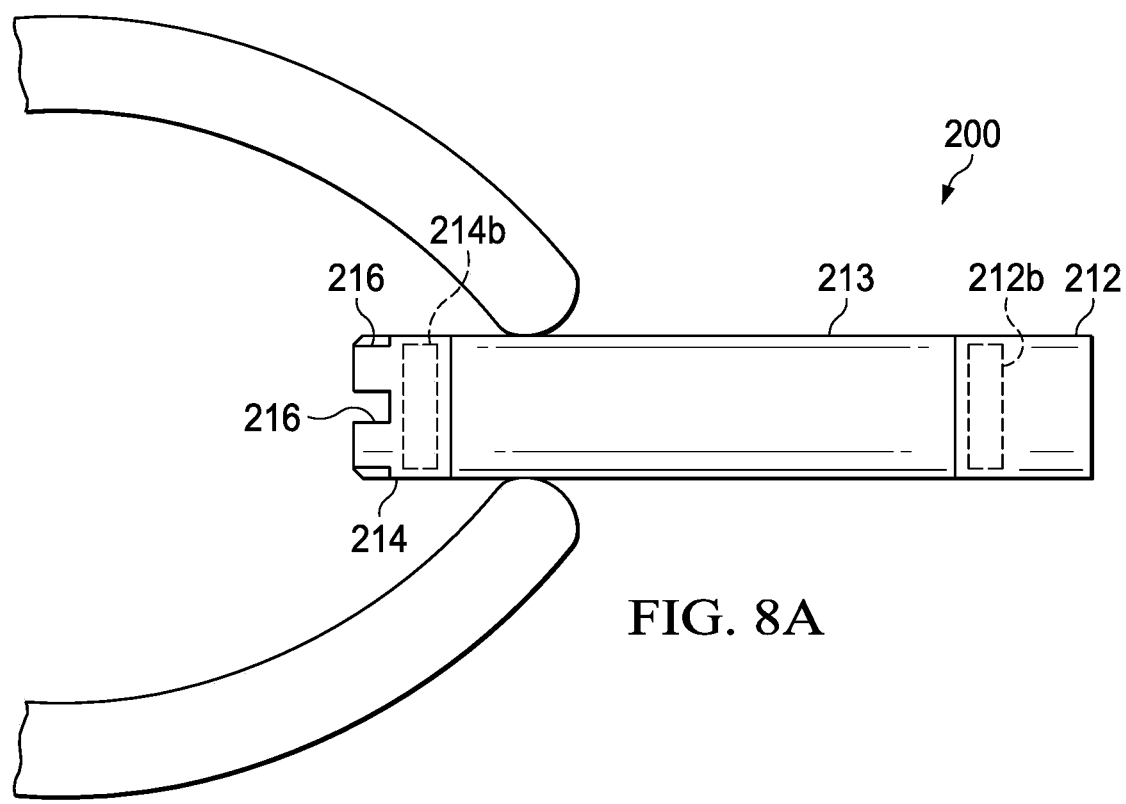
FIGS. 8A-E are illustrations of a side view of an example embodiment of a method of configuring a surgical device in a forward-directed position.

After the workable volume/space in the cavity has been formed and the port assembly 210 is secured in position, as illustrated in FIG. 8A, the image capturing assembly 220 may be inserted through the central access channel 210a and secured to the anchor port 216 of the port assembly 210. To do so while maintaining the workable volume/space, the first gate assembly 212b may be configured to the open position while the second gate assembly 214b is configured to the closed position. Once the first gate assembly 212b is in the open position, the image capturing assembly 220 may be inserted into the mid section 213. The first gate assembly 212b may then be configured to the closed position after the image capturing assembly 220 passes through the first gate assembly 212b. The second gate assembly 214b may then be configured to the open position. It is recognized in the present disclosure that the workable volume/space in the cavity is maintained via the insufflation since the first gate assembly 212b is configured to the closed position. Once the second gate assembly 214b is in the open position, the image capturing assembly 220 may be inserted into the cavity of the patient and the anchor portion 220a secured to an anchor port 216. The second gate assembly 214b may then be configured to the closed position after the image capturing assembly 220 passes through the second gate assembly 214b. The multi-curvable body 222 of the image capturing assembly 220 may then be configured/controlled to curve in one or more locations along the multi-curvable body 222 so that the image capturing assembly 220 can be directed in a forward-directed position (as illustrated in FIGS. 2B and 3B).

The separate image capturing assembly 320 may also be inserted through the port assembly 210 in a similar manner as described above. Once inserted through the port assembly 210 and into the cavity of the patient, the separate image capturing assembly 320 may then be attached/secured to the interior wall of the cavity of the patient via the magnetic anchor 310.

(3) Inserting and Attaching a First Instrument Arm Assembly.

Figure 8B:
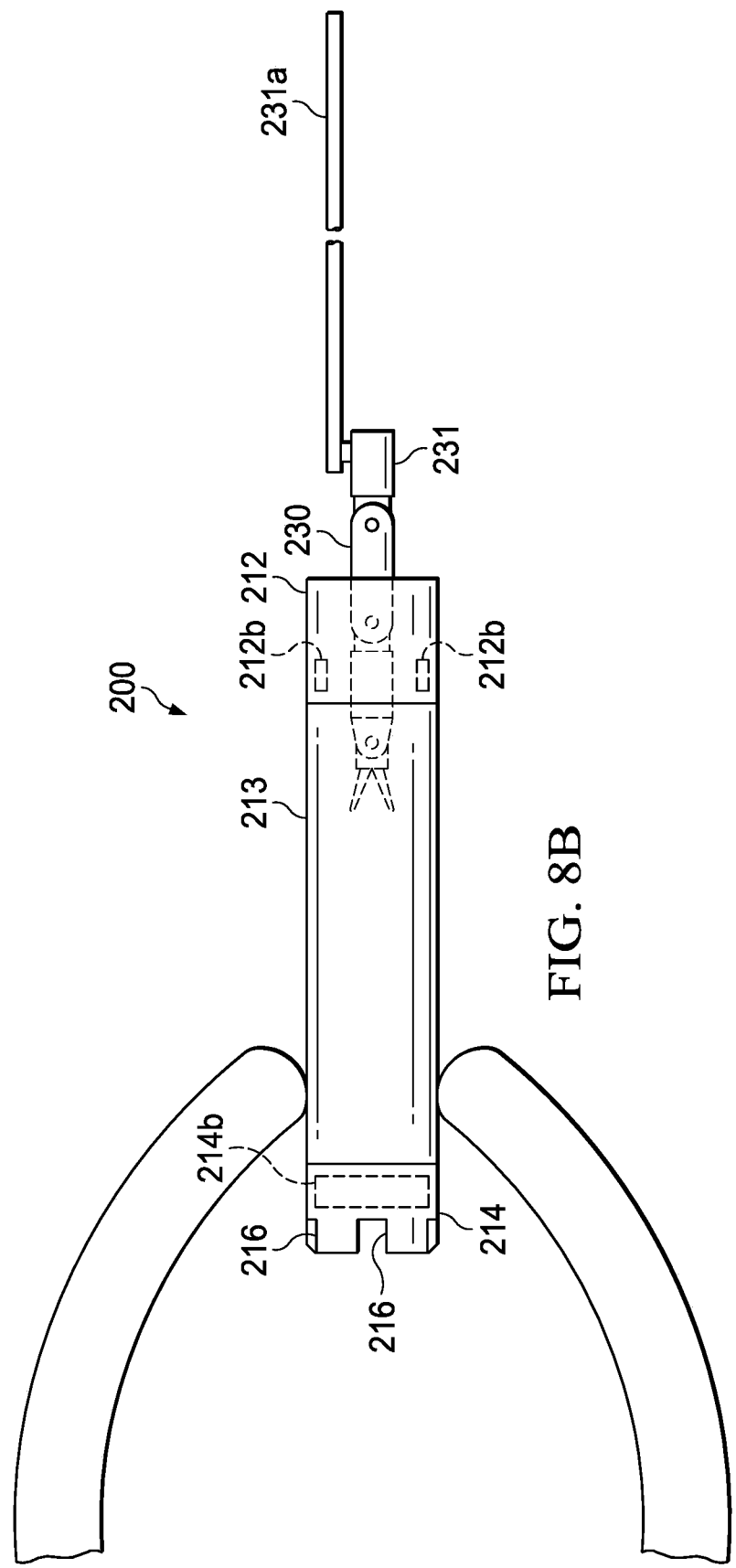
Figure 8C:
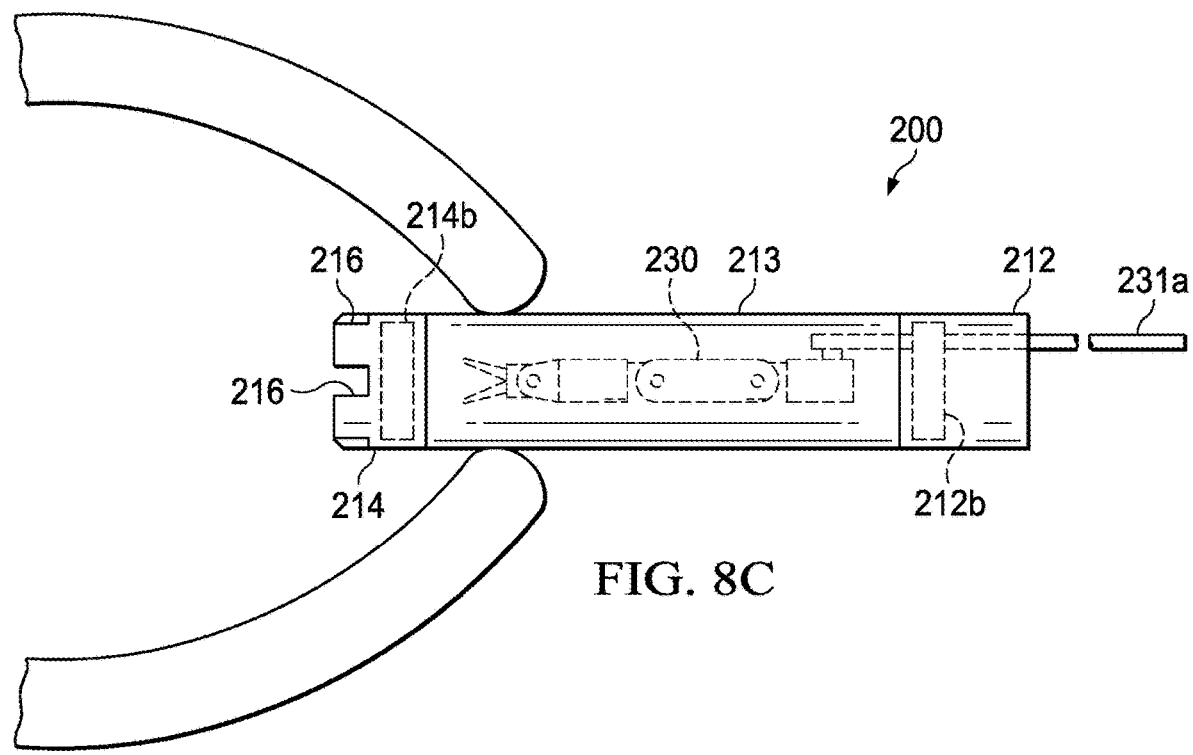
Figure 8D:
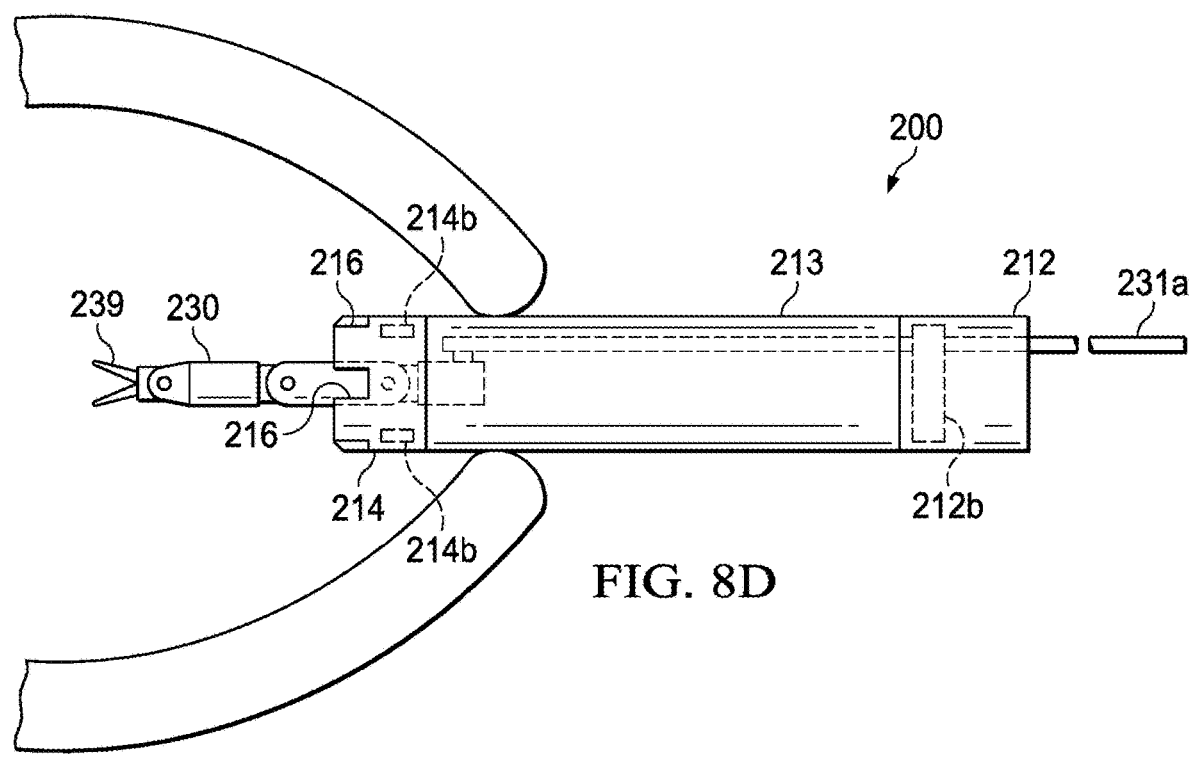
Figure 8E:
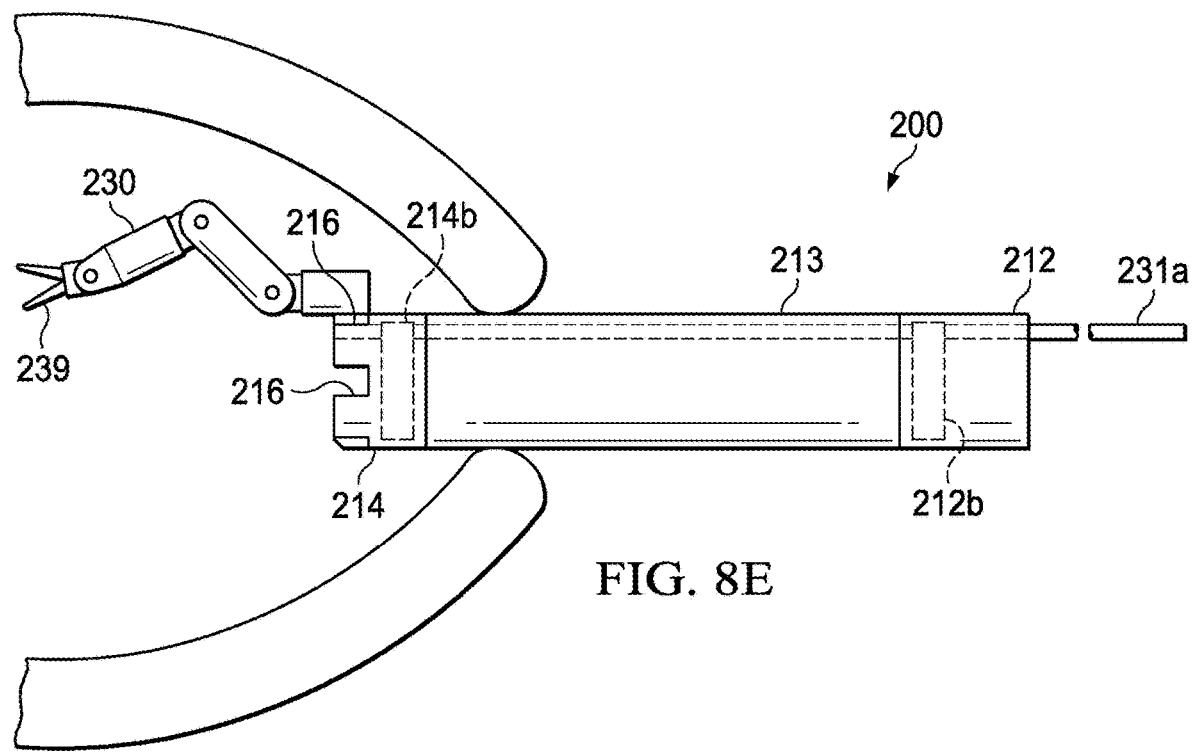

The instrument arm assembly 230 may be inserted through the central access channel 210a and secured to the anchor port 216 of the port assembly 210. To do so while maintaining the workable volume/space, the first gate assembly 212b may again be configured to the open position while the second gate assembly 214b is configured to the closed position. Once the first gate assembly 212b is in the open position, the instrument arm assembly 230 may be inserted into the mid section 213, as illustrated in FIG. 8B. The first gate assembly 212b may then be configured to the closed position after the instrument arm assembly 230 passes through the first gate assembly 212b and into the mid section 213, as illustrated in FIG. 8C. The second gate assembly 214b may then be configured to the open position, as illustrated in FIG. 8D. Once the second gate assembly 214b is in the open position, the instrument arm assembly 230 may be inserted into the cavity of the patient and the securing portion 231a secured to an anchor port 216, as illustrated in FIG. 8E. The second gate assembly 214b may then be configured to the closed position after the instrument arm assembly 230 passes through the second gate assembly 214b.

(5) Inserting and Attaching One or More Additional Instrument Arm Assemblies, One or More Assistant Arm Assemblies, and/or One or More Additional Camera Arm Assemblies.

One or more additional instrument arm assemblies 240, one or more assistant arm assemblies 250 or 260, and/or one or more additional image capturing assemblies (not shown) may also be inserted into the port assembly 210 via the central access channel 210a in the same manner as described above for the image capturing assembly 220 and the instrument arm assembly 230.

(6) Unattaching and Removing the Instrument Arm Assembly, Image Capturing Assembly, and Assistant Arm Assemblies.

The instrument arm assembly 230, image capturing assembly 220, other instrument arm assembly 240 (if provided), other image capturing assembly (if provided), and the one or more other assistant arm assemblies 250 or 260 (if provided) may be unattached (or unsecured) from the anchor ports 216 and removed from the cavity of the patient via the central access channel 210a of the port assembly 210 in a substantially reverse manner as described above for the inserting and attaching.

Method of Setting Up the Surgical Device 200 in a Reverse-Directed Position (e.g., Method 700)

As illustrated in FIGS. 7 and 8F-K, example embodiments of the surgical device 200 may be configurable to perform a reverse-directed surgical action or procedure in one of a plurality of ways. In an example embodiment, the external anchor 1 may be provided and installed/anchored to the stationary object in a similar manner as described above and in the present disclosure. The port assembly 210 may be provided (e.g., action 702), and the instrument arm assembly may be provided (e.g., action 704). A second instrument arm assembly may be provided, as well as the image capturing assembly 220 and/or 320 and any of the assistant arm assemblies 250 and/or 260 required. The port assembly 210 may be inserted (e.g., action 706) into the opening (and cavity) of the patient and anchored in position using the external anchor 1 (e.g., action 708), and a workable volume/space in the cavity may be formed, such as via insufflation using $CO_2$ and/or other gases, vacuum suction tools, and/or retractable hook tools. The controllable swivel assembly 1000 may also be used in example embodiments. For example, a workable abdominal cavity of about 10-12 cm in height may be provided for the patient. Thereafter, one or more image capturing assemblies 220, one or more assistant arm assemblies (e.g., action 710), and one or more assistant arm assemblies 250 or 260 (if needed) may be inserted into the port assembly 210 via the central access channel 210a, secured to the anchor ports 216, and configured in the cavity of the patient. For the inserting, each of the image capturing assemblies 220, instrument arm assemblies 230 and/or 240, and assistant arm assemblies 250 and/or 260 are inserted in reverse orientation as compared to the forward-directed position described above and in the present disclosure. A surgical action or procedure may then be performed in any part, area, and/or quadrant of the cavity of the patient using the surgical device 200. These processes will now be described below with references to at least FIGS. 7, 8F-K, 9B, and 10B.

(1) Providing the External Anchor and Installing the Port Assembly.

In an example embodiment, the port assembly 210 may be installed and secured to the external anchor 1 or 1000. As illustrated in FIGS. 8A-E, the second end 214 of the port assembly 210 is inserted into the opening of the patient and into the cavity of the patient and the first end 212 of the port assembly 210 is secured to the external anchor 1 or 1000. Thereafter, a workable volume/space in the cavity may be formed in the cavity of the patient, such as via insufflation using $CO_2$ and/or other gases, vacuum suction tools, and/or retractable hook tools. Before doing so, the first gate assembly 212b and the second gate assembly 214b may be expanded to the closed position. Insufflation of the cavity may be achieved in one or more of a plurality of ways. For example, the insufflation port of the port assembly 210 may be used to provide the required insufflation.

(2) Inserting and Attaching the Image Capturing Assembly.

Figure 8F:
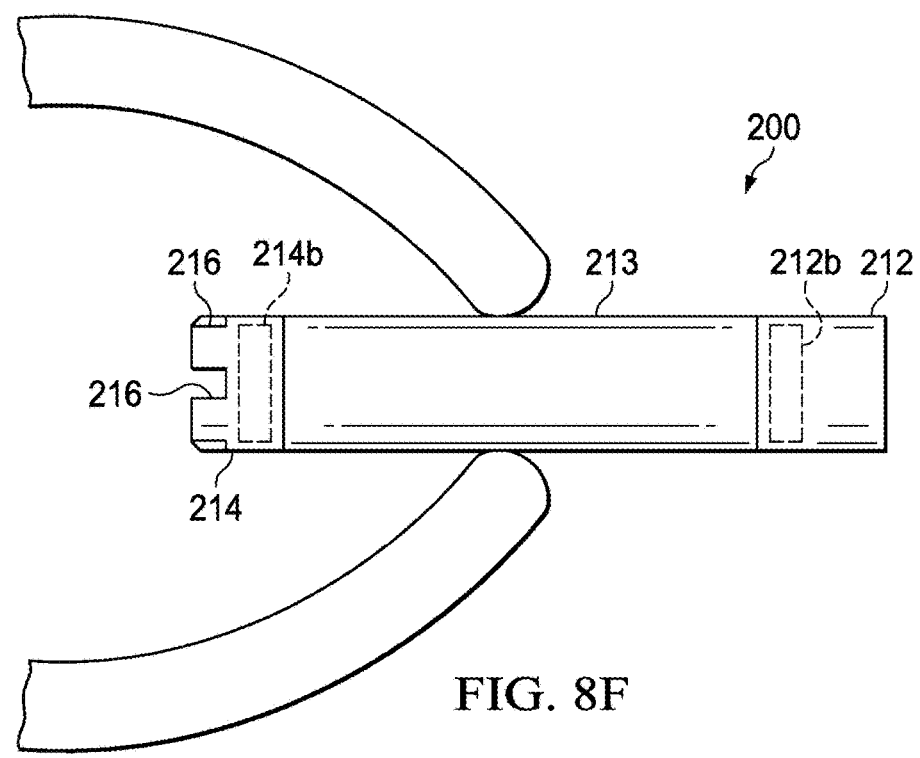
FIGS. 8F-K are illustrations of a side view of an example embodiment of a method of configuring a surgical device in a reverse-directed position.

After the workable volume/space in the cavity has been formed and the port assembly 210 is secured in position, as illustrated in FIG. 8F, the image capturing assembly 220 may be inserted with the image capturing body 224 inserted last through the central access channel 210a and secured to the anchor port 216 of the port assembly 210. To do so while maintaining the workable volume/space, the first gate assembly 212b may be configured to the open position while the second gate assembly 214b is configured to the closed position. Once the first gate assembly 212b is in the open position, the image capturing assembly 220 may be inserted into the mid section 213. The first gate assembly 212b may then be configured to the closed position after the image capturing assembly 220 passes through the first gate assembly 212b. The second gate assembly 214b may then be configured to the open position. It is recognized in the present disclosure that the workable volume/space in the cavity is maintained via the insufflation since the first gate assembly 212b is configured to the closed position. Once the second gate assembly 214b is in the open position, the image capturing assembly 220 may be inserted completely into the cavity of the patient with the image capturing body 224 being closest to the anchor port 216. The multi-curvable body 222 of the image capturing assembly 220 may then be configured/controlled to curve in one or more locations along the multi-curvable body 222 so that the image capturing assembly 220 can be directed in a reverse-directed position next to the outer surface of the port assembly 210 (as illustrated in FIGS. 2A and 3A). The image capturing assembly 220 may then be provided adjacent to the outer surface of the port assembly 210 so that the anchoring portion 220a of the image capturing assembly 220 is adjacent to the anchor port 216. The anchoring portion 220a of the image capturing assembly 220 may then be secured to the anchor port 216. The second gate assembly 214b may be configured to the closed position after the image capturing assembly 220 passes through the second gate assembly 214b.

The separate image capturing assembly 320 may also be inserted through the port assembly 210 in a similar manner as described above. Once inserted through the port assembly 210 and into the cavity of the patient, the separate image capturing assembly 320 may then be attached/secured to the interior wall of the cavity of the patient via the magnetic anchor 310.

(3) Inserting and Attaching a First Instrument Arm Assembly.

Figure 8G:
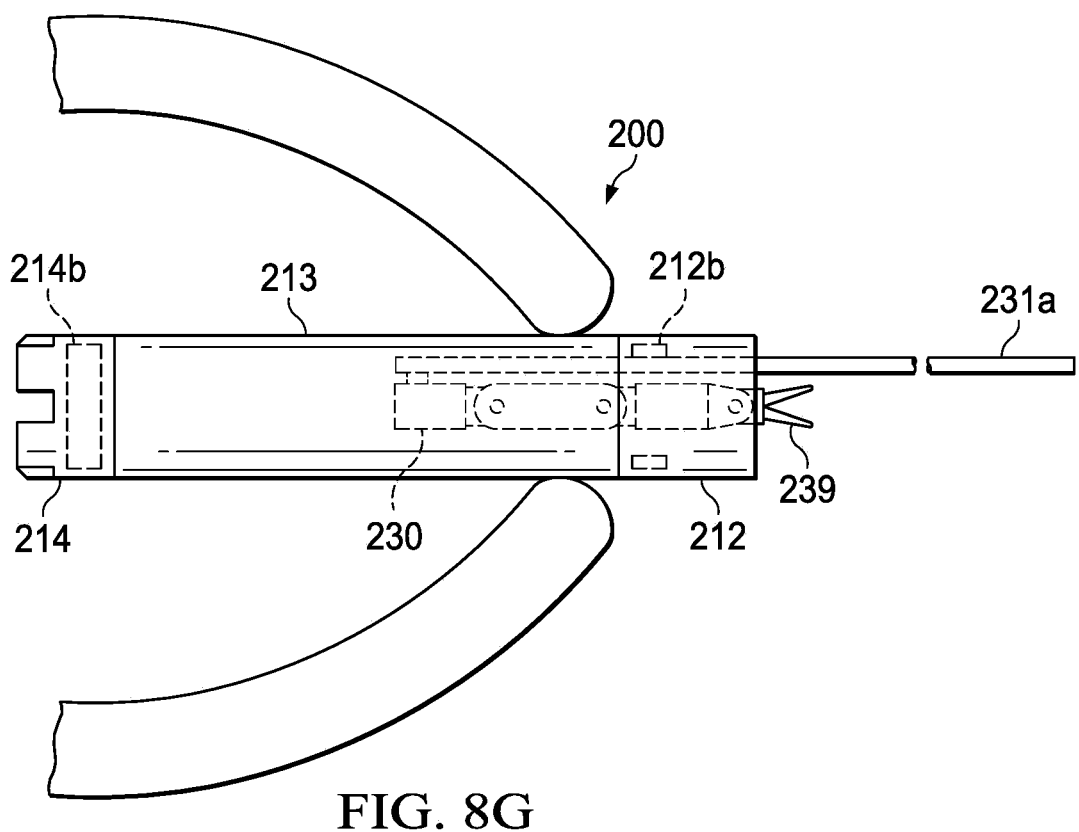
Figure 8H:
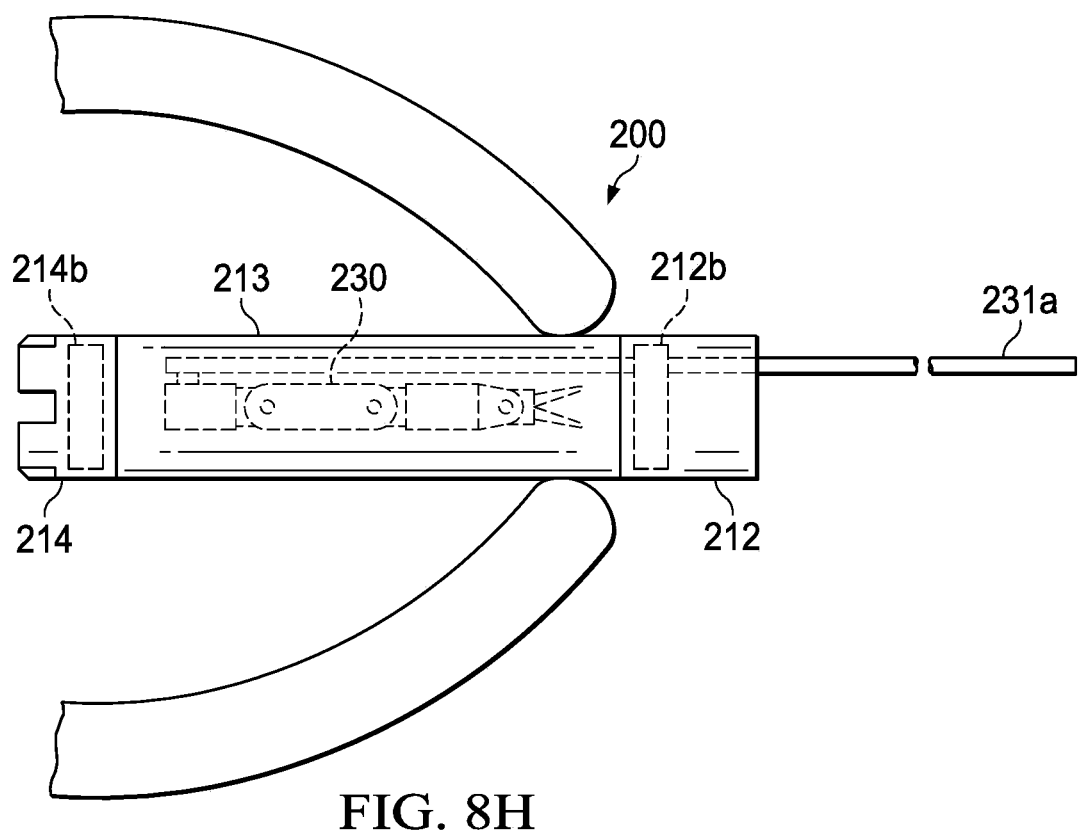
Figure 8I:
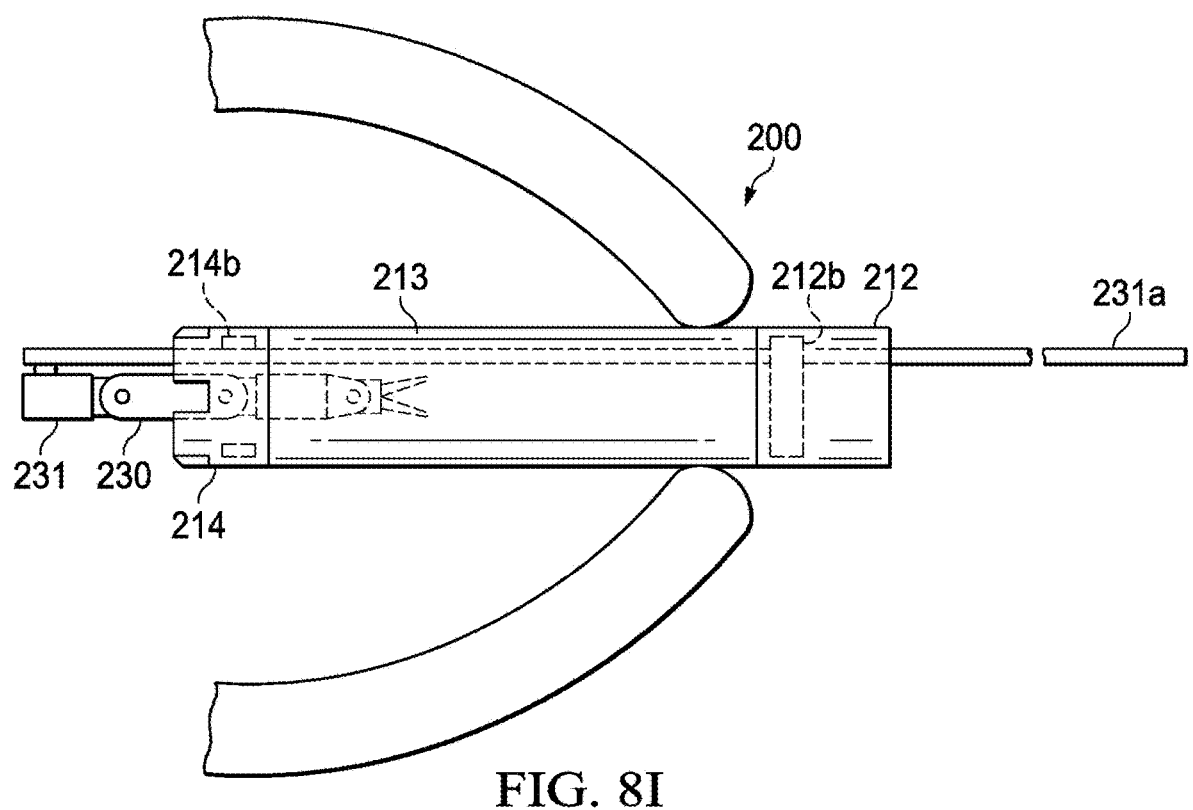
Figure 8J:
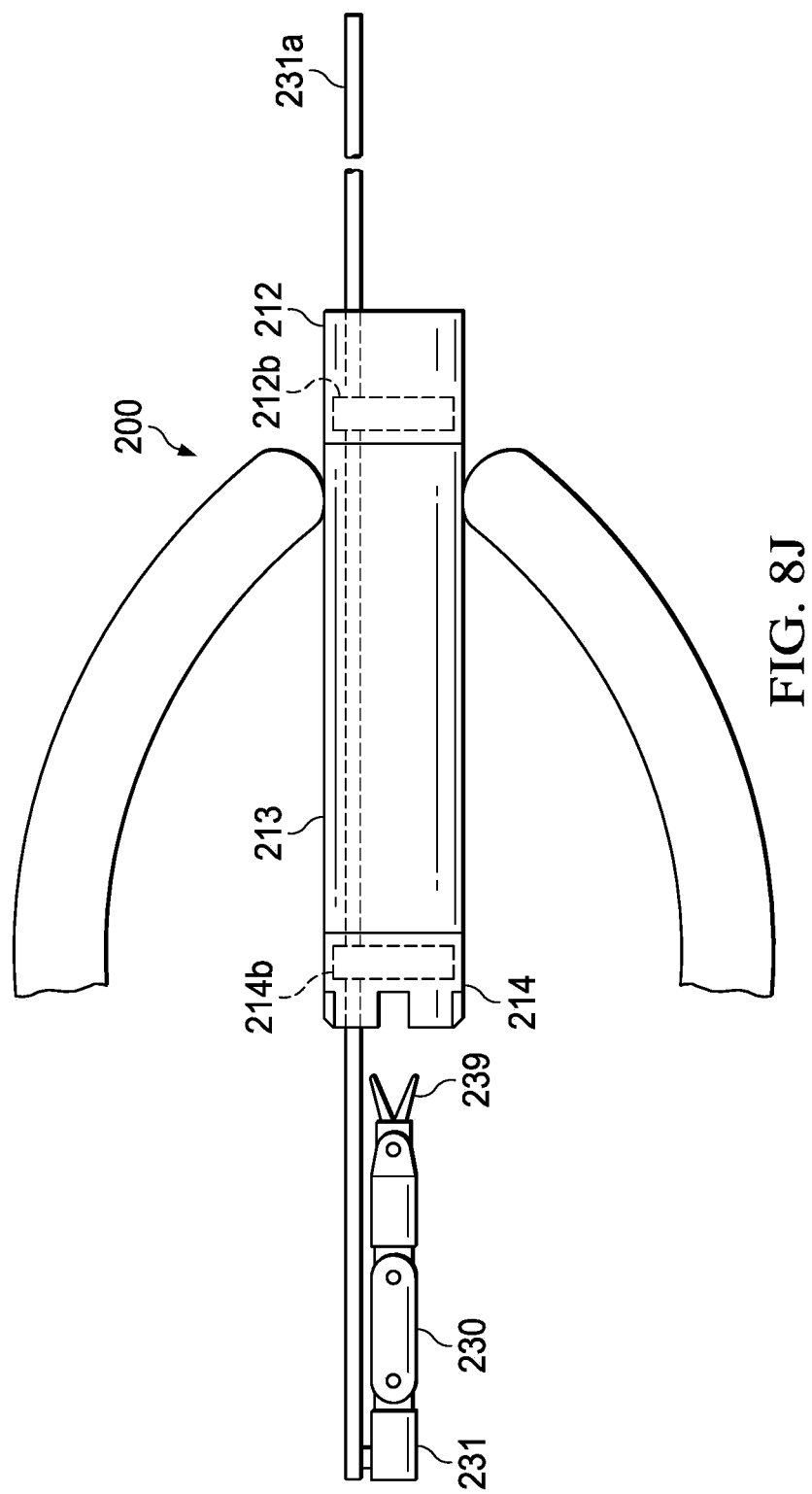
Figure 8K:
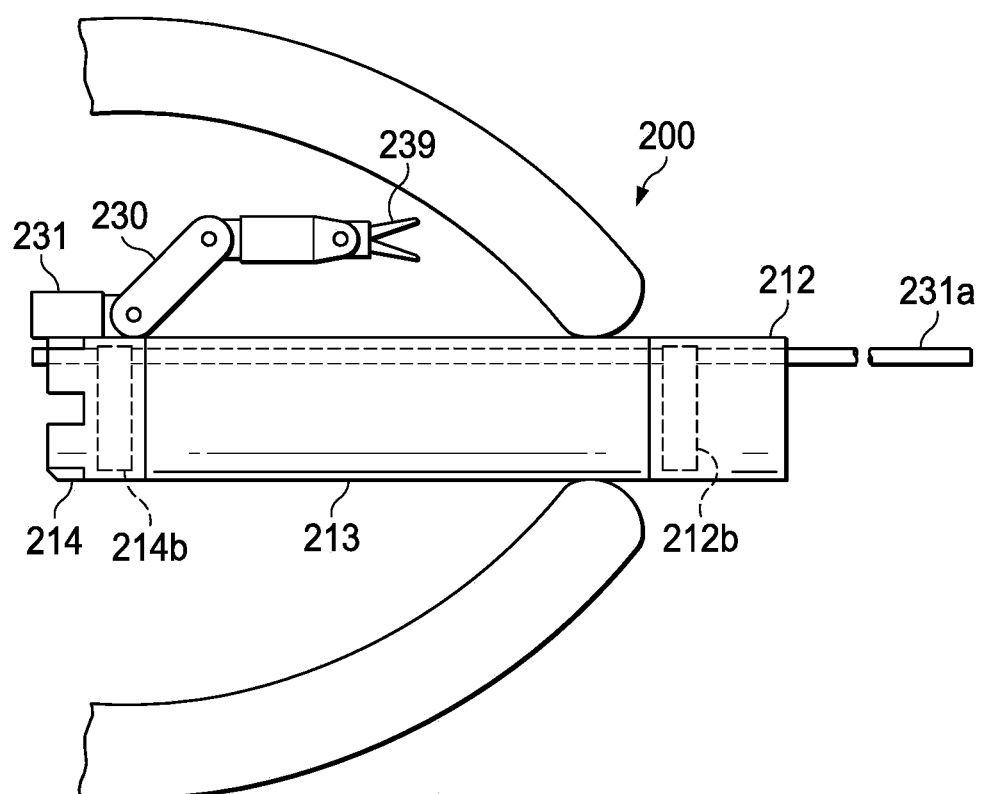

To insert the instrument arm assembly 230 through the central access channel 210a and secure it to the anchor port 216 of the port assembly 210 while maintaining the workable volume/space, the first gate assembly 212b may again be configured to the open position while the second gate assembly 214b is configured to the closed position. Once the first gate assembly 212b is in the open position, the instrument arm assembly 230 may be inserted with the end effector 239 inserted last into the mid section 213, as illustrated in FIG. 8G. The first gate assembly 212b may then be configured to the closed position after the instrument arm assembly 230 passes through the first gate assembly 212b and into the mid section 213, as illustrated in FIG. 8H. The second gate assembly 214b may then be configured to the open position, as illustrated in FIG. 8I. Once the second gate assembly 214b is in the open position, the instrument arm assembly 230 may be inserted completely into the cavity of the patient with the end effector 239 being closest to the anchor port 216, as illustrated in FIG. 8J. The instrument arm assembly 230 may then be turned 180 degrees (if needed) and/or moved so that the instrument arm assembly 230 can be brought next to the outer surface of the port assembly 210. The instrument arm assembly 230 may then be pulled adjacent to the outer surface of the port assembly 210 so that the securing portion 231a of the shoulder section 231 of the instrument arm assembly 230 is adjacent to the anchor port 216. The securing portion 231a of the instrument arm assembly 230 may then be secured to the anchor port 216, as illustrated in FIG. 8K. The second gate assembly 214b may be configured to the closed position at any time after at least the end effector 230 of the instrument arm assembly 230 passes through the second gate assembly 214b.

(5) Inserting and Attaching One or More Additional Instrument Arm Assemblies, One or More Assistant Arm Assemblies, and/or One or More Additional Camera Arm Assemblies.

One or more additional instrument arm assemblies 240, one or more assistant arm assemblies 250 or 260, and/or one or more additional image capturing assemblies (not shown) may also be inserted and installed in a reverse-directed manner via the central access channel 210a of the port assembly 210 in the same manner as described above for the image capturing assembly 220 and the instrument arm assembly 230.

(6) Unattaching and Removing the Instrument Arm Assembly, Image Capturing Assembly, and Assistant Arm Assemblies.

The instrument arm assembly 230, image capturing assembly 220, other instrument arm assembly 240 (if provided), other image capturing assembly (if provided), and the one or more other assistant arm assemblies 250 or 260 (if provided) may be unattached (or unsecured) from the anchor ports 216 and removed from the cavity of the patient via the central access channel 210a of the port assembly 210 in a substantially reverse manner as described above for the inserting and attaching in the reverse-directed manner.

The Surgical System (e.g., Surgical Device 1100)

Figure 11A:
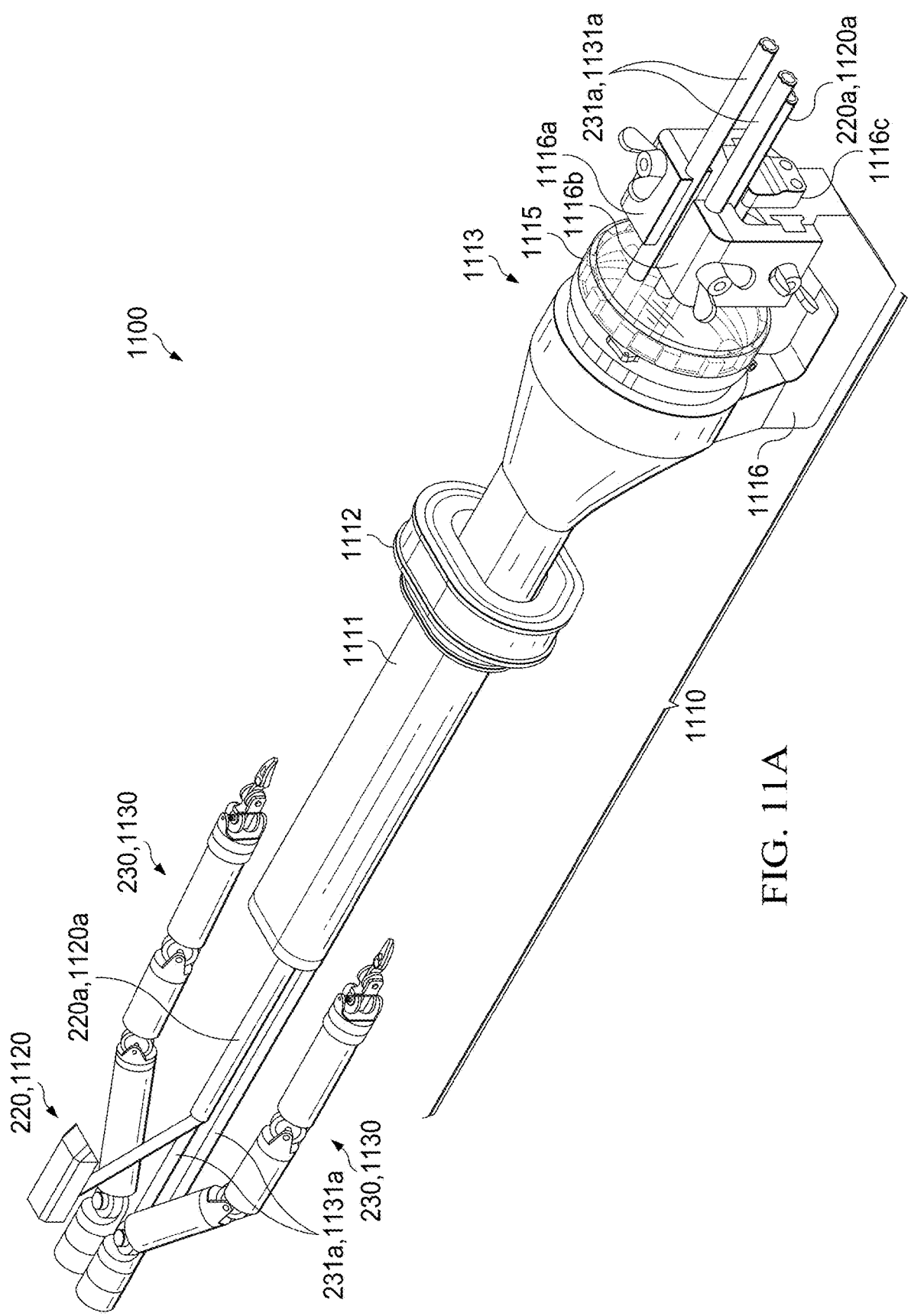
FIG. 11A is an illustration of a perspective view of an example embodiment of the surgical system having surgical arm assemblies in the reverse configuration.
Figure 11B:
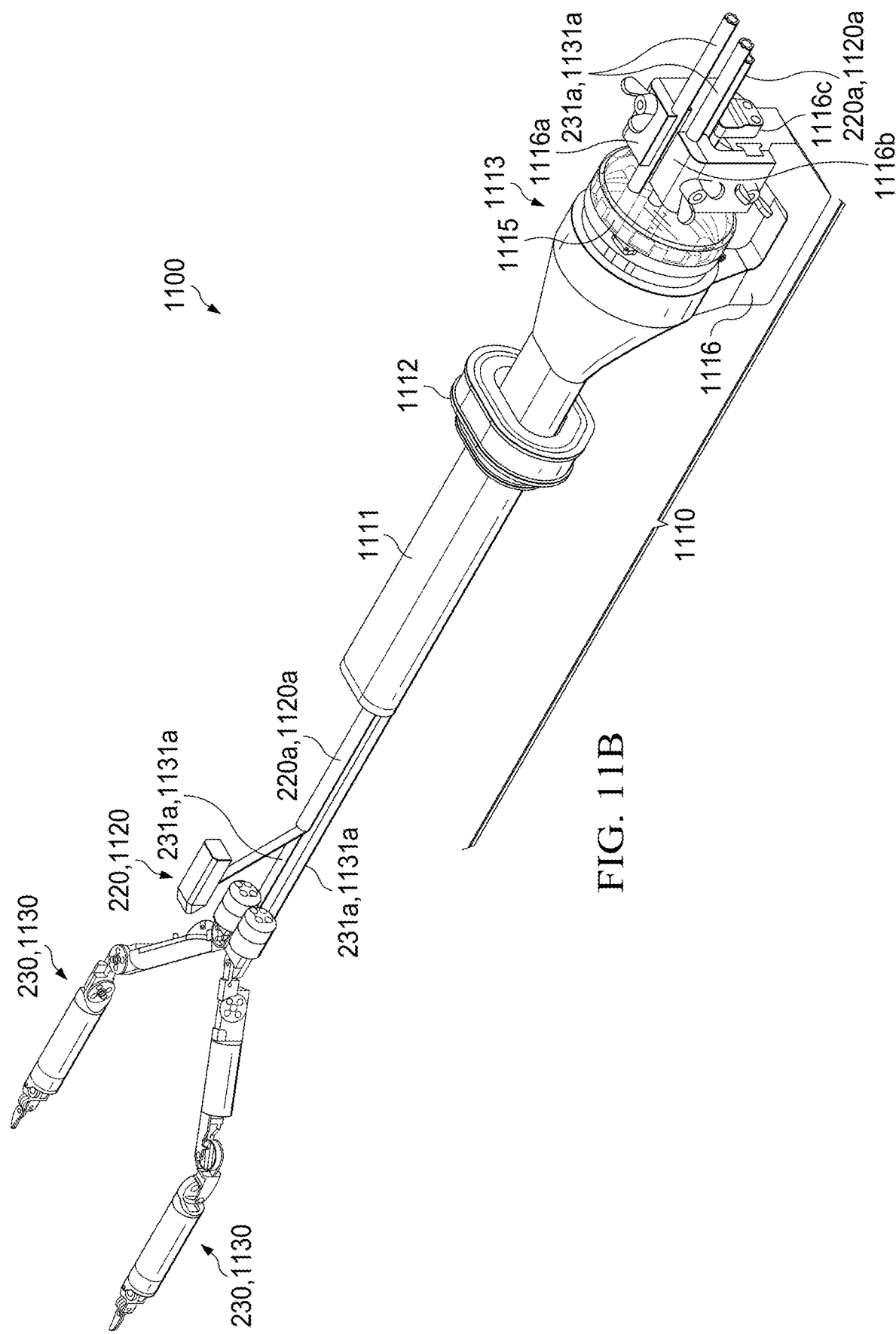
FIG. 11B is an illustration of a perspective view of an example embodiment of the surgical system having surgical arm assemblies in the forward configuration.

An example embodiment of a surgical device or system (e.g., surgical system 1100) is illustrated in at least FIG. 11A and FIG. 11B. The surgical system 1100 may be configurable or configured to be inserted into a cavity of a patient through a single opening, as described above and in the present disclosure. The surgical system 1100 may be anchored (or secured) in position in the single opening via an external anchor (e.g., external anchor 1 or 1000), as described above and in the present disclosure. The surgical system 1100 may include a port assembly (e.g., port assembly 1110). The surgical system 1100 may also include an instrument arm assembly or surgical arm assembly (e.g., surgical arm assembly 230 or 1130, which may be referred to herein as a surgical arm assembly or instrument arm assembly). The surgical system 1100 may also include one or more other elements, such as one or more other surgical arm assemblies (e.g., surgical arm assembly 230 or 1130), one or more image capturing assemblies (e.g., 220 or 1120), one or more assistant arm assemblies (e.g., assistant arm assemblies 250 or 260), etc.

As described above and in the present disclosure, the external anchor 1 or 1000 may be configurable or configured to cooperate with the port assembly 1110 to provide one or more in vitro degrees of freedom (i.e., degrees of freedom within a cavity of a patient). For example, the external anchor 1 or 1000 may be configurable or configured to provide 3 or more in vitro degrees of freedom. In example embodiments, the in vitro degrees of freedom may include a torsional movement, pivotal movement, rotational movement, telescopic movement, and/or other movements of the port assembly 1110 relative to the external anchor 1 or 1000.

The surgical system 1100 may include one or more surgical arm assemblies, such as a first surgical arm assembly (e.g., surgical arm assembly 1130) and a second surgical arm assembly (e.g., surgical arm assembly 1130). One or more of the surgical arm assemblies, including the first surgical arm assembly 230 or 1130 and the second surgical arm assembly 230 or 1130, may be attachable, securable, and/or anchorable (hereinafter referred to as "anchorable", "anchor", "anchoring", or "anchored", each as applicable) to the port assembly 1110. Such surgical arm assemblies 230 or 1130 may be configurable or configured to access and perform one or more surgical actions in/on any and all parts, areas, and/or quadrants within a cavity of the patient. For example, surgical system 1100 may be configurable or configured to perform surgical actions in a forward configuration or direction ("forward configuration"). The forward configuration for a surgical arm assembly 230 or 1130 may be a configuration in which the instrument (e.g., instrument 239 or 1139) of the surgical arm assembly 230 or 1130 is inserted into and through the port assembly 1110 before the shoulder joint (e.g., shoulder joint 232 or 1132) of the surgical arm assembly 230 or 1130 (see, for example, FIGS. 11B and 13B). As another example, the surgical system 1100 may be configurable or configured to perform surgical actions in a reverse configuration or direction ("reverse configuration"). The reverse configuration for a surgical arm assembly 230 or 1130 may be a configuration in which the shoulder joint 232 or 1132 and/or a portion of the elongated anchor section (e.g., elongated anchor section 231a or 1131a) of the surgical arm assembly 230 or 1130 connected to the shoulder joint 232 or 1132 is inserted into and through the port assembly 1110 before the instrument 239 or 1139 (see, for example, FIGS. 11A, 13A, and 15A-B).

The surgical system 1100 may also include one or more image capturing assemblies, such as image capturing assembly 220 or 1120. The surgical system 1100 may also include one or more assistant arm assemblies, such as a retractor arm assembly 250, as illustrated in FIGS. 2A, 2B, 3A, and 3B. Furthermore, the surgical system 1100 may include one or more other instrument arm assemblies, such as suction/irrigation assembly 260, as illustrated in FIGS. 2A, 2B, 3A, and 3B, that can be inserted into the opening of the patient via the port assembly 1110 before, during, and/or after performing a surgical action or procedure. It is to be understood in the present disclosure that the surgical system 1110 may be configurable or configured in a plurality of configurations and arrangements, including having more or less than two surgical arm assemblies (such as third, fourth, fifth, etc. instrument arm assemblies), more than one image capturing assembly (such as second, third, etc. image capturing assemblies), more or less than one assistant arm assembly (such as second, third, etc. assistant arm assemblies), and/or more or less than one other laparoscopic tool in example embodiments without departing from the teachings of the present disclosure. These elements of the surgical system 1100 will now be further described with reference to accompanying FIGS. 11-15.

The Port Assembly (e.g., Port Assembly 1110).

An example embodiment of the port assembly (e.g., port assembly 1110) is illustrated in FIGS. 11A, 11B, FIG. 14A, FIG. 14B, FIGS. 14C-J, and FIGS. 15A-B. The port assembly 1110 may be configurable or configured to be inserted into a single opening of the patient (such as a single incision or a natural orifice) and fixed in position by an external anchor 1 or 1000.

The port assembly 1110 may include a first main body (e.g., first main body 1113), as illustrated in at least FIGS. 11A-B, FIGS. 14A-B, FIG. 14C, FIGS. 14D-G, and FIG. 14J. The port assembly 1110 may also include a second main body (e.g., second main body 1111), as illustrated in at least FIGS. 11A-B, FIGS. 14A-B, FIG. 14H, and FIG. 14I. In example embodiments, the first main body 1113 may include a first main channel (e.g., first main channel 1114*a*) and one or more anchor channels (e.g., first anchor channel 1114*b*, second anchor channel 1114*c*, third anchor channel 1114*d*), The first main body 1113 may also include one or more anchor ports (e.g., anchor port 1116, first anchor port 1116*a*, second anchor port 1116*b*, third anchor port 1116*c*). The first main body 1113 may also include one or more instrument gates (e.g., instrument gate 1115). In example embodiments, the second main body 1111 may include a second main channel (e.g., second main channel 1111*a*'). The second main body 1111 may also include a seal member (e.g., seal member 1112). The first main body 1113 may also include a seal member (not shown) in addition to or in replacement of the seal member 1112 of the second main body 1111. These and other elements of the port assembly 1110 will now be further described with reference to the accompanying drawings.

(i) The First Main Body (e.g., First Main Body 1113).

As illustrated in at least FIGS. 11A-B, FIGS. 14A-G and FIG. 14J, the port assembly 1110 may include a first main body (e.g., first main body 1113). The first main body 1113 may include an elongated structure or body having a proximal end 1113*b* and a distal end 1113*a*. The elongated structure or body of the first main body 1113 may be tubular in shape, and may include a first main channel 1114*a* formed through the first main body 1113. The first main body 1113 may also include one or more anchor channels (e.g., first anchor channel 1114*b*, second anchor channel 1114*c*, third anchor channel 1114*d*), one or more anchor ports (e.g., anchor port 1116, first anchor port 1116*a*), and/or one or more instrument gates (e.g., instrument gate 1115).

In an example embodiment, a length of the first main body 1113 may be between about 340 to 415 mm, a height of the first main body 1113 may be between about 110 to 145 mm, and a width of the first main body 1113 may be between about 40 to 110 mm.

The first main body 1113 may be formed using any one or more of a plurality of materials, such as plastic, metal, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The First Main Channel (e.g., First Main Channel 1114*a*).

The first main channel 1114*a* of the first main body 1113 may extend between (or through) the proximal and distal ends 1113*b* and 1113*a*, respectively, of the first main body 1113. The first main channel 1114*a* may be formed by or using a portion of an interior surface 1113' of the elongated body of the first main body 1113. The first main channel 1114*a* may have a non-circular cross-sectional shape, as illustrated in at least FIGS. 14E-G.

Figure 14A:
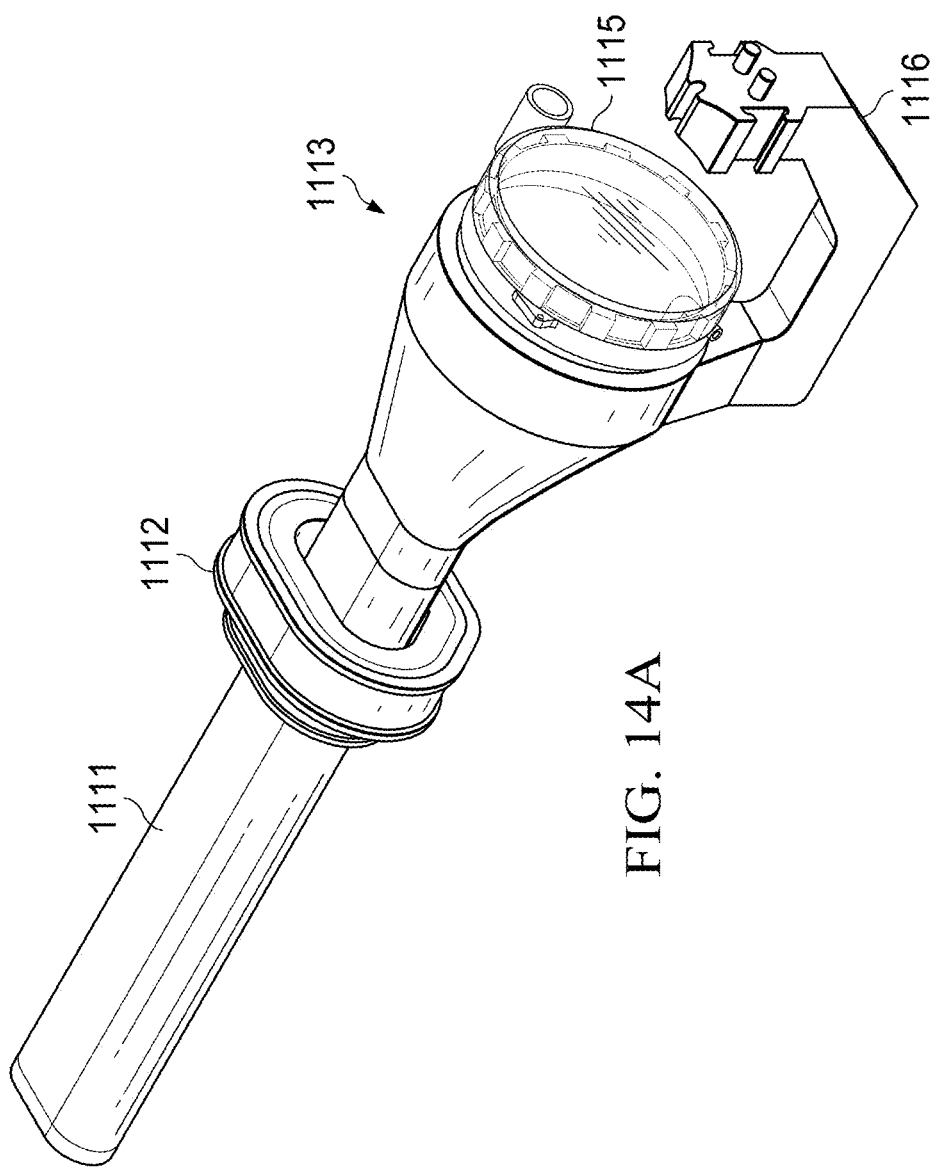
FIG. 14A is an illustration of a perspective view of an example embodiment of the port assembly.
Figure 14B:
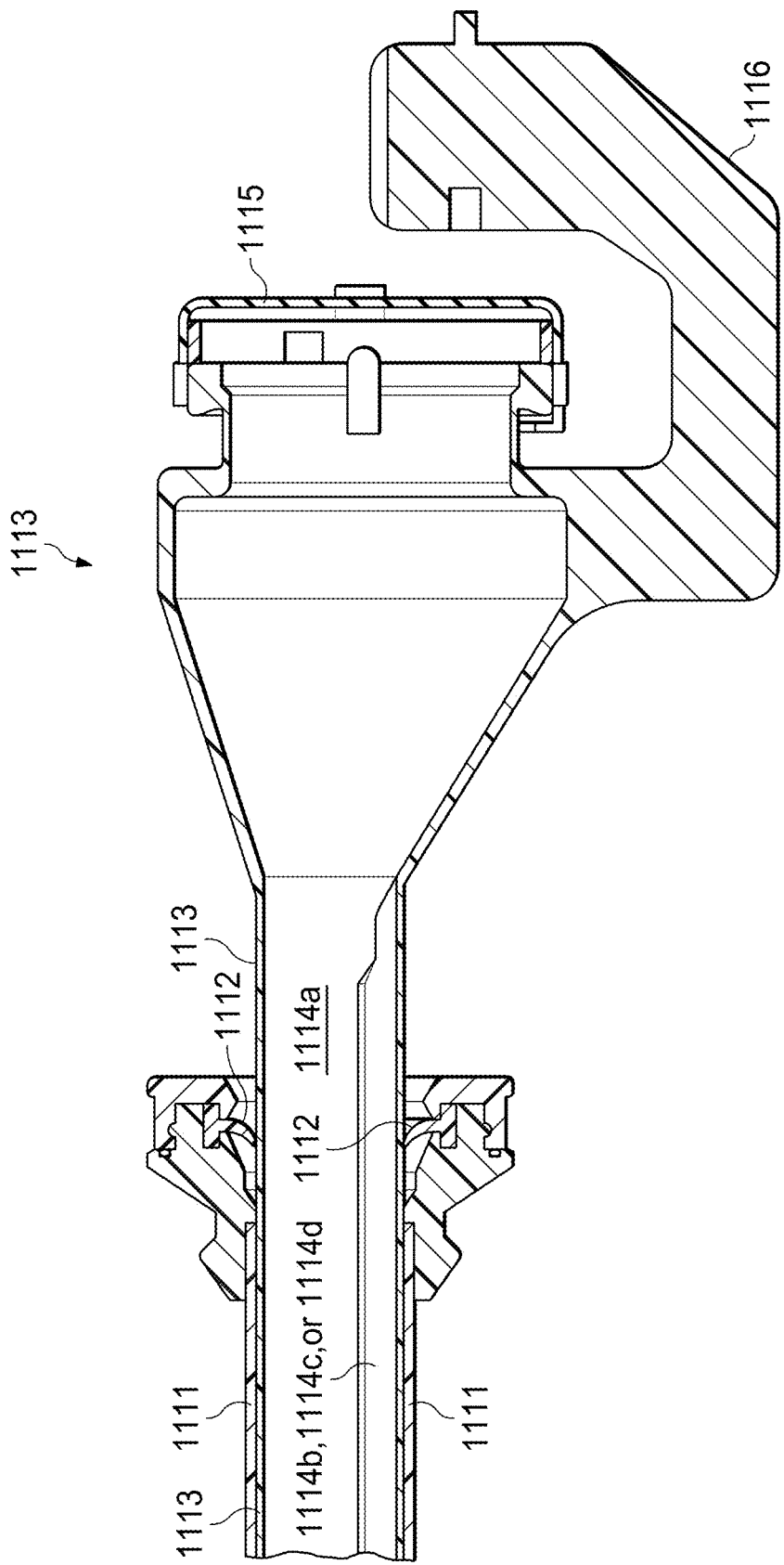
FIG. 14B is an illustration of a cross-sectional view of an example embodiment of the port assembly.
Figure 14C:
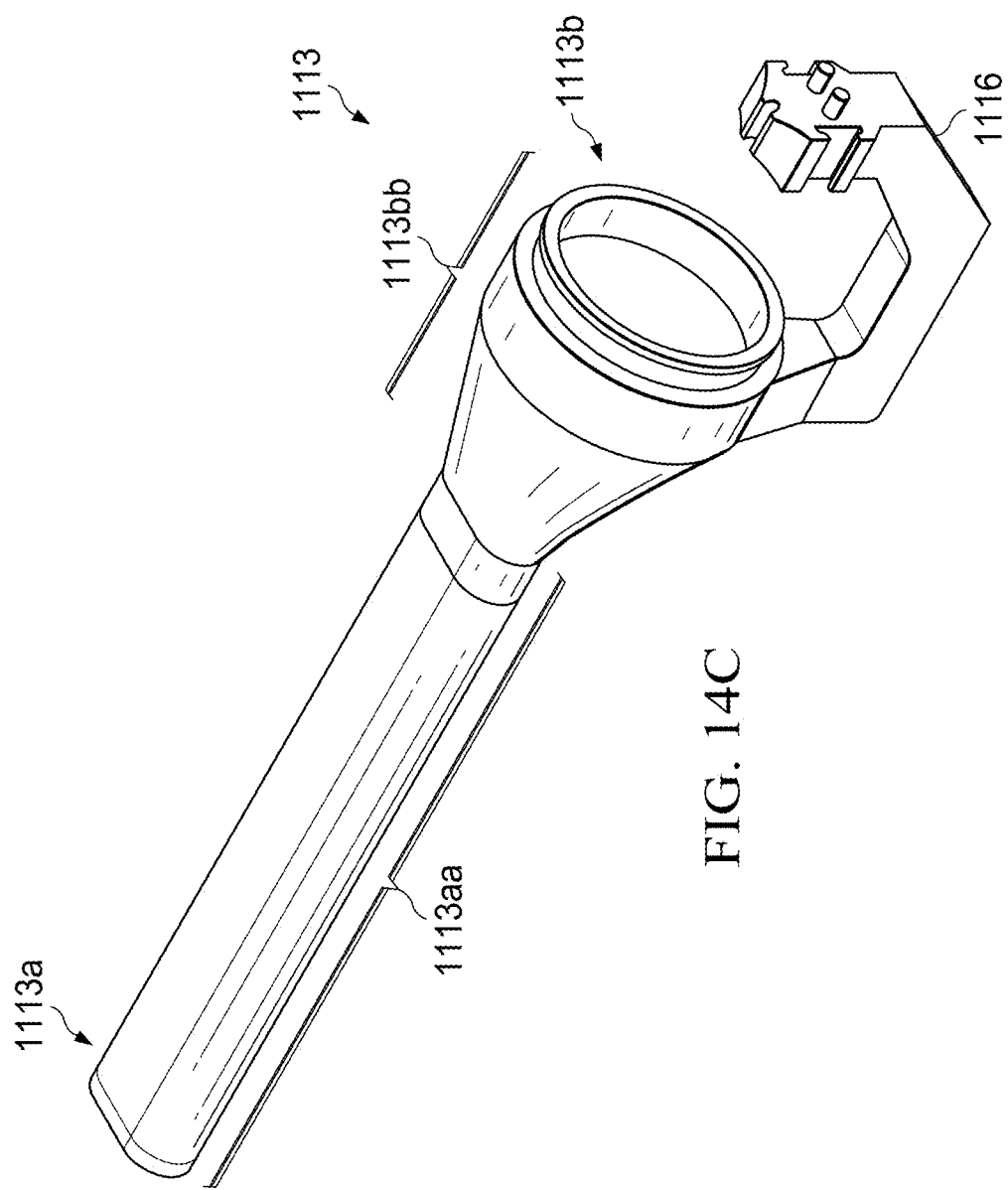
FIG. 14C is an illustration of a perspective view of an example embodiment of the first main body of the port assembly.
Figure 14D:
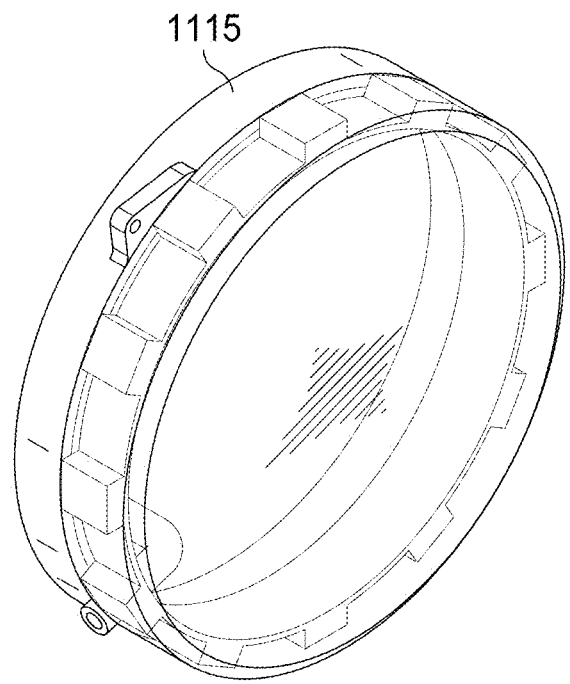
FIG. 14D is an illustration of a perspective view of an example embodiment of the instrument gate.
Figure 14E:
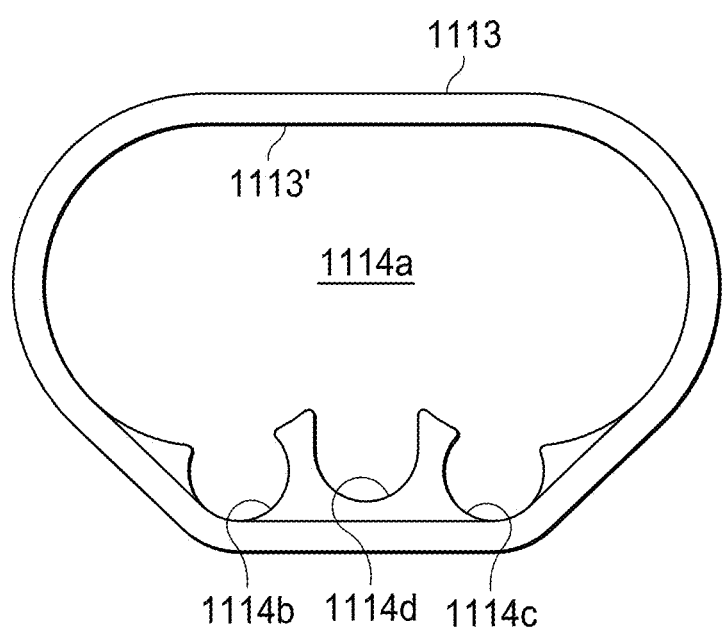
FIG. 14E is an illustration of a cross-sectional view of an example embodiment of the first main body of the port assembly.
Figure 14F:
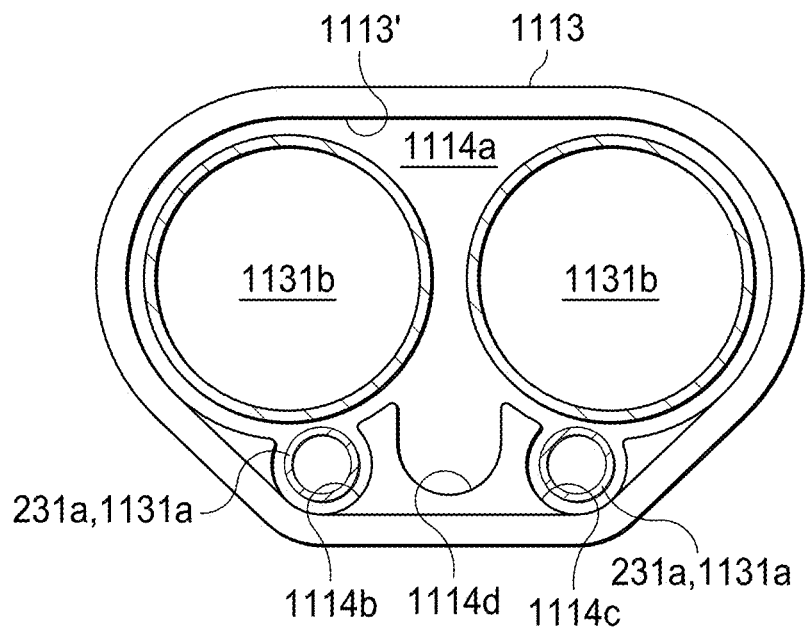
FIG. 14F is an illustration of a cross-sectional view of an example embodiment of the first main body of the port assembly with two surgical arm assemblies in the first main channel of the first main body.
Figure 14G:
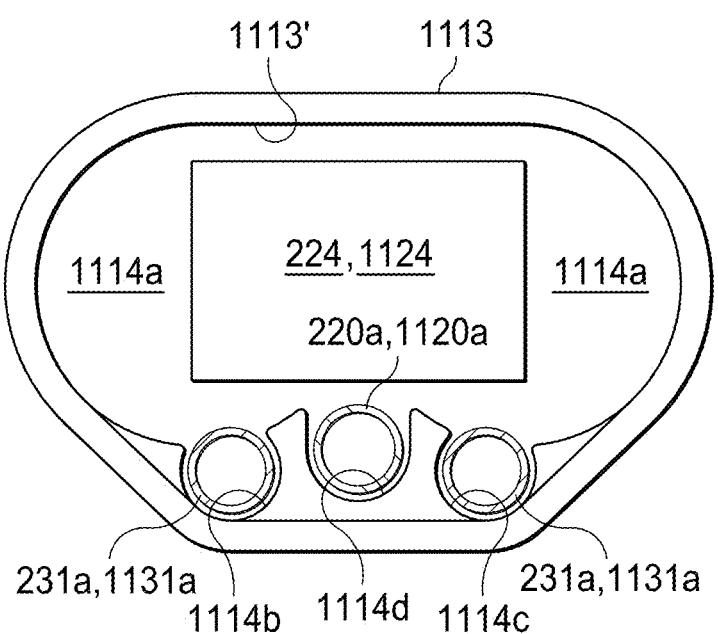
FIG. 14G is an illustration of a cross-sectional view of an example embodiment of the first main body of the port assembly with an image capturing assembly in the first main channel of the first main body.

As illustrated in at least the cross-sectional illustration in FIG. 14E and FIG. 14F, the first main channel 1114*a* may be formed in such a way as to allow a first surgical arm assembly 230 or 1130 (e.g., as represented by the surgical arm 1131*b* of the surgical arm assembly 230 or 1130 on the left or right hand side of FIG. 14F) to pass through the first main channel 1114*a* in either direction (i.e., pass through the first main channel 1114*a* from proximal end 1113*b* to distal end 1113*a* or from distal end 1113*a* to proximal end 1113*b*). Furthermore, the first main channel 1114*a* may be formed in such a way as to allow, when needed, one or two separate surgical arm assemblies 230 or 1130 (e.g., as represented by the two surgical arms 1131*b* of the surgical arm assembly 230 or 1130 on the left and right hand side of FIG. 14F) to pass through the first main channel 1114*a* in the same direction or different directions. For example, the first main body 1113 may be formed so as to provide passage, when needed, of both the first and second surgical arm assemblies 230 or 1130 through the first main channel 1114*a* from proximal end 1113*b* to distal end 1113*a*. Such passing through of both the first and second surgical arm assemblies 230 or 1130 through the first main channel 1114*a* may be performed simultaneously (e.g., the first and second surgical arm assemblies 230 or 1130 are inserted into the first main channel 1114*a* at the same time), near simultaneously (e.g., the first surgical arm assembly 230 or 1130 is inserted into the first main channel 1114*a*, and the second surgical arm assembly 230 or 1130 is inserted into the first main channel 1114*a* while at least a portion of the first surgical arm assembly 230 or 1130 is passing through the first main channel 1114*a*), or sequentially (e.g., the first surgical arm assembly 230 or 1130 is inserted into the first main channel 1114*a* (e.g., as represented by the first surgical arm 1113*b* of the first surgical arm assembly 230 or 1130 on the left hand side of FIG. 14F), and the second surgical arm assembly 230 or 1130 is inserted (e.g., as represented by the second surgical arm 1113*b* of the second surgical arm assembly 230 or 1130 on the right hand side of FIG. 14F) after the first surgical arm assembly 230 or 1130 has completely passed through the first main channel 1114*a*).

As another example, the first main body 1113 may be formed so as to provide passage, when needed, of: (i) the first surgical arm assembly 230 or 1130 (e.g., as represented by the first surgical arm 1131*b* of the first surgical arm assembly 230 or 1130 on the left hand side of FIG. 14F) through the first main channel 1114*a* from the proximal end 1113*b* to the distal end 1113*a*, and (ii) the second surgical arm assembly 230 or 1130 (e.g., as represented by the second surgical arm 1131*b* on the right hand side of FIG. 14F) through the first main channel 1114*a* from the distal end 1113*a* to the proximal end 1113*b*. Such passing through of both the first and second surgical arm assemblies 230 or 1130 through the first main channel 1114*a* may be performed simultaneously (e.g., at the same time), near simultaneously (e.g., the first surgical arm assembly 230 or 1130 (e.g., as represented by the first surgical arm 1113*b* of the first surgical arm assembly 230 or 1130 on the left hand side of FIG. 14F) is passing through the first main channel 1114*a* in a first direction, and the second surgical arm assembly 230 or 1130 (as represented by the second surgical arm 1113*b* of the second surgical arm assembly 230 or 1130 on the right hand side of FIG. 14F) is passed through the first main channel 1114*a* in a second direction (opposite to the first direction) while at least a portion of the first surgical arm assembly 230 or 1130 is passing through the first main channel 1114*a*), or sequentially (e.g., the first surgical arm assembly 230 or 1130 (as represented by the first surgical arm 1113*b* of the first surgical arm assembly 230 or 1130 on the left hand side of FIG. 14F) is passed through the first main channel 1114*a* in either first or second direction, and the second surgical arm assembly 230 or 1130 (e.g., as represented by the second surgical arm 1113*b* of the second surgical arm assembly 230 or 1130 on the right hand side of FIG. 14F) is passed through the first main channel 1114*a* in either first or second direction after the first surgical arm assembly 230 or 1130 has passed through the first main channel 1114*a*). Accordingly, the first main channel 1114*a* may be formed in such a way as to allow one surgical arm assembly 230 or 1130 or two surgical arm assemblies 230 or 1130 to simultaneously, near simultaneously, or sequentially (as described above and in the present disclosure) pass through the first main channel 1114a when needed. It is recognized in the present disclosure that example embodiments of the first main body 1113 enable the first surgical arm assembly 230 or 1130 and the second surgical arm assembly 230 or 1130 to be separately and independently passed through the first main channel 1114a.

After insertion and/or removal of one or both of the first and second surgical arm assemblies 230 or 1130, the first main channel 1114a may be used for inserting and/or removing one or more other instruments, such as one or more other surgical arm assemblies 230 or 1130, one or more image capturing assemblies 220 or 1120, one or more assistant arm assemblies 250, 260, insufflation tubes (not shown in FIGS. 11-15), suction/irrigation tubes (not shown in FIGS. 11-15), etc.

In an example embodiment, a size of the opening (e.g., a cross-section or cross-sectional area) of the first main channel 1114a at the distal end 1113a may be smaller than or the same size as a size of the opening (e.g., cross-section or cross-sectional area) of the first main channel 1114a at the proximal end 1113b, as illustrated in at least FIG. 14C. Furthermore, a shape of the opening of the first main channel 1114a at the distal end 1113a may be similar to, the same as, or different from a shape of the opening of the first main channel 1114a at the proximal end 1113b.

For example, as illustrated in at least FIG. 14C, a size and shape of the first main channel 1114a in the elongated distal section or region 1113aa may remain consistent and the same throughout. However, in example embodiments where the interior channel of the proximal section or region 1113bb is considered to be part of the first main channel 1114a, a size (e.g., cross-sectional area) of the first main channel 1114a (in the proximal section or region 1113bb) may be considered to have a gradually changing (e.g., increasing) size.

As another example (not shown), a size (e.g., cross-sectional area) of the first main channel 1114a in the proximal section or region 1113bb may have an immediate or stepped increase in size and shape as compared to the gradual increase in size illustrated in at least FIGS. 14A-C.

In example embodiments, the first main body 1113 may be formed in one or more of a plurality of ways, including the elongated distal section or region 1113aa and the proximal section or region 1113bb being formed as a unitary article or two or more separate sections secured together. For example, the first main body 1113 may include: (i) an elongated distal section or region (e.g., elongated distal section or region 1113aa, as illustrated in at least FIG. 14C), wherein the portion of the first main channel 1114a formed within such elongated distal section or region 1113aa has a substantially uniform channel size (e.g., substantially uniform or consistent cross-section or cross-sectional area), and (ii) a proximal section or region (e.g., proximal section or region 1113bb, as illustrated in at least FIG. 14C), wherein the portion of the first main channel 1114a formed within such proximal section or region 1113bb has an increased channel size (e.g., immediate or stepped increase in cross-section or cross-sectional area (not shown), or gradually or incrementally increasing cross-section or cross-sectional area that gradually increases towards the distal end 1113b of the first main body 1113 (as illustrated in at least FIGS. 14A-C)). It is to be understood in the present disclosure that the elongated distal section or region 1113aa (having the substantially uniform channel size, cross-section, or cross-sectional area) and the proximal section or region 1113bb (having the immediately increased, stepped, or gradually changing channel size, cross-section, or cross-sectional area) may be formed as a unitary article or as separate elements secured or securable together.

The Anchor Channel (e.g., First Anchor Channel 1114b, Second Anchor Channel 1114c, Third Anchor Channel 1114d).

In an example embodiment, the first main body 1113 may include one or more anchor channels. For example, the first main body 1113 may include a first anchor channel (e.g., first anchor channel 1114b). The first anchor channel 1114b may be a channel that is formed adjacently to the first main channel 1114a throughout the elongated distal section or region 1113aa of the first main body 1113. The first anchor channel 1114b may be connected to and/or include at least one portion of its channel that is opened to and/or shared with the first main channel 1114a, as illustrated in at least FIGS. 14E-G. The first anchor channel 1114b may be configurable or configured to allow the elongated anchor section 231a or 1131a of a surgical arm assembly 230 or 1130 to pass through. In an example embodiment, the first main channel 1114a and the first anchor channel 1114b may be collectively formed in such a way as to allow the first elongated anchor section 231a or 1131a of the first surgical arm assembly 230 or 1130 to pass through the first anchor channel 1114b when the first surgical arm 1131b (as illustrated in at least FIGS. 13A and 13B) of the first surgical arm assembly 230 or 1130 is provided through the first main channel 1114a. See, for example, FIGS. 15A-B, which illustrate the insertion of a surgical arm assembly 230 or 1130 (in a reverse configuration) through the port first main body 1113, including the insertion of the surgical arm 1131b through the first main channel 1114a and the insertion of the elongated anchor section 231a or 1131a through the first anchor channel 1114b, second anchor channel 1114c, or third anchor channel 1114d.

As illustrated in at least FIG. 13B, when the first surgical arm assembly 230 or 1130 is configured in a forward configuration, after the last or most proximal part (e.g., the first shoulder joint 232 or 1132) of the first surgical arm 1131b of the first surgical arm assembly 230 or 1130 is inserted into the proximal end of the first main channel 1114a of the port assembly 1110, the most distal end of the first elongated anchor section 231a or 1131a, which is secured to the first shoulder joint 232 or 1132, is then inserted through the first anchor channel 1114b. Since the first elongated anchor section 231a or 1131a is secured to the first surgical arm 1131b, an opening, slot, or the like, may be provided between the first main channel 1114a and the first anchor channel 1114b so as to connect the first main channel 1114a with the first anchor channel 1114b (or in other words, open up the first main channel 1114a to the first anchor channel 1114b), as illustrated in at least FIGS. 14E-G. As another example, as illustrated in at least FIG. 13A, when the first surgical arm assembly 230 or 1130 is configured in a reverse configuration, as the first or most distal part (e.g., the first shoulder joint 232 or 1132) of the first surgical arm 1131b of the first surgical arm assembly 230 or 1130 is inserted into the proximal end of the first main channel 1114a of the port assembly 1110, the most distal end of the first elongated anchor section 231a or 1131a, which is secured to the first shoulder joint 232 or 1132, is also inserted through the first anchor channel 1114b. Since the first elongated anchor section 231a or 1131a is secured to the first surgical arm 1131b, an opening, slot, or the like, may be provided between the first main channel 1114a and the first anchor channel 1114b so as to connect the first main channel 1114a with the first anchor channel 1114b (or in other words, open up the first main channel 1114a to the first anchor channel 1114b), as illustrated in at least FIGS. 14E-G.

It is recognized in the present disclosure that the collective formation of the first main assembly 1114a and the first anchor channel 1114b may serve to prevent a rotation of the elongated anchor section 231a or 1131a relative to an axis formed by the elongated anchor section 231a or 1131a when the surgical arm assembly 230 or 1130 is inserted through the first main body 1113 of the port assembly 1110.

The first main body 1113 may also include a second anchor channel (e.g., second anchor channel 1114c). The second anchor channel 1114c may be a channel that is formed adjacently to the first main channel 1114a throughout the elongated distal section or region 1113aa of the first main body 1113. The second anchor channel 1114c may be connected to and/or include at least one portion of its channel that is opened to and/or shared with the first main channel 1114a, as illustrated in at least FIGS. 14E-G. Similarly to the first anchor channel 1114b, the second anchor channel 1114c may be configurable or configured to allow the elongated anchor section 231a or 1131a of a surgical arm assembly 230 or 1130 to pass through. In an example embodiment, the first main channel 1114a and the second anchor channel 1114c may be collectively formed in such a way as to allow the second elongated anchor section 231a or 1131a of the second surgical arm assembly 230 or 1130 to pass through the second anchor channel 1114c when the second surgical arm 1131b (as illustrated in at least FIGS. 13A and 13B) of the second surgical arm assembly 230 or 1130 is provided through the first main channel 1114a.

As illustrated in at least FIG. 13B, when the second surgical arm assembly 230 or 1130 is configured in a forward configuration, after the last or most proximal part (e.g., the second shoulder joint 232 or 1132) of the second surgical arm 1131b of the second surgical arm assembly 230 or 1130 is inserted into the proximal end of the first main channel 1114a of the port assembly 1110, the most distal end of the second elongated anchor section 231a or 1131a, which is secured to the second shoulder joint 232 or 1132, is then inserted through the second anchor channel 1114c. Since the second elongated anchor section 231a or 1131a is secured to the second surgical arm 1131b, an opening, slot, or the like, may be provided between the first main channel 1114a and the second anchor channel 1114c so as to connect the first main channel 1114a with the second anchor channel 1114c (or in other words, open up the first main channel 1114a to the second anchor channel 1114c), as illustrated in at least FIGS. 14E-G. As another example, as illustrated in at least FIG. 13A, when the second surgical arm assembly 230 or 1130 is configured in a reverse configuration, as the first or most distal part (e.g., the second shoulder joint 232 or 1132) of the second surgical arm 1131b of the second surgical arm assembly 230 or 1130 is inserted into the proximal end of the first main channel 1114a of the port assembly 1110, the most distal end of the second elongated anchor section 231a or 1131a, which is secured to the second shoulder joint 232 or 1132, is also inserted through the second anchor channel 1114c. Since the second elongated anchor section 231a or 1131a is secured to the second surgical arm 1131b, an opening, slot, or the like, may be provided between the first main channel 1114a and the second anchor channel 1114c so as to connect the first main channel 1114a with the second anchor channel 1114c (or in other words, open up the first main channel 1114a to the second anchor channel 1114c), as illustrated in at least FIGS. 14E-F.

It is recognized in the present disclosure that the collective formation of the first main assembly 1114a and the second anchor channel 1114c may serve to prevent a rotation of the elongated anchor section 231a or 1131a relative to an axis formed by the elongated anchor section 231a or 1131a when the surgical arm assembly 230 or 1130 is inserted through the first main body 1113 of the port assembly 1110.

In an example embodiment, the first main channel 1114a, the first anchor channel 1114b, and the second anchor channel 1114c may be collectively formed in such a way as to allow both the first elongated anchor section 231a or 1131a of the first surgical arm assembly 230 or 1130 and the second elongated anchor section 231a or 1131a of the second surgical arm assembly 230 or 1130, respectively, to pass through the first anchor channel 1114b and the second anchor channel 1114c, respectively, when the first surgical arm 1131b of the first surgical arm assembly 230 or 1130 and the second surgical arm 1131b of the second surgical arm assembly 230 or 1130 is simultaneously (or adjacently) provided through the first main channel 1114a. For example, as illustrated in at least FIG. 13B, when both the first surgical arm assembly 230 or 1130 and the second surgical arm assembly 230 or 1130 are configured in a forward configuration, after the last or most proximal part (e.g., the first shoulder joint 232 or 1132) of the first surgical arm 1131b of the first surgical arm assembly 230 or 1130 and the last or most distal part (e.g., the second shoulder joint 232 or 1132) of the second surgical arm 1131b of the second surgical arm assembly 230 or 1130 are inserted into the proximal end of the first main channel 1114a of the port assembly 1110, the most distal end of the first elongated anchor section 231a or 1131a and the most distal end of the second elongated anchor section 231a or 1131a, each of which are secured to the first shoulder joint 232 or 1132 and the second shoulder joint 232 or 1132, respectively, are then inserted through the first anchor channel 1114b and the second anchor channel 1114c, respectively. As another example, as illustrated in at least FIG. 13A, when both the first surgical arm assembly 230 or 1130 and the second surgical arm assembly 230 or 1130 are configured in a reverse configuration, as the first or most distal part (e.g., the first shoulder joint 232 or 1132) of the first surgical arm 1131b of the first surgical arm assembly 230 or 1130 and the first or most distal part (e.g., the second shoulder joint 232 or 1132) of the second surgical arm 1131b of the second surgical arm assembly 230 or 1130 are inserted into the proximal end of the first main channel 1114a of the port assembly 1110, the most distal end of the first elongated anchor section 231a or 1131a and the most distal end of the second elongated anchor section 231a or 1131a, each of which are secured to the first shoulder joint 232 or 1132 and the second shoulder joint 232 or 1132, respectively, are also inserted through the first anchor channel 1114b and the second anchor channel 1114c, respectively.

It is recognized in the present disclosure that the collective formation of the first main assembly 1114a, the first anchor channel 1114b, and the second anchor channel 1114c may serve to prevent a rotation of the first elongated anchor section 231a or 1131a relative to an axis formed by the first elongated anchor section 231a or 1131a and prevent a rotation of the second elongated anchor section 231a or 1131a relative to an axis formed by the second elongated anchor section 231a or 1131a when the first surgical arm assembly 230 or 1130 and the second surgical arm assembly 230 or 1130 are simultaneously inserted through the first main body 1113 of the port assembly 1110.

The first main body 1113 may also include a third anchor channel (e.g., third anchor channel 1114d). The third anchor channel 1114d may be a channel that is formed adjacently to the first main channel 1114a throughout the elongated distal section or region 1113aa of the first main body 1113. The third anchor channel 1114d may be connected to and/or include at least one portion of its channel that is opened to and/or shared with the first main channel 1114a, as illustrated in at least FIGS. 14E-F. Similarly to the first and second anchor channels 1114b and 1114c, the third anchor channel 1114d may be configurable or configured to allow the elongated anchor section 220a or 1120a of an image capturing assembly 220 or 1120 to pass through. In an example embodiment, the first main channel 1114a and the third anchor channel 1114d may be collectively formed in such a way as to allow the third elongated anchor section 220a or 1120a of the image capturing assembly 220 or 1120 to pass through the third anchor channel 1114d when the image capturing main body 224 or 1124 (as illustrated in at least FIGS. 12A and 12B) of the image capturing assembly 220 or 1120 is provided through the first main channel 1114a. For example, as illustrated in at least FIG. 12B, when the image capturing assembly 220 or 1120 is configured in a forward configuration, after the last or most proximal part of the image capturing main body 224 or 1124 of the image capturing assembly 220 or 1120 is inserted into the proximal end of the first main channel 1114a of the port assembly 1110, the most distal end of the third elongated anchor section 220a or 1120a is then inserted through the third anchor channel 1114d. As another example, as illustrated in at least FIG. 12A, when the image capturing assembly 220 or 1120 is configured in a reverse configuration, as the first or most distal part of the image capturing main body 224 or 1124 of the image capturing assembly 220 or 1120 is inserted into the proximal end of the first main channel 1114a of the port assembly 1110, the most distal end of the third elongated anchor section 220a or 1120a is also inserted through the third anchor channel 1114d.

It is recognized in the present disclosure that the collective formation of the first main assembly 1114a and the third anchor channel 1114d serves to prevent a rotation of the elongated anchor section 220a or 1120a relative to an axis formed by the elongated anchor section 220a or 1120a when the image capturing assembly 220 or 1120 is inserted through the first main body 1113 of the port assembly 1110.

The Anchor Port Assembly (e.g., Anchor Port Assembly 1116).

In an example embodiment, the first main body 1113 may include an anchor port assembly (e.g., anchor port 1116). The anchor port assembly 1116 may include one or more anchor ports. For example, the anchor port assembly 1116 may include a first anchor port (e.g., first anchor port 1116a), second anchor port (e.g., second anchor port 1116b), and third anchor port (e.g., third anchor port 1116c). The anchor port assembly 1116 may be securable or secured at one end to a portion of the proximal end of the first main body 1113, as illustrated in at least FIGS. 11A-B, 14A-C, and 15A-B. Another end of the anchor port assembly 1116 may include the one or more anchor ports, which may be located at locations corresponding to one or more of the anchor channels 1114b, 1114c, and/or 1114d (e.g., locations on or near an axis formed by each of the anchor channels 1114b, 1114c, and 1114d).

In an example embodiment, the first anchor port 1116a may be provided at the proximal end 1113b of the first main body 1113. The first anchor port 1116a may be configurable or configured to anchor (or secure, hold in place, connect, etc.) at least a portion of a proximal end of the first elongated anchor section 231a or 1131a of the first surgical arm assembly 230 or 1130 when the first elongated anchor section 231a or 1131a of the first surgical arm assembly 230 or 1130 is provided through the first anchor channel 1114b of the port assembly 1110. It is recognized in the present disclosure that the anchoring (or securing, holding in place, connecting, etc.) of the proximal end of the first elongated anchor section 231a or 1131a of the first surgical arm assembly 230 or 1130 may prevent, restrict, prohibit, anchor, secure, etc. at least a linear movement of the first elongated anchor section 231a or 1131a of the first surgical arm assembly 230 or 1130 along an axis formed by the first elongated anchor section 231a or 1131a of the first surgical arm assembly 230 or 1130 (and/or along an axis formed by the first anchor channel 1114b). The anchoring (or securing, holding in place, connecting, etc.) of the proximal end of the first elongated anchor section 231a or 1131a of the first surgical arm assembly 230 or 1130 may also prevent, restrict, prohibit, anchor, secure, etc. a rotational movement of the first elongated anchor section 231a or 1131a of the first surgical arm assembly 230 or 1130 relative to an axis formed by the first elongated anchor section 231a or 1131a of the first surgical arm assembly 230 or 1130 (and/or relative to an axis formed by the first anchor channel 1114b).

The first anchor port 1116a may be formed in one or more or a plurality of ways and/or configurations. For example, as illustrated in at least FIG. 14J, the first anchor port 1116a may form or be formed as a C-clamp, or the like, for receiving and securing the first elongated anchor section 231a or 1131a of the first surgical arm assembly 230 or 1130.

In another example embodiment, the second anchor port 1116b may be provided at the proximal end 1113b of the first main body 1113. The second anchor port 1116b may be configurable or configured to anchor (or secure, hold in place, connect, etc.) at least a portion of a proximal end of the second elongated anchor section 231a or 1131a of the second surgical arm assembly 230 or 1130 when the second elongated anchor section 231a or 1131a of the second surgical arm assembly 230 or 1130 is provided through the second anchor channel 1114c of the port assembly 1110. It is recognized in the present disclosure that the anchoring (or securing, holding in place, connecting, etc.) of the proximal end of the second elongated anchor section 231a or 1131a of the second surgical arm assembly 230 or 1130 may prevent, restrict, prohibit, anchor, secure, etc. at least a linear movement of the second elongated anchor section 231a or 1131a of the second surgical arm assembly 230 or 1130 along an axis formed by the second elongated anchor section 231a or 1131a of the second surgical arm assembly 230 or 1130 (and/or along an axis formed by the second anchor channel 1114c). The anchoring (or securing, holding in place, connecting, etc.) of the proximal end of the second elongated anchor section 231a or 1131a of the second surgical arm assembly 230 or 1130 may also prevent, restrict, prohibit, anchor, secure, etc. a rotational movement of the second elongated anchor section 231a or 1131a of the second surgical arm assembly 230 or 1130 relative to an axis formed by the second elongated anchor section 231a or 1131a of the second surgical arm assembly 230 or 1130 (and/or relative to an axis formed by the second anchor channel 1114c).

The second anchor port 1116b may be formed in one or more or a plurality of ways and/or configurations. For example, similar to the first anchor port 1116a, the second anchor port 1116b may form or be formed as a C-clamp, or the like, for receiving and securing the second elongated anchor section 231a or 1131a of the second surgical arm assembly 230 or 1130.

In another example embodiment, the third anchor port 1116c may be provided at the proximal end 1113b of the first main body 1113. The third anchor port 1116c may be configurable or configured to anchor (or secure, hold in place, connect, etc.) at least a portion of a proximal end of the third elongated anchor section 220a or 1120a of the image capturing assembly 220 or 1120 when the third elongated anchor section 220a or 1120a of the image capturing assembly 220 or 1120 is provided through the third anchor channel 1114d of the port assembly 1110. It is recognized in the present disclosure that the anchoring (or securing, holding in place, connecting, etc.) of the proximal end of the third elongated anchor section 220a or 1120a of the image capturing assembly 220 or 1120 may prevent, restrict, prohibit, anchor, secure, etc. at least a linear movement of the third elongated anchor section 220a or 1120a of the image capturing assembly 220 or 1120 along an axis formed by the third elongated anchor section 220a or 1120a of the image capturing assembly 220 or 1120 (and/or along an axis formed by the third anchor channel 1114d). The anchoring (or securing, holding in place, connecting, etc.) of the proximal end of the third elongated anchor section 220a or 1120a of the image capturing assembly 220 or 1120 may also prevent, restrict, prohibit, anchor, secure, etc. a rotational movement of the third elongated anchor section 220a or 1120a of the image capturing assembly 220 or 1120 relative to an axis formed by the third elongated anchor section 220a or 1120a of the image capturing assembly 220 or 1120 (and/or relative to an axis formed by the third anchor channel 1114d).

The third anchor port 1116c may be formed in one or more or a plurality of ways and/or configurations. For example, similar to the first and second anchor ports 1116a and 1116b, the third anchor port 1116c may form or be formed as a C-clamp, or the like, for receiving the third elongated anchor section 220a or 1120a of the image capturing assembly 220 or 1120.

The Instrument Gate (e.g., Instrument Gate 1115).

As illustrated in at least FIGS. 11A-B, FIGS. 14A-B, FIG. 14D, and FIGS. 15A-B, an example embodiment of the first main body 1113 of the port assembly 1110 may include one or more instrument gates (e.g., instrument gate 1115). One or more of the instrument gates 1115 may be securable or secured at a proximal end of the first main channel 1114a (i.e., at the proximal end 1113b), as illustrated in at least FIGS. 11A-B, 14A-B, and 15A-B.

Each of the instrument gates 1115 may include a first expandable opening, point, slot, slit, or the like (not shown; hereinafter "first expandable opening"). The first expandable opening of the instrument gate 1115 may be configurable or configured to be in a persistently or normally closed or sealed position (hereinafter "persistently closed", "persistent closure", or the like). The first expandable opening of the instrument gate 1115 may be configurable or configured to adaptively expand to a shape of a cross-section of an instrument (such as the first surgical arm 1131b), when the instrument (such as the first surgical arm 1131b) is inserted through the first instrument expandable opening. For example, the first expandable opening of the instrument gate 1115 may be configurable or configured to adaptively expand to a combined shape of a cross-section of the first elongated anchor 231a or 1131a and cross-section of the first surgical arm 1131b when the first surgical arm assembly 230 or 1130 is inserted through the instrument gate 1115 in the reverse configuration. As another example, the first expandable opening of the instrument gate 1115 may be configurable or configured to first adaptively expand to a shape of a cross-section of the first surgical arm 1131b, followed by adaptively expanding to a shape of a cross-section of the first elongated anchor 231a or 1131a when the first surgical arm assembly 230 or 1130 is inserted through the instrument gate 1115 in the forward configuration.

It is recognized in the present disclosure that such persistent closure of the first expandable opening (and the persistent closure of the other expandable openings, including the second and third expandable openings described in the present disclosure) enables the instrument gate 1115 to maintain a pressure level (e.g., positive pressure or insufflation) inside a cavity of a patient before, during, and/or after an insertion and/or removal of the first surgical arm assembly 230 or 1130.

Each of the instrument gates 1115 may also include a second expandable opening, point, slot, slit, or the like (not shown; hereinafter "second expandable opening"). Each second expandable opening may be similar to or the same as the first expandable opening, but provided at a different location along the instrument gate 1115. The second expandable opening of the instrument gate 1115 may be configurable or configured to be in a persistently closed position. The first expandable opening of the instrument gate 1115 may be configurable or configured to adaptively expand to a shape of a cross-section of an instrument (such as the second surgical arm 1131b), when the instrument (such as the second surgical arm 1131b) is inserted through the second instrument expandable opening. For example, the second expandable opening of the instrument gate 1115 may be configurable or configured to adaptively expand to a combined shape of a cross-section of the second elongated anchor 231a or 1131a and cross-section of the second surgical arm 1131b when the second surgical arm assembly 230 or 1130 is inserted through the instrument gate 1115 in the reverse configuration. As another example, the second expandable opening of the instrument gate 1115 may be configurable or configured to first adaptively expand to a shape of a cross-section of the second surgical arm 1131b, followed by adaptively expanding to a shape of a cross-section of the second elongated anchor 231a or 1131a when the second surgical arm assembly 230 or 1130 is inserted through the instrument gate 1115 in the forward configuration.

It is recognized in the present disclosure that such persistent closure of the second expandable opening (and the persistent closure of the other expandable openings, including the first and third expandable openings described in the present disclosure) enables the instrument gate 1115 to maintain a pressure level (e.g., positive pressure or insufflation) inside a cavity of a patient before, during, and/or after an insertion and/or removal of the second surgical arm assembly 230 or 1130. It is also recognized that the first and second expandable openings of the instrument gate 1115 are configurable or configured to independently or separately maintain each of its persistently closed position and independently or separately expand to adapt to a shape of an inserted element, instrument, and/or surgical arm assembly (and parts thereof), as described above and in the present disclosure.

Each of the instrument gates 1115 may also include a third expandable opening, point, slot, slit, or the like (not shown; hereinafter "third expandable opening"). Each third expandable opening may be similar to or the same as the first and/or second expandable openings, but provided at a different location along the instrument gate 1115. The third expandable opening of the instrument gate 1115 may be configurable or configured to be in a persistently closed position. The third expandable opening of the instrument gate 1115 may be configurable or configured to adaptively expand to a shape of a cross-section of an instrument (such as the image capturing main body 224, 1124), when the instrument (such as the image capturing main body 224, 1124) is inserted through the third instrument expandable opening. For example, the third expandable opening of the instrument gate 1115 may be configurable or configured to adaptively expand to a combined shape of a cross-section of the third elongated anchor 220a or 1120a and cross-section of the image capturing main body 224 or 1124 when the image capturing assembly 220 or 1120 is inserted through the instrument gate 1115 in the reverse configuration. As another example, the third expandable opening of the instrument gate 1115 may be configurable or configured to first adaptively expand to a shape of a cross-section of the image capturing main body 224 or 1124, followed by adaptively expanding to a shape of a cross-section of the third elongated anchor 220a or 1120a when the image capturing assembly 220 or 1120 is inserted through the instrument gate 1115 in the forward configuration.

It is recognized in the present disclosure that such persistent closure of the third expandable opening (and the persistent closure of the other expandable openings, including the first and second expandable openings described above and in the present disclosure) enables the instrument gate 1115 to maintain a pressure level (e.g., positive pressure or insufflation) inside a cavity of a patient before, during, and/or after an insertion and/or removal of the image capturing assembly 220 or 1120. It is also recognized that the first, second, and third expandable openings of the instrument gate 1115 are configurable or configured to independently or separately maintain each of its persistently closed position and independently or separately expand to adapt to a shape of an inserted element, instrument, and/or surgical arm assembly (and parts thereof), as described above and in the present disclosure.

Figure 14H:
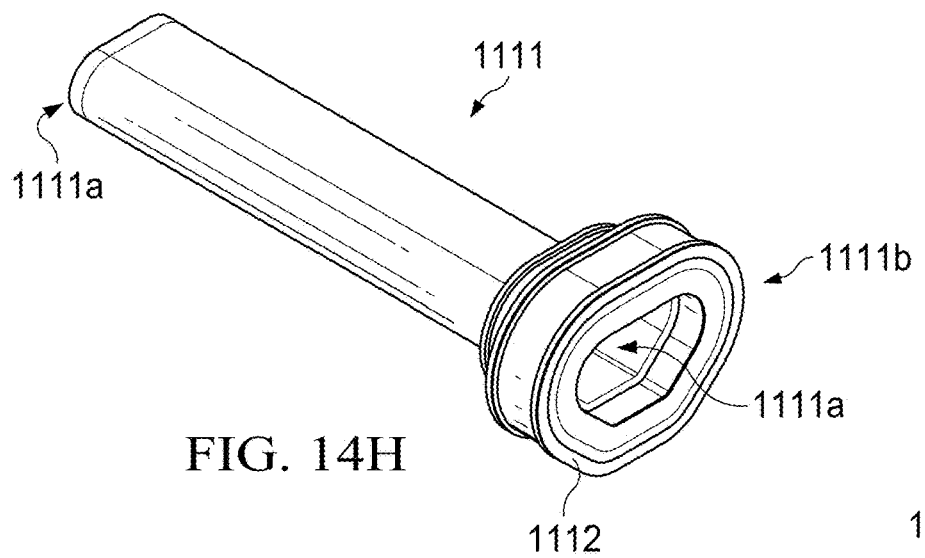
FIG. 14H is an illustration of a perspective view of an example embodiment of the second main body of the port assembly.
Figure 14I:
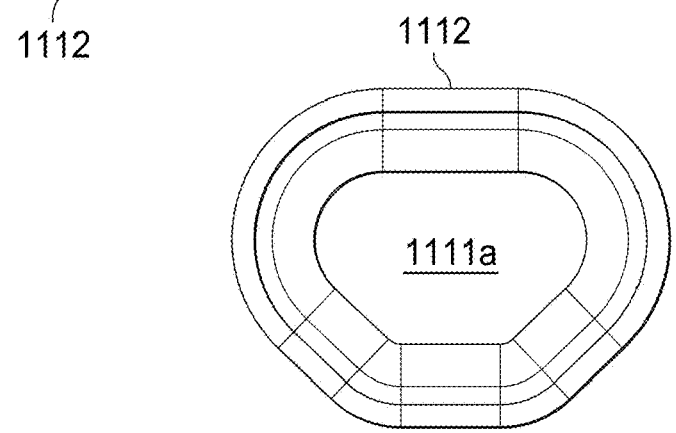
FIG. 14I is an illustration of a frontal view of an example embodiment of the second main body of the port assembly.
Figure 14J:
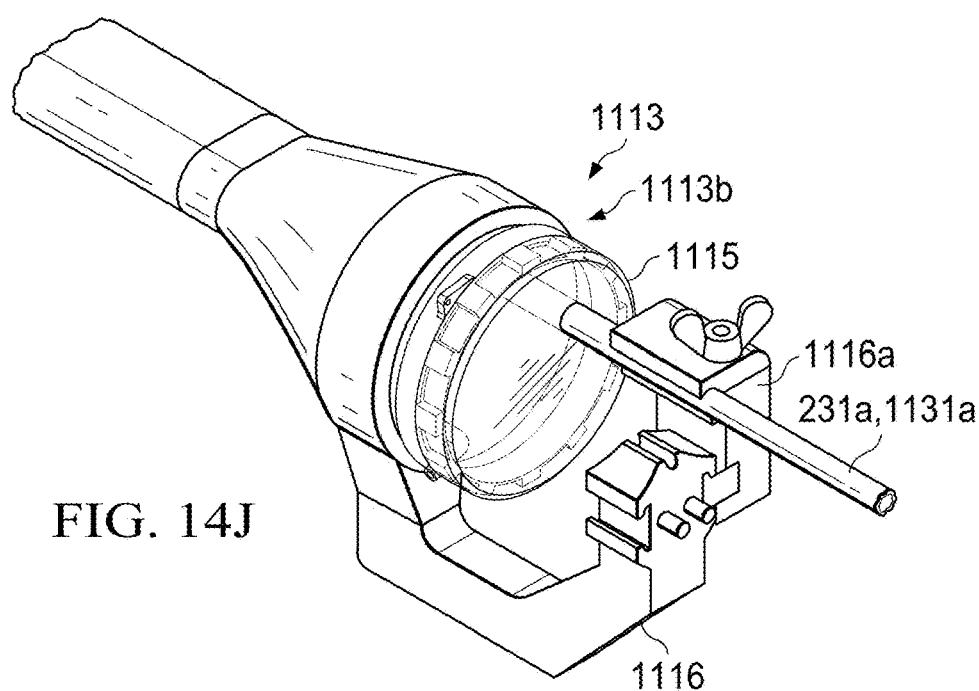
FIG. 14J is an illustration of a perspective view of an example embodiment of the port assembly having a surgical arm assembly anchored to the port assembly via an anchor port.

It is to be understood in the present disclosure that, although the figures illustrate the instrument gate 1115 and the opening of the first main channel 1114a at the proximal end 1113b being in a circular cross-sectional shape, the instrument gate 1115 and the opening of the first main channel 1114a at the proximal end 1113b may be formed in any other shape or configuration, such as a shape that is similar to or the same as the shape of the cross-section of the first main body 1113 illustrated in at least FIGS. 14E-F, the shape of the cross-section of the second main body 1111 or sealing member 1112, as illustrated in at least FIGS. 14H-I, or any other shape or configuration.

In an example embodiment, a dimension (e.g., radius when the instrument gate is formed in a circular shape, as illustrated in the figures) of the instrument gate 1115 may be between about 25 to 50 mm. A thickness of the instrument gate may be between about 10 to 40 mm.

The instrument gate 1115 may be formed using any one or more of a plurality of materials, such as surgical grade rubber, gel, any other flexible material, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

(ii) The Second Main Body (e.g., Second Main Body 1111).

As illustrated in at least FIGS. 11A-B, FIGS. 14A-B, FIGS. 14H-I, and FIGS. 15A-B, the port assembly 1110 may include a second main body (e.g., second main body 1111). The second main body 1111 may include an elongated structure or body having a proximal end 1111b and a distal end 1111a. The elongated structure or body of the second main body 1111 may be tubular in shape, and may include a second main channel 1111c formed through the second main body 1111. The second main body 1111 may also include one or more seal members (e.g., seal member 1112) configured to provide a seal (e.g., hermetic seal) between the second main channel 1111c and the first main body 1113 when the first main body 1113 is housed in the second main channel 1111c.

In an example embodiment, a length of the second main body 1111 may be between about 150 to 220 mm, a height of the second main body 1111 may be between about 20 to 30 mm, and a width of the second main body 1111 may be between about 30 to 45 mm.

The second main body 1111 may be formed using any one or more of a plurality of materials, such as rigid plastic, soft plastic, metal, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Second Main Channel (e.g., Second Main Channel 1111c).

In an example embodiment, the second main body 1111 may include a second main channel (e.g., second main channel 1111c). The second main channel 1111c of the second main body 1111 may extend between the proximal and distal ends 1111b and 1111a, respectively, of the second main body 1111. The second main channel 1111c may be formed by or using at least a portion of an interior surface 1111' of the elongated body of the second main body 1111. When the first main body 1113 is formed in a non-circular cross-sectional shape, as illustrated in at least FIG. 4E, the second main channel 1111c may have a non-circular cross-sectional shape, as illustrated in at least FIG. 14H.

The second main channel 1111c may be formed in such a way as to house at least a portion of the distal end 1113a of the first main body 1113. For example, the second main channel 1111c may be formed so as to firmly or securely house at least a portion of the first main body 1113 when the first main body 1113 is inserted (e.g., the distal end 1113a of the first main body 1113 inserted first) into the second main channel 1111c.

In an example embodiment, a size of the opening (e.g., a cross-section or cross-sectional area) of the second main channel 1111c at the distal end 1111a may be similar to or the same size as a size of the opening (e.g., cross-section or cross-sectional area) of the second main channel 1111c at the proximal end 1111b. Furthermore, a shape of the opening of the second main channel 1111a' at the distal end 1111a may be the same or similar shape as a shape of the opening of the second main channel 1111c at the proximal end 1111b. In example embodiments, the second main body 1111 may be formed in one or more of a plurality of ways, including being formed as a unitary article or two or more separate sections secured together.

The Seal Member (e.g., Seal Member 1112).

In an example embodiment, the second main body 1111 may include one or more seal members (e.g., seal member 1112). Each seal member 1112 may be securable or secured to the second main body 1111. For example, as illustrated in at least FIGS. 11A, 14A-B, and 14H, one of the seal members 1112 may be securable or secured to the proximal end 111b of the second main body 1111.

The seal member 1112 may be configurable or configured to provide, among other things, a seal between the second main channel 1111c and the first main body 1113 when the first main body 1113 is housed in the second main channel 1111c. For example, the seal member 1112 may be configurable or configured to provide a hermetic seal between an interior portion of the second main channel 1111c and an exterior portion of the first main body 1113 when the first main body 1113 is housed in the second main channel 1111c.

The Image Capturing Assembly (e.g., Image Capturing Assembly 220 or 1120).

As illustrated in at least FIGS. 11A-B, FIG. 12A, FIG. 12B, and FIG. 12C, an example embodiment of the surgical system 1100 may include one or more image capturing assemblies (e.g., image capturing assembly 220 or 1120). Each image capturing assembly 220 or 1120 may include an image capturing main body (e.g., image capturing main body 224 or 1124), as described above and in the present disclosure. Each image capturing assembly 220 or 1120 may also include an elongated anchor section (e.g., elongated anchor section or third elongated anchor section 220a or 1120a), as described above and in the present disclosure. Each image capturing assembly 220 or 1120 may also include an image capturing retractor (e.g., image capturing retractor 1120b), as illustrated in at least FIGS. 12C-D.

Figure 12A:
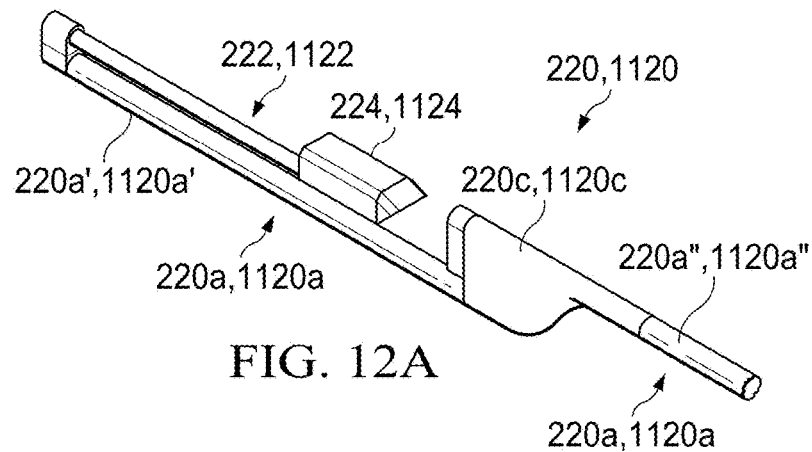
FIG. 12A is an illustration of a perspective view of an example embodiment of the image capturing assembly in the reverse configuration.
Figure 12B:
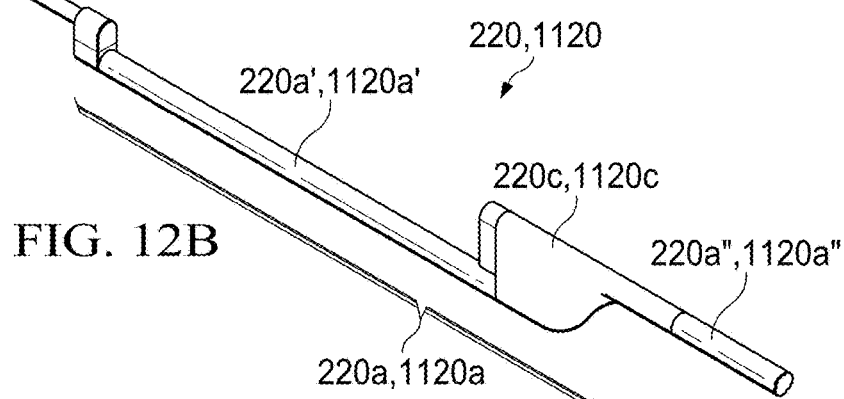
FIG. 12B is an illustration of a perspective view of an example embodiment of the image capturing assembly in the forward configuration.

As illustrated in at least FIG. 12A (for a reverse configuration) and FIG. 12B (for a forward configuration), the elongated anchor section 220a or 1120a may include a distal elongated section (e.g., distal elongated section 220a' or 1120a') configurable or configured to be parallel and adjacent to (but may not be aligned along a same axis as) the image capturing main body 224 or 1124 when the image capturing assembly 220 or 1120 is inserted into the first main body 1113. The elongated anchor section 220a or 1120a may also include a proximal elongated section (e.g., proximal elongated section 220a" or 1120a" configurable or configured to be parallel to and aligned along a same or similar axis (e.g., an axis formed by image capturing main body 224 or 1124 during insertion) as the image capturing main body 224 or 1124. In this regard, the distal elongated section 220a' or 1120a' of the elongated anchor section 220a or 1120a may be positioned in a different axis as the proximal elongated section 220a" or 1120a" of the elongated anchor section 220a or 1120a, as illustrated in at least FIGS. 12A-B. The elongated anchor section 220a or 1120a may also include a midsection transitional section (e.g., midsection transitional section or third midsection transitional section 220c or 1120c). The midsection transitional section 220c or 1120c may be configurable or configured to connect, secure, or attach the distal elongated section 220a' or 1120a' of the elongated anchor section 220a or 1120a with the proximal elongated section 220a" or 1120a" of the elongated anchor section 220a or 1120a, as illustrated in at least FIGS. 12A-B. It is recognized in the present disclosure that the midsection transitional section 220c or 1120c, which may be provided through both the first main channel 1114a and the third anchor channel 1114d when the image capturing assembly 220 or 1120 is inserted through the first main body 1113, enables the image capturing main body 224 or 1124 to completely pass through the distal end 1113a of the first main body 1113 (and the overall port assembly 1110, including the second main body 1111 when the first main body 1113 is housed in the second main channel 1111a' of the second main body 1111), while enabling the third anchor channel 1114d and first main channel 1114a to continue to collectively control, anchor, secure, etc. the distal elongated section 220a' or 1120a' of the elongated anchor section 220a or 1120a. In this regard, when at least a portion of the midsection transitional section 220c or 1120c remains in the third anchor channel 1114d and first main channel 1114a of the first main body 1113, the midsection transitional section 220c or 1120c may be configurable or configured to anchor, control, secure, prevent, etc. a rotation of the image capturing assembly 220 or 1120 relative to an axis formed by the distal elongated section 220a' or 1120a' of the elongated anchor section 220a or 1120a and/or an axis formed by the proximal elongated section 220a" or 1120a" of the elongated anchor section 220a or 1120a.

As described above and in the present disclosure, each image capturing assembly 220 or 1120 may be configurable or configured to be inserted through the first main channel 1114a and the third anchor channel 1114d of the first main body 1113 of the port assembly 1110. Specifically, the image capturing main body 224 or 1124 of the image capturing assembly 220 or 1120 may be provided through (in both directions) the first main channel 1114a and the distal elongated section 220a' or 1120a' of the elongated anchor section 220a or 1120a of the image capturing assembly 220 or 1120 may be provided through (in both directions) the third anchor channel 1114d. The proximal elongated section 220a" or 1120a" of the elongated anchor section 220a or 1120a may be provided through (in both directions) the first main channel 1114a, and the midsection transitional section 220c or 1120c may be provided through (in both directions) both the first main channel 1114a and third anchor channel 1114d.

Figure 12C:
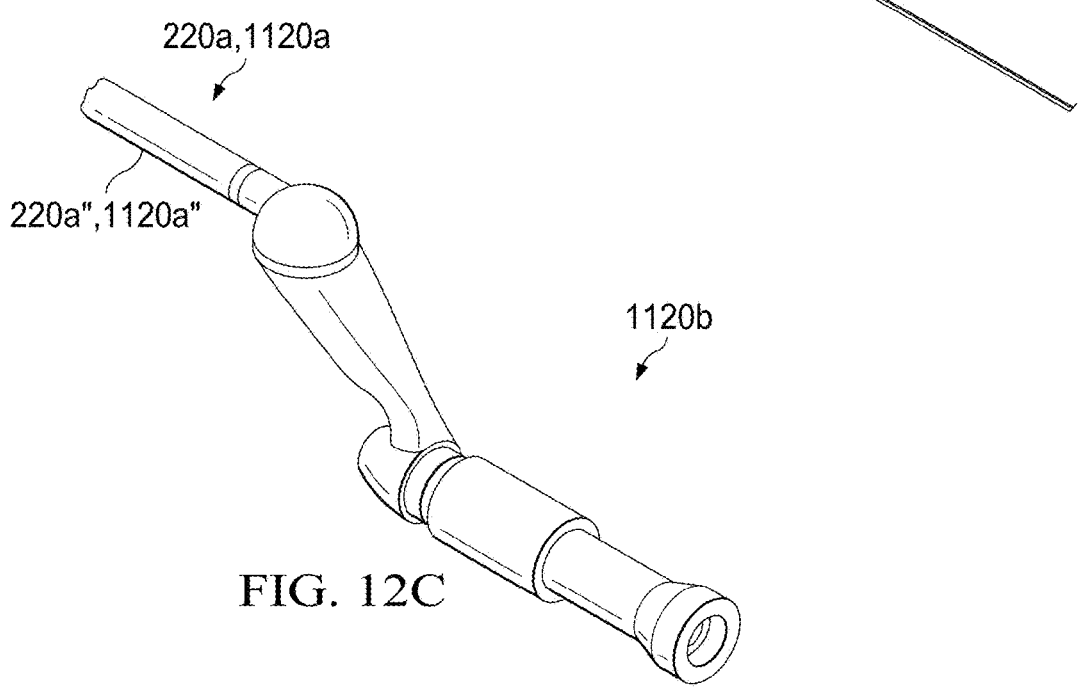
FIG. 12C is an illustration of a perspective view of an example embodiment of the image capturing retractor.

As illustrated in at least FIG. 12C, the image capturing retractor 1120b may be configurable or configured to "shift", translate, or move the proximal elongated section 220a" or 1120a" of the elongated anchor section 220a or 1120a away from the elongated anchor sections 231a or 1131a of the first and second surgical arm assemblies. It is recognized in the present disclosure that such shifting of the proximal elongated section 220a" or 1120a" may provide for more working area or room to access and manipulate the image capturing assembly 220 or 1120 (via the image capturing retractor 1120b) when the image capturing assembly 220 or 1120 is provided through the port assembly 1110. Specifically, such shifting of the proximal elongated section 220a" or 1120a" may effectively move the portion of the elongated anchor section 220a or 1120a of the image capturing assembly 220 or 1120 that is accessible by the surgeon, operator, or control system (not shown) away from the elongated anchor sections 231a or 1131a of the first and second surgical arm assemblies 230 or 1130. It is to be understood in the present disclosure that shifting or moving away may also be provided via a surgical arm retractor (not shown) for the first and/or second surgical arm assemblies 230 or 1130 in addition to or in replacement of the shifting or moving away provided by the image capturing retractor 1120b.

Each image capturing assembly 220 or 1120 may be anchored or secured to the port assembly 1110, as described above and in the present disclosure. One or more of the image capturing assemblies 220 or 1120 may be similar to or the same as the image capturing assembly 220 or 1120 described above and in the present disclosure (e.g., as illustrated in FIGS. 6A-C). For example, as described above and in the present disclosure, one or more of the image capturing assemblies 220 or 1120 may include a multi-curvable body 222 or 1122 (as illustrated in at least FIGS. 6A, 6C, 12A-B, and 12D-E) secured to a distal end of the distal elongated section 220a' or 1120a'. Each multi-curvable body 222 or 1122 may be configurable or configured to curve or bend at one or a plurality of different locations along the multi-curvable body 222 or 1122. Furthermore, as described above and in the present disclosure, for each of the plurality of different locations along the multi-curvable body 222 or 1122 that can be configurable or configured to curve, each such location may be configurable or configured to curve in one of a plurality of different curvatures. A proximal end of the proximal elongated section 220a" or 1120a" of the elongated anchor section 220a or 1120a may be anchored or secured to the first main body 1113 of the port assembly 1110 via the anchor port (e.g., the third anchor port 1116c), as described above and in the present disclosure.

In another example embodiment illustrated in FIG. 12D, the image capturing assembly 220 or 1120 (in a reverse configuration) may include an image capturing main body 224 or 1124, an elongated anchor assembly 220a or 1120a, and an image capturing retractor 1120b. The image capturing assembly 220 or 1120 may also include a multi-curvable body 222, 1122 (as illustrated in at least FIGS. 6A, 6C, 12-A-B, and 12D-E). Unlike the example embodiment of the image capturing assembly 220 or 1120 illustrated in FIGS. 12A-B, an example embodiment of the image capturing assembly 220 or 1120 (as illustrated in FIG. 12D) may not include a midsection transitional section 220c or 1120c. The elongated anchor assembly 220a or 1120a may be formed having a radius of 2-3 mm and an overall length of between about 500-800 mm. As illustrated in FIG. 12D, an example embodiment of the image capturing retractor 1120b may be configurable or configured to function in a different manner as compared to the image capturing retractor 1120b illustrated in FIG. 12C. In such example embodiment, the image capturing retractor 1120b may be configurable or configured to slide or move relative to the elongated anchor section 220a or 1120a so as to assist with the movement of the image capturing main body 224 or 1124 through the first main body 1113 and/or port assembly 1110. In such example embodiment, the image capturing retractor 1120b may (or may not) be configurable or configured to lock in position (i.e., not slide or move) relative to the elongated anchor section 220a or 1120a (e.g., when the image capturing main body 224 or 1124 is not required to move relative to the first main body 1113).

In another example embodiment illustrated in FIG. 12E, the image capturing assembly 220 or 1120 (in a forward configuration) may include an image capturing main body 224 or 1124, an elongated anchor assembly 220a or 1120a, and an image capturing retractor 1120b. The image capturing assembly 220 or 1120 may also include a multi-curvable body 222, 1122 (as illustrated in at least FIGS. 6A, 6C, 12-A-B, and 12D-E). As with the image capturing assembly 220 or 1120 illustrated in FIG. 12D, an example embodiment of the image capturing assembly 220 or 1120 (as illustrated in FIG. 12E) may not include a midsection transitional section 220c or 1120c. The elongated anchor assembly 220a or 1120a may be formed having a radius of 2-3 mm and an overall length of between about 500-800 mm. As illustrated in FIG. 12E, an example embodiment of the image capturing retractor 1120b may be configurable or configured to slide or move relative to the elongated anchor section 220a or 1120a so as to assist with the movement of the image capturing main body 224 or 1124 through the first main body 1113 and/or port assembly 1110. In such example embodiment, the image capturing retractor 1120b may (or may not) be configurable or configured to lock in position (i.e., not slide or move) relative to the elongated anchor section 220a or 1120a (e.g., when the image capturing main body 224 or 1124 is not required to move relative to the first main body 1113).

In example embodiments, the surgical system 1100 may include more than one image capturing assembly 220 or 1120 (and/or more than two surgical arm assemblies 230 or 1130). In such example embodiments, the first main body 1113 may include one or more additional anchor channels (not shown) so as to allow passage of and house the elongated anchor section of such additional image capturing assemblies 220 or 1120 (and/or surgical arm assemblies 230 or 1130).

The Surgical Arm Assembly (e.g., Surgical Arm Assembly 230 or 1130).

As illustrated in at least FIGS. 11A-B, 13A-B, 14F-G, 14J, and 15A-B, an example embodiment of the surgical system 1100 may include one or more surgical arm assemblies (e.g., first surgical arm assembly 230 or 1130 and/or second surgical arm assembly 230 or 1130). Each surgical arm assembly 230 or 1130 may be configurable or configured to be inserted through the port assembly 1110 and secure or anchor to the port assembly 1110. One or more of the surgical arm assemblies 230 or 1130 may be similar to, the same as, or include one or more elements or parts that are the same as the instrument arm assembly 230 or 1130 described above and in the present disclosure.

For example, as described above and in the present disclosure, the first surgical arm assembly 230 or 1130 may include a first surgical arm (e.g., first surgical arm 1131b) and a first elongated anchor section (e.g., first elongated anchor section 231a or 1131a) securable to a first end of the first surgical arm 1131b (e.g., secured to the first shoulder joint 232 or 1132). Similarly, the second surgical arm assembly 230 or 1130 may include a second surgical arm (e.g., second surgical arm 1131b) and a second elongated anchor section (e.g., second elongated anchor section 231a or 1131a) securable to a first end of the second surgical arm 1131b (e.g., secured to the second shoulder joint 232 or 1132).

As described above and in the present disclosure, the first surgical arm 1131b may include a serial arrangement of elements or parts, including a first instrument (e.g., first instrument 239 or 1139, such as a grasper, cutter, etc.) at a second end of the first surgical arm 1131b, a first wrist joint (e.g., first wrist joint 236 or 1136), a first distal arm segment (e.g., first distal arm segment 235 or 1135), a first elbow joint (e.g., first elbow joint 234 or 1134), a first proximal arm segment (e.g., first proximal arm segment 233 or 1133), and/or a first shoulder joint (e.g., first shoulder joint 232 or 1132) at the first end of the first surgical arm 1131b. Similarly, the second surgical arm 1131b may include a serial arrangement of elements or parts, including a second instrument (e.g., second instrument 239 or 1139, such as a grasper, cutter, etc.) at a second end of the second surgical arm 1131b, a second wrist joint (e.g., second wrist joint 236 or 1136), a second distal arm segment (e.g., second distal arm segment 235 or 1135), a second elbow joint (e.g., second elbow joint 234 or 1134), a second proximal arm segment (e.g., second proximal arm segment 233 or 1133), and/or a second shoulder joint (e.g., second shoulder joint 232 or 1132) at the first end of the second surgical arm 1131b. In example embodiments, each surgical arm assembly 230 or 1130 may also include another elbow joint (not shown) that provides for an additional pivotal movement of the distal arm segment 235 or 1135 that is different from the pivotal movement of the distal arm segment 235 or 1135 provided by the elbow joint 234 or 1134 (e.g., the additional elbow joint provides a pivotal movement that is orthogonal to the pivotal movement provided by the elbow joint 234 or 1134).

As illustrated in at least FIG. 13A (for a reverse configuration) and FIG. 13B (for a forward configuration), the elongated anchor section 231a or 1131a may include a distal elongated section 231a' or 1131a' configurable or configured to be parallel and adjacent to (but may not be aligned along a same axis as) the surgical arm 1131b when the surgical arm assembly 230 or 1130 is inserted into the first main body 1113. The elongated anchor section 231a or 1131a may also include a proximal elongated section 231a" or 1131a" configurable or configured to be parallel to and aligned along a same or similar axis as the centerline axis of the surgical arm 1131b. In this regard, the distal elongated section 231a' or 1131a' of the elongated anchor section 231a or 1131a may be positioned in a different axis as the proximal elongated section 231a" or 1131a" of the elongated anchor section 231a or 1131a, as illustrated in at least FIGS. 13A-B. The elongated anchor section 231a or 1131a may also include a midsection transitional section (e.g., midsection transitional section or third midsection transitional section 231c or 1131c). The midsection transitional section 231c or 1131c may be configurable or configured to connect, secure, or attach the distal elongated section 231a' or 1131a' of the elongated anchor section 231a or 1131a with the proximal elongated section 231a" or 1131a" of the elongated anchor section 231a or 1131a, as illustrated in at least FIGS. 13A-B. It is recognized in the present disclosure that the midsection transitional section 231c or 1131c, which may be provided through both the first main channel 1114a and the first anchor channel 1114b (or provided through both the first main channel 1114a and the second anchor channel 1114c for the second surgical arm assembly 230 or 1130), enables the surgical arm 1131b to completely pass through the distal end 1113a of the first main body 1113 (and the overall port assembly 1110, including the second main body 1111 when the first main body 1113 is housed in the second main channel 1111a' of the second main body 1111), while also enabling the first anchor channel 1114b (or the second anchor channel 1114c for the second surgical arm) and first main channel 1114a to collectively control, anchor, secure, etc. the distal elongated section 231a' or 1131a' of the elongated anchor section 231a or 1131a. In this regard, when at least a portion of the midsection transitional section 231c or 1131c remains in the first anchor channel 1114b and first main channel 1114a of the first main body 1113, the midsection transitional section 231c or 1131c may be configurable or configured to anchor, control, secure, prevent, etc. a rotation of the surgical arm assembly 230 or 1130 relative to an axis formed by the distal elongated section 231a' or 1131a' of the elongated anchor section 231a or 1131a and/or an axis formed by the proximal elongated section 231a" or 1131a" of the elongated anchor section 231a or 1131a.

As described above and in the present disclosure, the first surgical arm assembly 230 or 1130 may be configurable or configured to be inserted through the first main channel 1114a and the first anchor channel 1114b of the first main body 1113 of the port assembly 1110. For example, as illustrated in at least FIGS. 14F and 15B, the first surgical arm 1131b of the first surgical arm assembly 230 or 1130 may be provided through (in both directions) the first main channel 1114a and the distal elongated section 231a' or 1131a' of the first elongated anchor section 230a or 1130a of the first surgical arm assembly 230 or 1130 may be provided through (in both directions) the first anchor channel 1114b. The proximal elongated section 231a" or 1131a" of the first elongated anchor section 230a or 1130a may be provided through (in both directions) the first main channel 1114a, and the midsection transitional section 231c or 1131c may be provided through (in both directions) both the first main channel 1114a and first anchor channel 1114b. Similarly, the second surgical arm assembly 230 or 1130 may be configurable or configured to be inserted through the first main channel 1114a and the second anchor channel 1114c of the first main body 1113 of the port assembly 1110. For example, as illustrated in at least FIGS. 14F and 15B, the second surgical arm 1131b of the second surgical arm assembly 230 or 1130 may be provided through (in both directions) the first main channel 1114a and the distal elongated section 231a' or 1131a' of the second elongated anchor section 230a or 1130a of the second surgical arm assembly 230 or 1130 may be provided through (in both directions) the second anchor channel 1114c. The proximal elongated section 231a" or 1131a" of the second elongated anchor section 230a or 1130a may be provided through (in both directions) the first main channel 1114a, and the midsection transitional section 231c or 1131c may be provided through (in both directions) both the first main channel 1114a and second anchor channel 1114c.

Each surgical arm assembly 230 or 1130 may be anchored or secured to the port assembly 1110, as described above and in the present disclosure. One or more of the first and second surgical arm assemblies 230 or 1130 may be similar to or the same as the instrument arm assembly 230, 240, or 1130 described above and in the present disclosure. A proximal end of the proximal elongated section 231a" or 1131a" of the first elongated anchor section 231a or 1131a of the first surgical arm assembly 230 or 1130 may be anchored or secured to the first main body 1113 of the port assembly 1110 via the anchor port (e.g., the first anchor port 1116a), as described above and in the present disclosure. Similarly, a proximal end of the proximal elongated section 231a" or 1131a" of the second elongated anchor section 231a or 1131a of the second surgical arm assembly 230 or 1130 may be anchored or secured to the first main body 1113 of the port assembly 1110 via the anchor port (e.g., the second anchor port 1116b), as described above and in the present disclosure.

In an example embodiment, a length of the distal elongated section 231a' or 1131a' of the elongated anchor section 231a or 1131a may be between about 400 to 700 mm. A dimension (e.g., radius) of the distal elongated section 231a' or 1131a' of the elongated anchor section 231a or 1131a may be between about 2 to 4 mm, and in any event smaller than the dimension (e.g., radius) of the cross-section of the first anchor channel 1114b (and second anchor channel 1114c for the second surgical arm assembly 230 or 1130). A length of the proximal elongated section 231a" or 1131a" of the elongated anchor section 231a or 1131a may be between about 400 to 700 mm. A dimension (e.g., radius) of the proximal elongated section 231a" or 1131a" of the elongated anchor section 231a or 1131a may be between about 2 to 4 mm. An overall length of the midsection transitional section 231c or 1131c of the elongated anchor section 231a or 1131a may be between about 60 to 100 mm. A dimension (e.g., radius) of the midsection transitional section 231c or 1131c of the elongated anchor section 231a or 1131a that passes through the first anchor channel 1114b (or the second anchor channel 1114c for the second surgical arm assembly 230 or 1130) may be between about 2 to 4 mm, and in any event smaller than the dimension (e.g., radius) of the cross-section of the first anchor channel 1114b (and the second anchor channel 1114c for the second surgical arm assembly 230 or 1130). A dimension (e.g., radius) of the midsection transitional section 231c or 1131c of the elongated anchor section 231a or 1131a that passes through the first main channel 1114a may be between about 2 to 4 mm.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, controller, manipulator, master input device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A surgical system, the surgical system comprising:
a first surgical arm assembly, the first surgical arm assembly having a first surgical arm and a first elongated anchor section securable to a first end of the first surgical arm, the first surgical arm including a serial arrangement of a first instrument at a second end of the first surgical arm, a first distal arm segment, a first wrist joint securing the first instrument to the first distal arm segment, a first proximal arm segment, a first elbow joint securing the first distal arm segment to the first proximal arm segment, and a first shoulder joint at the first end of the first surgical arm;
a second surgical arm assembly separate from the first surgical arm assembly, the second surgical arm assembly having a second surgical arm and a second elongated anchor section securable to a first end of the second surgical arm, the second surgical arm including a serial arrangement of a second instrument at a second end of the second surgical arm, a second distal arm segment, a second wrist joint securing the second instrument to the second distal arm segment, a second proximal arm segment, and a second elbow joint portion securing the second distal arm segment to the second proximal arm segment, and a second shoulder joint at the first end of the second surgical arm; and
a port assembly, the port assembly including:
a first main body, the first main body being an elongated body and having:
proximal and distal ends;
a first main channel formed by at least a portion of an interior surface of the elongated body of the first main body, the first main channel extending between the proximal and distal ends of the first main body, the first main channel having a non-circular cross-sectional shape, the first main channel including:
  a left channel, the left channel shaped in such a way as to guide the first surgical arm of the first surgical arm assembly between the proximal and distal ends of the first main body when the first surgical arm of the first surgical arm assembly is received in the left channel;
  a right channel, the right channel shaped in such a way as to guide the second surgical arm of the second surgical arm assembly between the proximal and distal ends of the first main body when the second surgical arm of the second surgical arm assembly is received in the right channel, wherein the right channel is further shaped in such a way as to prevent the second surgical arm of the second surgical arm assembly from moving from the right channel to the left channel when the second surgical arm of the second surgical arm assembly is received in the right channel;
  wherein the left and right channels are formed in such a way as to:
    simultaneously house the first distal arm segment of the first surgical arm in the left channel and the second distal arm segment of the second surgical arm in the right channel; and
    enable the first distal arm segment of the first surgical arm to pass through the left channel at the same time that the second distal arm segment of the second surgical arm passes through the right channel; and
  a first anchor channel and second anchor channel, the first and second anchor channels formed separate from and adjacently to the first main channel;
  wherein the first main channel and the first and second anchor channels are collectively formed in such a way as to allow both the first and second elongated anchor sections of the first and second surgical arm assemblies, respectively, to simultaneously pass through the first and second anchor channels, respectively, when the first and second surgical arms are simultaneously provided through the first main channel;
a second main body, the second main body being an elongated body and having:
  proximal and distal ends;
  a second main channel formed between the proximal and distal ends of the second main body, the second main channel formed in such a way as to receive at least a portion of the first main body, wherein at least a portion of the distal end of the second main channel is configured to receive the at least one portion of the proximal end of the first main body in a hermetically sealable manner;
an instrument gate secured to the proximal end of the second main body, the instrument gate having a first adaptable opening and a second adaptable opening, the first adaptable opening configured to adaptively expand to a combined shape of a cross-section of the first surgical arm assembly and a cross-section of the first elongated anchor section of the first surgical arm assembly, the second adaptable opening configured to adaptively expand to a combined shape of a cross-section of the second surgical arm assembly and a cross-section of the second elongated anchor section of the second surgical arm assembly, wherein the first adaptable opening is configured to maintain a hermetical seal when the first surgical arm assembly and/or the first elongated anchor section of the first surgical arm assembly is inserted through the first adaptable opening; and
an anchor port assembly, the anchor port assembly having:
  a second main body securing portion, the second main body securing portion configured to secure the anchor port assembly to the second main body; and
  a first elongated anchor section securing portion, the first elongated anchor section securing portion configured to secure to at least a portion of a proximal end of the first elongated anchor section of the first surgical arm assembly when the first elongated anchor section of the first surgical arm assembly is inserted through the first adaptable opening of the instrument gate, the first elongated anchor section securing portion configured in such a way that, when the first elongated anchor section of the first surgical arm assembly is secured to the first elongated anchor section securing portion and the second main body securing portion is secured to the second main body:
    the first elongated anchor section of the first surgical arm assembly is prevented from rotating relative to an axis formed by the first elongated anchor section of the first surgical arm assembly; and
    the first elongated anchor section of the first surgical arm assembly is prevented from moving in a linear direction along the axis formed by the first elongated anchor section of the first surgical arm assembly;
wherein the first elongated anchor section of the first surgical arm assembly and the port assembly are configured in such a way that, when the at least one portion of the distal end of the second main channel of the second main body receives the at least one portion of the proximal end of the first main body in the hermetically sealable manner and when the first surgical arm of the first surgical arm assembly is inserted through the first and second main channels:
  a length between proximal and distal ends of the first elongated anchor section is greater than a collective length between the distal end of the first main body and the proximal end of the second main body;
  at least a section of the distal end of the first elongated anchor section extends outwardly away from the distal end of the first main body and is not housed in the first and second main channels; and
  at least a section of the proximal end of the first elongated anchor section extends outwardly away from the proximal end of the second main body and is not housed in the first and second main channels.

2. The surgical system of claim 1, further comprising:
an image capturing assembly separate from the first and second surgical arm assemblies, the image capturing assembly having a main image capturing section and a third elongated anchor section securable to a first end of the main image capturing section;
wherein the port assembly further includes a third anchor channel formed adjacently to the first main channel; and wherein the first main channel and the third anchor channel are collectively formed in such a way as to allow the third elongated anchor section of the image capturing assembly to pass through the third anchor channel when the main image capturing section is provided through the first main channel.

3. The surgical system of claim 1, wherein a cross sectional area of a proximal end of the first main channel is less than a cross sectional area of a distal end of the first main channel.

4. The surgical system of claim 1, wherein the second main body includes a seal member, the seal member configured to provide the hermetic seal between an interior portion of the second main channel and an exterior portion of the first main body when the first main body is housed in the second main channel.

5. The surgical system of claim 1, wherein the anchor port assembly further includes:
   a second elongated anchor section securing portion, the second elongated anchor section securing portion configured to secure to at least a portion of the second elongated anchor section of the second surgical arm assembly when the second elongated anchor section of the second surgical arm assembly is inserted through the second adaptable opening of the instrument gate;
   wherein, when the second main body securing portion is secured to the second main body and the second elongated anchor section of the second surgical arm assembly is secured to the second elongated anchor section securing portion, the second elongated anchor section of the second surgical arm assembly is prevented from rotating relative to an axis formed by the second elongated anchor section of the second surgical arm assembly.

6. The surgical system of claim 1, wherein, when the first elongated anchor section of the first surgical arm assembly is provided in the first anchor channel of the port assembly, the first elongated anchor section and the first anchor channel of the port assembly are configured to cooperate to prevent a rotational movement of the first elongated anchor section relative to an axis formed by the first elongated anchor section.

7. The surgical system of claim 1, wherein one or more of the following apply:
   the first surgical arm assembly is configurable to be in a forward configuration, the forward configuration for the first surgical arm assembly being a configuration in which:
      the second end of the first surgical arm assembly is inserted through the first main channel before the first end of the first surgical arm assembly is inserted through the first main channel; and/or
   the second surgical arm assembly is configurable to be in a forward configuration, the forward configuration for the second surgical arm assembly being a configuration in which:
      the second end of the second surgical arm assembly is inserted through the first main channel before the first end of the second surgical arm assembly is inserted through the first main channel.

8. The surgical system of claim 1, wherein one or more of the following apply:
   the first surgical arm assembly is configurable to be in a reverse configuration, the reverse configuration for the first surgical arm assembly being a configuration in which:
      the first end of the first surgical arm assembly is inserted through the first main channel before the second end of the first surgical arm assembly is inserted through the first main channel; and/or
   the second surgical arm assembly is configurable to be in a reverse configuration, the reverse configuration for the second surgical arm assembly being a configuration in which: the first end of the second surgical arm assembly is inserted through the first main channel before the second end of the second surgical arm assembly is inserted through the first main channel.

9. A surgical system, the surgical system comprising:
   a first surgical arm assembly, the first surgical arm assembly having a first surgical arm and a first elongated anchor section securable to a first end of the first surgical arm, the first surgical arm including a serial arrangement of a first instrument at a second end of the first surgical arm, a first distal arm segment, a first wrist joint securing the first instrument to the first distal arm segment, a first proximal arm segment, a first elbow joint securing the first distal arm segment to the first proximal arm segment, and a first shoulder joint at the first end of the first surgical arm;
   a second surgical arm assembly separate from the first surgical arm assembly, the second surgical arm assembly having a second surgical arm and a second elongated anchor section securable to a first end of the second surgical arm, the second surgical arm including a serial arrangement of a second instrument at a second end of the second surgical arm, a second distal arm segment, a second wrist joint securing the second instrument to the second distal arm segment, a second proximal arm segment, a second elbow joint securing the second distal arm segment to the second proximal arm segment, and a second shoulder joint at the first end of the second surgical arm; and
   a port assembly, the port assembly having:
      an elongated body having proximal and distal ends;
      a main channel formed by at least a portion of an interior surface of the elongated body of the port assembly, the main channel extending between the proximal and distal ends of the elongated body of the port assembly, the main channel having a non-circular cross-sectional shape, the main channel including:
         a left channel, the left channel shaped in such a way as to guide the first surgical arm of the first surgical arm assembly between the proximal and distal ends of the elongated body of the port assembly when the first surgical arm of the first surgical arm assembly is received in the left channel;
         a right channel, the right channel shaped in such a way as to guide the second surgical arm of the second surgical arm assembly between the proximal and distal ends of the elongated body of the port assembly when the second surgical arm of the second surgical arm assembly is received in the right channel, wherein the right channel is further shaped in such a way as to prevent the second surgical arm of the second surgical arm assembly from moving from the right channel to the left channel when the second surgical arm of the second surgical arm assembly is received in the right channel;

wherein the left and right channels are formed in such a way as to:
simultaneously house the first distal arm segment of the first surgical arm in the left channel and the second distal arm segment of the second surgical arm in the right channel; and
enable the first distal arm segment of the first surgical arm to pass through the left channel at the same time that the second distal arm segment of the second surgical arm passes through the right channel;
a first anchor channel and second anchor channel, the first and second anchor channels formed separate from and adjacently to the main channel;
wherein the main channel and the first and second anchor channels are collectively formed in such a way as to allow both the first and second elongated anchor sections of the first and second surgical arm assemblies, respectively, to simultaneously pass through the first and second anchor channels, respectively, when the first and second surgical arms are simultaneously provided through the main channel;
an instrument gate secured to the proximal end of the elongated body, the instrument gate having a first adaptable opening, the first adaptable opening configured to adaptively expand to a combined shape of a cross-section of the first surgical arm assembly and a cross-section of the first elongated anchor section of the first surgical arm assembly, wherein the first adaptable opening is configured to maintain a hermetical seal when the first surgical arm assembly and/or the first elongated anchor section of the first surgical arm assembly is inserted through the first adaptable opening; and
an anchor port assembly, the anchor port assembly having:
an elongated body securing portion, the elongated body securing portion configured to secure the anchor port assembly to the elongated body; and
a first elongated anchor section securing portion, the first elongated anchor section securing portion configured to secure to at least a portion of a proximal end of the first elongated anchor section of the first surgical arm assembly when the first elongated anchor section of the first surgical arm assembly is inserted through the first adaptable opening of the instrument gate, the first elongated anchor section securing portion configured in such a way that, when the first elongated anchor section of the first surgical arm assembly is secured to the first elongated anchor section securing portion and the elongated body securing portion is secured to the elongated body:
the first elongated anchor section of the first surgical arm assembly is prevented from rotating relative to an axis formed by the first elongated anchor section of the first surgical arm assembly; and
the first elongated anchor section of the first surgical arm assembly is prevented from moving in a linear direction along the axis formed by the first elongated anchor section of the first surgical arm assembly;
wherein the first elongated anchor section of the first surgical arm assembly and the port assembly are configured in such a way that, when the first surgical arm of the first surgical arm assembly is inserted through the main channel:
a length between proximal and distal ends of the first elongated anchor section is greater than a length between proximal and distal ends of the elongated body of the port assembly;
at least a section of the distal end of the first elongated anchor section extends outwardly away from the distal end of the elongated body of the port assembly and is not housed in the main channel; and
at least a section of the proximal end of the first elongated anchor section extends outwardly away from the proximal end of the elongated body of the port assembly and is not housed in the main channel.

10. The surgical system of claim 9, further comprising:
an image capturing assembly separate from the first and second surgical arm assemblies, the image capturing assembly having a main image capturing section and a third elongated anchor section securable to a first end of the main image capturing section;
wherein the port assembly further includes a third anchor channel formed adjacently to the main channel; and
wherein the main channel and the third anchor channel are collectively formed in such a way as to allow the third elongated anchor section of the image capturing assembly to pass through the third anchor channel when the main image capturing section is provided through the main channel.

11. The surgical system of claim 9, wherein a cross sectional area of a proximal end of the main channel is less than a cross sectional area of a distal end of the main channel.

12. The surgical system of claim 9, wherein the instrument gate further includes a second adaptable opening, the second adaptable opening configured to adaptively expand to a combined shape of a cross-section of the second surgical arm assembly and a cross-section of the second elongated anchor section of the second surgical arm assembly, wherein the second adaptable opening is configured to maintain a hermetical seal when the second surgical arm assembly and/or the second elongated anchor section of the second surgical arm assembly is inserted through the second adaptable opening;
wherein the anchor port assembly further includes:
a second elongated anchor section securing portion, the second elongated anchor section securing portion configured to secure to at least a portion of the second elongated anchor section of the second surgical arm assembly when the second elongated anchor section of the second surgical arm assembly is inserted through the second adaptable opening of the instrument gate;
wherein, when the second main body securing portion is secured to the second main body and the second elongated anchor section of the second surgical arm assembly is secured to the second elongated anchor section securing portion, the second elongated anchor section of the second surgical arm assembly is prevented from rotating relative to an axis formed by the second elongated anchor section of the second surgical arm assembly.

13. The surgical system of claim 9, wherein one or more of the following apply:
   the first surgical arm assembly is configurable to be in a forward configuration, the forward configuration for the first surgical arm assembly being a configuration in which:
      the second end of the first surgical arm assembly is inserted through the main channel before the first end of the first surgical arm assembly is inserted through the main channel; and/or
   the second surgical arm assembly is configurable to be in a forward configuration, the forward configuration for the second surgical arm assembly being a configuration in which:
      the second end of the second surgical arm assembly is inserted through the main channel before the first end of the second surgical arm assembly is inserted through the main channel.

14. The surgical system of claim 9, wherein one or more of the following apply:
   the first surgical arm assembly is configurable to be in a reverse configuration, the reverse configuration for the first surgical arm assembly being a configuration in which:
      the first end of the first surgical arm assembly is inserted through the main channel before the second end of the first surgical arm assembly is inserted through the main channel; and/or
   the second surgical arm assembly is configurable to be in a reverse configuration, the reverse configuration for the second surgical arm assembly being a configuration in which:
      the first end of the second surgical arm assembly is inserted through the main channel before the second end of the second surgical arm assembly is inserted through the main channel.

15. A port assembly for use with a first surgical arm assembly and a second surgical arm assembly, the first surgical arm assembly having a first surgical arm and a first elongated anchor section secured to the first surgical arm, the second surgical arm assembly having a second surgical arm and a second elongated anchor section, the port assembly comprising:
   a first main body, the first main body having:
      an elongated body with proximal and distal ends;
      a main channel formed by at least a portion of an interior surface of the elongated body, the main channel extending between the proximal and distal ends of the elongated body of the first main body, the main channel having a non-circular cross-sectional shape, the main channel including:
         a left channel, the left channel shaped in such a way as to guide the first surgical arm of the first surgical arm assembly between the proximal and distal ends of the elongated body of the first main body when the first surgical arm of the first surgical arm assembly is received in the left channel; and
         a right channel, the right channel shaped in such a way as to guide the second surgical arm of the second surgical arm assembly between the proximal and distal ends of the elongated body of the first main body when the second surgical arm of the second surgical arm assembly is received in the right channel, wherein the right channel is further shaped in such a way as to prevent the second surgical arm of the second surgical arm assembly from moving from the right channel to the left channel when the second surgical arm of the second surgical arm assembly is received in the right channel;
      wherein the left and right channels are formed in such a way as to:
         simultaneously house the first surgical arm in the left channel and the second surgical arm in the right channel; and
         enable the first surgical arm to pass through the left channel at the same time that the second surgical arm passes through the right channel;
      an anchor channel formed separate from and adjacently to the main channel, wherein the main channel and the anchor channel are collectively formed in such a way as to allow the elongated anchor section of the surgical arm assembly to pass through the anchor channel when the surgical arm of the surgical arm assembly is provided through the main channel;
      an instrument gate secured at the proximal end of the elongated body, the instrument gate having a first adaptable opening, the first adaptable opening configured to adaptively expand to a combined shape of a cross-section of the first surgical arm assembly and a cross-section of the first elongated anchor section of the first surgical arm assembly, wherein the first adaptable opening is configured to maintain a hermetical seal when the first surgical arm assembly and/or the first elongated anchor section of the first surgical arm assembly is inserted through the first adaptable opening; and
      an anchor port assembly, the anchor port assembly having:
         an elongated body securing portion, the elongated body securing portion configured to secure the anchor port assembly to the elongated body; and
         a first elongated anchor section securing portion, the first elongated anchor section securing portion configured to secure to at least a portion of a proximal end of the first elongated anchor section of the first surgical arm assembly when the first elongated anchor section of the first surgical arm assembly is inserted through the first adaptable opening of the instrument gate, the first elongated anchor section securing portion configured in such a way that, when the first elongated anchor section of the first surgical arm assembly is secured to the first elongated anchor section securing portion and the elongated body securing portion is secured to the elongated body:
            the first elongated anchor section of the first surgical arm assembly is prevented from rotating relative to an axis formed by the first elongated anchor section of the first surgical arm assembly; and
            the first elongated anchor section of the first surgical arm assembly is prevented from moving in a linear direction along the axis formed by the first elongated anchor section of the first surgical arm assembly;
   wherein the port assembly is configured in such a way that, when the first surgical arm of the first surgical arm assembly is inserted through the main channel:
      a length between proximal and distal ends of the elongated body of the port assembly is less than a length between proximal and distal ends of the first elongated anchor section;

at least a section of the distal end of the first elongated anchor section extends outwardly away from the distal end of the elongated body of the port assembly and is not housed in the main channel; and at least a section of the proximal end of the first elongated anchor section extends outwardly away from the proximal end of the elongated body of the port assembly and is not housed in the main channel.

16. The port assembly of claim 15, further comprising:
a second main body, the second main body being an elongated body and having a second main channel, the second main channel formed in such a way as to house at least a portion of the first main body in a hermetically sealable manner.

17. The port assembly of claim 15, wherein a cross sectional area of a proximal end of the main channel of the first main body is less than a cross sectional area of a distal end of the main channel of the first main body.

18. The port assembly of claim 16, wherein a cross section of the proximal end of the first main body is greater than a cross section of the second main channel, and wherein the proximal end of the first main body is not housed in the second main channel.

19. The port assembly of claim 15, wherein the instrument gate further includes a second adaptable opening, the second adaptable opening configured to adaptively expand to a combined shape of a cross-section of the second surgical arm assembly and a cross-section of the second elongated anchor section of the second surgical arm assembly, wherein the second adaptable opening is configured to maintain a hermetical seal when the second surgical arm assembly and/or the second elongated anchor section of the second surgical arm assembly is inserted through the second adaptable opening;

wherein the anchor port assembly further includes:
a second elongated anchor section securing portion, the second elongated anchor section securing portion configured to secure to at least a portion of the second elongated anchor section of the second surgical arm assembly when the second elongated anchor section of the second surgical arm assembly is inserted through the second adaptable opening of the instrument gate;

wherein, when the second main body securing portion is secured to the second main body and the second elongated anchor section of the second surgical arm assembly is secured to the second elongated anchor section securing portion, the second elongated anchor section of the second surgical arm assembly is prevented from rotating relative to an axis formed by the second elongated anchor section of the second surgical arm assembly.

* * * * *